(12) United States Patent
Pei et al.

(10) Patent No.: US 7,834,012 B2
(45) Date of Patent: Nov. 16, 2010

(54) PHARMACEUTICAL COMPOSITIONS AS INHIBITORS OF DIPEPTIDYL PEPTIDASE-IV (DPP-IV)

(75) Inventors: Zhonghua Pei, Libertyville, IL (US); Thomas von Geldern, Richmond, IL (US); David J. Madar, Gurnee, IL (US); Xiaofeng Li, Gurnee, IL (US); Fatima Basha, Lake Forest, IL (US); Hong Yong, Libertyville, IL (US); Kenton L. Longenecker, Grayslake, IL (US); Bradley J. Backes, Chicago, IL (US); Andrew S. Judd, Grayslake, IL (US); Mathew M. Mulhern, Lake Villa, IL (US); Kent D. Stewart, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 523 days.

(21) Appl. No.: 11/510,451

(22) Filed: Aug. 25, 2006

(65) Prior Publication Data

US 2007/0049596 A1   Mar. 1, 2007

Related U.S. Application Data

(60) Provisional application No. 60/712,646, filed on Aug. 30, 2005.

(51) Int. Cl.
*A61K 31/535* (2006.01)
*A61K 31/50* (2006.01)
*A61K 31/47* (2006.01)
*A61K 31/445* (2006.01)
*A61K 31/415* (2006.01)
*C07D 295/12* (2006.01)
*C07D 487/04* (2006.01)
*C07D 217/16* (2006.01)
*C07D 211/32* (2006.01)
*C07D 231/12* (2006.01)

(52) U.S. Cl. ............ 514/237.5; 514/249; 514/307; 514/330; 514/406; 544/165; 544/350; 546/146; 546/350; 548/369.4

(58) Field of Classification Search .......... 514/237.5, 514/249, 307, 330, 406; 544/165, 350; 546/146, 546/225; 548/369.4
See application file for complete search history.

(56) References Cited

U.S. PATENT DOCUMENTS 3,068,288 A   12/1962   Godefroi

FOREIGN PATENT DOCUMENTS

| GB | 1328935 | 9/1973 |
| WO | 2004/019945 | 3/2004 |
| WO | 2006/009886 | 1/2006 |
| WO | 2006/066770 | 6/2006 |

OTHER PUBLICATIONS

Beilstein Institut Zur Forderung der Chemischen Wissenchaften, Tetrahedron Letters 41: 515-520 (2000) XP002416885.
Das, P.C., et al., Indian Journal of Chemistry 12(11): 1139-1140 (1974) XP000864336.
Lowry et al., Journal of Pharmaceuticals Sciences 60(4) 632-633 (1971).
Beilstein Institut Zur Forderung der Chemischen Wissenchaften, Journal Chem. Soc. 2249 Abstract (1961) XP002416886.
Beilstein Institut Zur Forderung der Chemischen Wissenchaften, Indian Journal of Chem. 13: 857 Abstract (1975) XP002416887.
Ponomarev et al., Chem. Abstracts Serv. & Metody Polucheniya Khimicheskikh Reaktivov I Preparatov 17: 165-166 (1968) XP002416888.
Darling et al., Journal of Pharm. Sciences 65: 98-102 (1976) XP002416880.
Ahren, B., BioEssays 20: 642-651 (1998).
Ahren B., et al., Diabetes Care 25: 869-875 (2002).
Barreto-Filho et al., J. Clinical Endocrinol. Metab. 87(5): 2018-2023 (2002).
Bulut, K, et al., "Glucagons-like peptide 2 improves intestinal wound healing through induction of epithelial cell migration in vitro—evidence for a TGF-β-mediated effect", Regulatory Peptides, 2004, 121, 137-143.
Colao et al., "The cardiovascular Risk of Adult GH Deficiencey (GHD) Improved after GH Replacement, et al. ", J. Clin. Endocrinol. Metab. 87(3): 1088-1093 (2002).
Deacon, et al.,"Both Subcutaneously and Intravenously Administered Glucagon-Like Peptide I and rapidly Degraded from the NH sub 2-Terminus in type II Diabetic Patients and Healthy Subjects", Diabetes 44: 1126-1131 (1995).
Deacon, et al., "Dipeptidyl Peptidase IV Inhibition Potentiates the Insulinotropic Effect of Glucagon-Like Peptide 1 in the Anesthetized Pig", Diabetes 47: 764-769 (1998).
Drucker, D.J.,, "Glucagon Like Peptides", Diabetes 47: 159-169 (1998)(abstract only).
Drucker et al., Proc. Natl. Acad. Sci. 93: 7911-7916 (1996).
Flint et al., J. Clin. Invest. 101: 515-520 (1998).
Gotherstrom, et al., J. Clin. Endocrinol. Metab. 86(10): 4657-4665 (2001).
Gutniak et al., Journal of Internal Medicine 250: 81-87 (2001).
Gutzwiller et al., Am. J. Physiol. 276: R1541-R1544 (1999).
Zander et al., Diabetes Care 24: 720-725 (2001).
Jeppesen, P.B., et al., Gut, 2005, 54, 1224-1231.
Johannsson, et al., J. Clin. Endocrinol. Metab. 82(3): 727-734 (1997).
Johannsson, et al., Journal of Endocrinology Investment 22 (5 Supp) 41-46 (1999).

(Continued)

*Primary Examiner*—Joseph R Kosack
(74) *Attorney, Agent, or Firm*—Lisa V. Mueller; Polsinelli Shughart PC

(57) ABSTRACT

The present invention relates to compounds, which inhibit dipeptidyl peptidase IV (DPP-IV) and are useful for the prevention or treatment of diabetes, especially type II, as well as hyperglycemia, metabolic syndrome, hyperinsulinemia, obesity, atherosclerosis, various immunomodulatory diseases, and other diseases.

10 Claims, No Drawings

OTHER PUBLICATIONS

Johannsson et al., Metabolism 44: 1126-1129 1995.
Juntti-Berggren et al., Diabetes Care 19: 1200-1206 (1996).
Karl et al., Physiology and Behavior 80: 123-134 (2003).
Knudsen, et al., Eur. Journal of Pharm. 318: 429-435 (1996).
Kubiak et al., Drug Metab. Dispos. 17: 393-397 (1989).
Kumagai et al., Infection and Immunity 73: 2655-2664 (2005).
Lankas, et al., Diabetes, 2005, 54, 2988-2994.
Lautar et al., Brain Research 1048: 177-184 (2005).
Li, Arch. Biochem. Biophy. 1995, vol. 323, pp. 148-154.
Mentlein, et al., Eur. Journal of Biochemistry 214: 829-835 (1993).
Mentlein, R., Regulatory Peptides 85: 9-24 (1999).
Naslund et al., Am. J. Clin. Nutr. 68: 525-530 (1998).
Nauck, et al. Hormone Metabolism. Res. 29: 411-416 (2002).
Ohnuma et al., J. Immunol. 167(12): 6745-6755 (2001).
Ohtsuki et al., FEBS Lett. 431: 236-240 (1998).
Proost et al., FEBS Letters, 432: 73-76 (1998).
Rachman et al., Diabetologia 40: 205-211 (1997).
Reaven, GM, Physiol. Rev. 75: 473-486 (1995).
Shioda et al., Proc. Natl. Acad. Sci. 95(11): 6331-6336 (1998).
Tanaka et al., Proc. Natl. Acad. Sci. 91: 3082-3086 (1994).
Tanaka et al., Proc. Natl. Acad. Sci. 90: 4583 (1993).
Toft-Nielsen et al., Diabetes Care 22: 1137-1143 (1999).

PHARMACEUTICAL COMPOSITIONS AS INHIBITORS OF DIPEPTIDYL PEPTIDASE-IV (DPP-IV)

CROSS-REFERENCE SECTION TO RELATED APPLICATIONS

This application claims the benefit of priority of Provisional U.S. Application Ser. No. 60/712,646, which was filed Aug. 30, 2005, and is incorporated herein by reference in its entirety.

FIELD OF THE INVENTION

The present invention relates to compounds which inhibit dipeptidyl peptidase IV (DPP-IV) and are useful for the prevention or treatment of diabetes, especially type II diabetes, as well as hyperglycemia, metabolic syndrome, hyperinsulinemia, obesity, cardiovascular diseases and disorders including atherosclerosis, cerebrovascular diseases, diseases and disorders of the central nervous system including schizophrenia, anxiety, bipolar disease, depression, insomnia, cognitive disorders, gastrointestinal diseases and disorders, cancer, inflammation and inflammatory diseases, respiratory diseases and disorders, musculo-skeletal disorders, osteoporosis, menopausal symptoms, disorders, periodontal diseases including gingivitis, and various immunomodulatory diseases.

BACKGROUND OF THE INVENTION

Dipeptidyl peptidase IV (DPP-IV, CD26, EC 3.4.14.5) is a serine protease with specificity for cleaving Xaa-Pro and, to a lesser extent, Xaa-Ala dipeptides from the N-termini of polypeptides and proteins. DPP-IV is a non-classical serine protease in that the catalytic triad of Ser-Asp-His, found in the C-terminal region of the enzyme, is in reverse order to that found in classical serine proteases. DPP-IV is widely expressed in mammalian tissue as a type II integral membrane protein. DPP-IV is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates such as chemokines, RANTES (regulated on activation normal T cell expressed and secreted), eotaxin, and macrophage-derived chemokine, neuropeptides such as NPY (neuropeptide Y) and substance P, vasoactive peptides, and incretins such as GLP-1 (glucagon-like peptide-1) and GIP (gastric inhibitory peptide/glucose-dependent insulinotropic polypeptide). GLP-1 is a 30 amino acid peptide hormone produced in the L cells of the distal small intestine in response to ingested nutrients. GLP-1 binding to its receptor on various tissues stimulates insulin gene expression, biosynthesis and glucose-dependent insulin secretion, inhibits glucagon secretion, promotes satiety, slows gastric emptying and promotes growth of pancreatic beta cells. Based on this profile, GLP-1-based therapies are expected to be beneficial in the treatment of type II diabetes and obesity. Studies in which type II diabetic patients have been infused with GLP-1 have demonstrated efficacy in normalizing both fasted and prandial glycemia. However, active GLP-1 (7-36) amide is rapidly converted by DPP-IV to GLP-1 (9-36), which is inactive or is a receptor antagonist. The short half-life of GLP-1 in the circulation (1-1.5 minutes) is a major obstacle to its use as a therapeutic agent. To circumvent the drawback of the short half-life of GLP-1, inhibitors of DPP-IV, the primary degradative enzyme of GLP-1, increase the level of active circulating GLP-1 (7-36) amide. DPP-IV inhibitors have been demonstrated to improve glucose tolerance in type II diabetes.

The inhibition of DPP-IV provides for an attractive therapeutic treatment for type II diabetes and obesity. Although DPP-IV inhibitors have demonstrated improved glucose tolerance in type II diabetes, many suffer from having short half-life and toxicity. Therefore, there is a need for DPP-IV inhibitors having an improved pharmacological profile as an alternative for the treatment of type II diabetes.

SUMMARY OF THE INVENTION

The present invention is directed to compounds of formula (I),

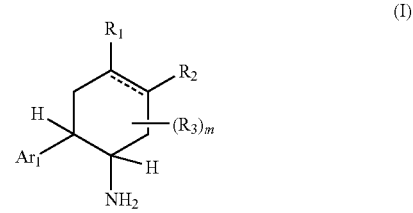

or a pharmaceutically acceptable salt, metabolite, prodrug, salt of a prodrug, or a combination thereof, wherein $R_1$ is selected from the group consisting of hydrogen, alkyl, haloalkyl, aryl, heteroaryl, heterocycle, cycloalkyl and cycloalkenyl; and $R_2$ is selected from the group consisting of hydrogen, alkyl, haloalkyl, cycloalkyl, heterocycle, aryl, heteroaryl, heterocyclealkyl, -alkylenyl-$OR_4$, -alkylenyl-O-alkylenyl-$R_4$, -alkylenyl-$NR_5R_6$, and —C(O)G; or $R_1$ is selected from the group consisting of hydrogen, alkyl, haloalkyl, cycloalkyl, heterocycle, aryl, heteroaryl, heterocyclealkyl, -alkylenyl-$OR_4$, -alkylenyl-O-alkylenyl-$R_4$,-alkylenyl-$NR_5R_6$, and —C(O)G, and $R_2$ is selected from the group consisting of hydrogen, alkyl, haloalkyl, aryl, heteroaryl, heterocycle, cycloalkyl and cycloalkenyl; wherein $R_6$ at each occurrence is independently selected from the group consisting of $R_4$, -alkylenyl-$R_4$, —C(O)$R_4$, —S(O)$_2$$R_4$, —C(O)N$R_4R_5$, —S(O)$_2$N$R_4R_5$, and —C(O)O$R_4$;

G is selected from the group consisting of $R_4$, -alkylenyl-$R_4$, —NR$_5R_4$, and —N(R$_5$)(-alkylenyl-$R_4$);

$R_5$ at each occurrence is selected from the group consisting of hydrogen, alkyl and haloalkyl;

$R_4$ at each occurrence is independently selected from the group consisting of aryl, heteroaryl, cycloalkyl, cycloalkenyl, and heterocycle; wherein the aryl, heteroaryl, heterocycle, cycloalkyl, cycloalkenyl, and the heterocycle moiety of heterocyclealkyl, represented by $R_1$, $R_2$, and $R_4$, are each independently unsubstituted or substituted with 1, 2, 3, 4 or 5 substituents independently selected from the group consisting of $R_7$, alkyl, alkenyl, —CN, —NO$_2$, halo, ethylenedioxy, methylenedioxy, oxo, —O$R_{7A}$, —OC(O)$R_{7A}$, —OC(O)O$R_{7A}$, —OS(O)$_2R_{7A}$, —S(alkyl), —S(O)alkyl, —S(O)$_2R_{7A}$, —S(O)$_2$O$R_{7A}$, —S(O)$_2$N$R_{7A}R_b$, —C(O)$R_{7A}$, —C(O)O$R_{7A}$, —C(O)N$R_{7A}R_b$, —N$R_{7A}R_b$, —NO$R_{7A}$, —N(R$_b$)C(O)$R_{7A}$, —N(R$_b$)C(O)O$R_{7A}$, —N(R$_b$)S(O)$_2R_{7A}$, —N(R$_b$)C(O)N$R_{7A}R_b$, —N(R$_b$)S(O)$_2$N$R_{7A}R_b$, haloalkyl, cyanoalkyl, nitroalkyl, -alkylenyl-OR$_{7A}$, -alkylenyl-OC(O)R$_{7A}$, -alkylenyl-OC(O)OR$_{7A}$, -alkylenyl-OS(O)$_2$R$_{7A}$, -alkylenyl-S(alkyl), -alkylenyl-S(O)alkyl, -alkylenyl-S(O)$_2$R$_{7A}$, -alkylenyl-S(O)$_2$OR$_{7A}$, -alkylenyl-S(O)$_2$NR$_{7A}$R$_b$, -alkylenyl-C(O)$_2$R$_{7A}$, -alkylenyl-C(O)OR$_{7A}$, -alkylenyl-C(O)NR$_{7A}$R$_b$, -alkylenyl-NR$_{7A}$R$_b$, -alkylenyl-NOR$_{7A}$, -alkylenyl-N(R$_b$)C(O)R$_{7A}$, -alkylenyl-N(R$_b$)C(O)OR$_{7A}$, -alkylenyl-N(R$_b$)S(O)$_2$R$_{7A}$, -alkylenyl-N(R$_b$)C(O)NR$_{7A}$R$_b$, -alkylenyl-N(R$_b$)S(O)$_2$NR$_{7A}$R$_b$ and -alkylenyl-R$_7$;

R$_{7A}$ at each occurrence is independently selected from the group consisting of hydrogen, alkyl, alkenyl, haloalkyl, —R$_7$ and -alkylenyl-R$_7$; and R$_7$ at each occurrence is independently selected from the group consisting of aryl, heteroaryl, cycloalkyl, cycloalkenyl and heterocycle;

each R$_3$ is independently selected from the group consisting of hydrogen, alkyl, and haloalkyl;

----- is a single or a double bond;

m is 6 when ----- is a single bond; or m is 4 when ----- is a double bond;

Ar$_1$ is selected from the group consisting of aryl and heteroaryl;

the aryl, heteroaryl, cycloalkyl, cycloalkenyl, and heterocycle represented by Ar$_1$ and R$_7$, are independently unsubstituted or substituted with 1, 2, 3, 4 and 5 substituents independently selected from the group consisting of alkyl, alkenyl, —CN, —NO$_2$, halo, ethylenedioxy, methylenedioxy, oxo, —OR$_a$, —OC(O)alkyl, —OC(O)Oalkyl, —OS(O)$_2$alkyl, —S(alkyl), —S(O)alkyl, —S(O)$_2$alkyl, —S(O)$_2$OR$_a$, —S(O)$_2$NR$_a$R$_b$, —C(O)R$_a$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)alkyl, -alkylenyl-OC(O)Oalkyl, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_2$, -alkylenyl-S(O)$_2$NR$_a$R$_b$, -alkylenyl-C(O)R$_a$, -alkylenyl-C(O)OR$_a$, -alkylenyl-C(O)NR$_a$R$_b$, -alkylenyl-NR$_a$R$_b$, -alkylenyl-NOR$_a$, -alkylenyl-N(R$_b$)C(O)R$_a$, -alkylenyl-N(R$_b$)C(O)OR$_a$, -alkylenyl-N(R$_b$)S(O)$_2$R$_2$, -alkylenyl-N(R$_b$)C(O)NR$_a$R$_b$, and -alkylenyl-N(R$_b$)S(O)$_2$NR$_a$R$_b$;

R$_a$ at each occurrence is independently selected from the group consisting of hydrogen, alkyl, alkenyl and haloalkyl, and R$_b$ at each occurrence is independently selected from the group consisting of hydrogen and alkyl.

The present invention is also directed to pharmaceutical compositions including compounds of the invention. Such compositions can be administered in accordance with a method of the invention, typically as part of a therapeutic regimen for treatment or prevention of conditions and disorders related to DPP-IV. Another aspect of the invention relates to a method of inhibiting DPP-IV activity. The method is useful for treating, or preventing conditions and disorders related to DPP-IV in mammals. More particularly, the method is useful for treating or preventing conditions and disorders related to diabetes, especially type II diabetes, as well as hyperglycemia, syndrome X, hyperinsulinemia, obesity, atherosclerosis, and various immunomodulatory diseases. Accordingly, the compounds and compositions of the invention are useful as a medicament for treating or preventing disease modulated by DPP-IV.

Processes for making compounds of the invention also are contemplated.

The compounds, compositions comprising the compounds, methods for making the compounds, and methods for treating or preventing conditions and disorders by administering the compounds are further described herein.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

Certain terms as used in the specification are intended to refer to the following definitions, as detailed below.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkyl group, as defined herein, in which one or two hydrogen atoms are replaced by alkoxy groups, as defined herein. Representative examples of alkoxyalkyl include, but are not limited to, methoxymethyl and ethoxymethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylenyl" as used herein, means a divalent group derived from a straight or branched chain hydrocarbon of from 1 to 6 carbon atoms. Representative examples of alkylenyl include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, and 5,6,7,8-tetrahydronaphthalenyl. The phenyl and the bicyclic aryl groups of the present invention are unsubstituted or substituted. Examples of substituted phenyl include, but are not limited to, 2-chlorophenyl, 2,4-dichlorophenyl, 2-chloro-4-fluorophenyl, 2,4,5-trifluorophenyl, 1,3-benzodioxolyl and 2,3-dihydro-1,4-benzodioxin-6-yl.

The term "cyano" as used herein, means —CN.

The term "cyanoalkyl" as used herein, means an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, means a monocyclic or bicyclic cycloalkyl. The monocyclic cycloalkyl has three to eight carbon atoms, zero heteroatoms and zero double bonds. The monocyclic cycloalkyl can be attached to the parent molecular moiety through any substitutable atom contained within the monocyclic cycloalkyl. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl. The bicyclic cycloalkyl can be attached to the parent molecular moiety through any substitutable atom contained within the bicyclic cycloalkyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system containing at least one double bond. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The bicyclic cycloalkenyl can be attached to the parent molecular moiety through any substitutable atom contained within the bicyclic cycloalkenyl. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "ethylenedioxy" as used herein, means a —O—(CH$_2$)$_2$—O— group wherein the oxygen atoms of the ethylenedioxy group are attached to two adjacent carbon atoms of the parent molecular moiety, forming a six membered ring with the parent molecular moiety.

The term "halo" or "halogen" as used herein, means —Cl, —Br, —I or —F.

The term "haloalkoxy" as used herein, means an alkoxy group, as defined herein, in which one, two, three or four hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkoxyalkyl" as used herein, means a haloalkoxy group, as defined herein, appended to the parent moiety through an alkyl group, as defined herein.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, means a monocyclic heterocycle, or a bicyclic heterocycle, or a tricyclic heterocycle. The monocyclic heterocycle is a three-, four-, five-, six- or seven-membered ring containing at least one heteroatom independently selected from the group consisting of O, N, and S. The three- or four-membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two or three double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, 1,3-thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle, or a monocyclic heterocycle fused to a monocyclic heteroaryl. The bicyclic heterocycle is connected to the parent molecular moiety through any carbon atom or any nitrogen atom contained within the bicyclic heterocycle. Representative examples of bicyclic heterocycle include, but are not limited to, 1,3-benzodithiolyl, benzopyranyl, benzothiopyranyl, 2,3-dihydrobenzofuranyl, 2,3-dihydrobenzothienyl, 2,3-dihydro-1H-indolyl, 2,3-dihydroisoindol-2-yl, 2,3-dihydroisoindol-3-yl, 1,3-dioxo-1H-isoindolyl, 5,6-dihydroimidazo-[1,2-a]pyrazin-7(8H)-yl, 1-acetyl-2,3-dihydro-1H-indol-6-yl, 5,6-dihydro[1,2,4]triazolo[4,3-a]pyrazin-7(8H)-yl, 1,2,3,4-tetrahydroisoquinolin-2-yl, and 1,2,3,4-tetrahydroquinolinyl. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle fused to a monocyclic heteroaryl. The tricyclic heterocycle is connected to the parent molecular moiety through any carbon atom or any nitrogen atom contained within the tricyclic heterocycle. Representative examples of tricyclic heterocycle include, but are not limited to, 6,8-dihydrofuro[3,4-g][1,3]benzothiazol-2-yl, 6,8-dihydrofuro[3,4-g][1,3]benzoxazol-2-yl, 8-oxo-6,8-dihydrofuro[3,4-g][1,3]benzothiazol-2-yl, and 8-oxo-6,8-dihydrofuro[3,4-g][1,3]benzoxazol-2-yl. The monocyclic, bicyclic, and tricyclic heterocycle of the present invention can be unsubstituted or substituted. Examples of substituted heterocycle include, but are not limited to, 3-(trifluoromethyl)-5,6-dihydro[1,2,4]triazolo[4,3-a]pyrazin-7(8H)-yl and 2-(trifluoromethyl)-5,6-dihydroimidazo-[1,2-a]pyrazin-7(8H)-yl.

The term "heterocyclealkyl" as used herein, means a monocyclic or bicyclic heterocycle, as defined herein, appended to the parent molecular moiety through an alkyl group, as defined herein. Representative examples of heterocyclealkyl include, but are not limited to, piperidin-1-ylmethyl, 7,8-dihydro[1,3]dioxolo[4,5-g]isoquinolin-6(5H)-yl-methyl, 1,2,3,4-tetrahydroisoquinolinylmethyl, (piperazin-1-yl)methyl, (pyridin-3-yl)methyl, pyrrolinylmethyl, [5,6-dihydroimidazol[1,2,a]pyrazin-7(8H)-yl]methyl, and 2-(pyrimidin-2-yl)propyl. The heterocyclealkyl can be substituted or unsubstituted.

The term "heteroaryl" as used herein, means a monocyclic heteroaryl, or a bicyclic heteroaryl, or a tricyclic heteroaryl. The monocyclic heteroaryl is a five- or six-membered ring. The five-membered ring consists of two double bonds, and one, two, three or four nitrogen atoms and optionally one oxygen or sulfur atom. The six-membered ring consists of three double bonds and one, two, three or four nitrogen atoms. The monocyclic heteroaryl is connected to the parent molecular moiety through any substitutable atom contained within the monocyclic heteroaryl. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl groups include, but not limited to, benzofuranyl, benzothienyl, 1,3-benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, [1,3]thiazolo[5,4-b]pyridin-2-yl, [1,3]oxazolo[5,4-b]pyridin-2-yl, [1,3]thiazolo[4,5-b]pyridin-2-yl, [1,3]oxazolo[4,5-b]pyridin-2-yl, [1,3]thiazolo[5,4-d]pyrimidin-2-yl, [1,3]oxazolo[5,4-d]pyrimidin-2-yl and 5,6,7,8-tetrahydroquinolin-5-yl. The tricyclic heteroaryl is a bicyclic heteroaryl fused to a phenyl, or a bicyclic heteroaryl fused to a monocyclic cycloalkyl, or a bicyclic heteroaryl fused to a monocyclic cycloalkenyl, or a bicyclic heteroaryl fused to a monocyclic heteroaryl. The tricyclic heteroaryl is connected to the parent molecular moiety through any carbon atom or any nitrogen atom contained within the tricyclic heteroaryl. Representative examples of tricyclic heteroaryl include, but are not limited to, [1,3]thiazolo[5,4,h]quinolin-2-yl, [1,3]oxazolo[5,4,h]quinolin-2-yl, naphtho[1,2-d][1,3]oxazol-2-yl, naphtho[1,2-d][1,3]thiazol-2-yl naphtho[2,3-d][1,3]oxazol-2-yl, and naphtho[2,3-d][1,3]thiazol-2-yl. The monocyclic, bicyclic and tricyclic heteroaryl groups of the present invention can be substituted or unsubstituted.

The term "heteroatom" as used herein, refers to nitrogen, oxygen or sulfur atom.

The term "hydroxy" or "hydroxyl" as used herein, means an —OH group.

The term "hydroxyalkyl" as used herein, means an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "methylenedioxy" as used herein, means a —O—(CH$_2$)—O— group wherein the oxygen atoms of the methylenedioxy group are attached to two adjacent carbon atoms of the parent molecular moiety, forming a five membered ring with the parent molecular moiety.

The term "nitro" as used herein, refers to an —NO$_2$ group.

The term "nitroalkyl" as used herein, means a nitro group, as defined herein, appended to the parent moiety through an alkyl group, as defined herein.

The term "oxo" as used herein, means =O.

The term "substituted" as used herein means being substituted with a substituent selected from, but not limited to, alkyl, alkenyl, —CN, —NO$_2$, halo, ethylenedioxy, methylenedioxy, oxo, OR$_a$, —OC(O)alkyl, —OC(O)Oalkyl, —OS(O)$_2$alkyl, —S(alkyl), —S(O)alkyl, —S(O)$_2$alkyl, —S(O)$_2$OR$_a$, —S(O)$_2$NR$_a$R$_b$, —C(O)R$_a$, —C(O)OR$_a$, —C(O) NR$_a$R$_b$, —NR$_a$R$_b$, —NOR$_a$, N(R$_b$)C(O)R$_a$, —N(R$_b$)C(O) OR$_a$, —N(R$_b$)S(O)$_2$R$_a$, —N(R$_b$)C(O)NR$_a$R$_b$, —N(R$_b$)S(O)$_2$ NR$_a$R$_b$, haloalkyl, cyanoalkyl, nitroalkyl, hydroxyalkyl, alkoxyalkyl, haloalkoxyalkyl, -alkylenyl-OC(O)alkyl, -alkylenyl-OC(O)Oalkyl, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)OR$_a$, -alkylenyl-C(O)NR$_a$R$_b$, -alkylenyl-NR$_a$R$_b$, -alkylenyl-NOR$_a$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$. Further, R$_a$ at each occurrence can be independently selected from the group including, but not limited to, hydrogen, alkyl, alkenyl and haloalkyl, R$_b$ at each occurrence can be independently selected from the group including, but not limited to, hydrogen and alkyl. Alternatively, the substituent can be, but is not limited to, R$_7$, alkyl, alkenyl, —CN, —NO$_2$, halo, ethylenedioxy, methylenedioxy, oxo, —OR$_{7A}$, —OC(O)R$_{7A}$, —OC(O)OR$_{7A}$, —OS(O)$_2$R$_{7A}$, —S(alkyl), —S(O)alkyl, —S(O)$_2$R$_{7A}$, —S(O)$_2$OR$_{7A}$, —S(O)$_2$NR$_{7A}$R$_b$, —C(O)R$_{7A}$, —C(O)OR$_{7A}$, —C(O)NR$_{7A}$R$_b$, —NR$_{7A}$R$_b$, —NOR$_{7A}$, —N(R$_b$)C(O)R$_{7A}$, —N(R$_b$)C(O)OR$_{7A}$, —N(R$_b$)S(O)$_2$R$_{7A}$, —N(R$_b$)C(O)NR$_{7A}$R$_b$, —N(R$_b$)S(O)$_2$NR$_{7A}$R$_b$, haloalkyl, cyanoalkyl, nitroalkyl, -alkylenyl-OR$_{7A}$, -alkylenyl-OC(O) R$_{7A}$, -alkylenyl-OC(O)OR$_{7A}$, -alkylenyl-OS(O)$_2$R$_{7A}$, -alkylenyl-S(alkyl), -alkylenyl-S(O)alkyl, -alkylenyl-S(O)$_2$R$_{7A}$, -alkylenyl-S(O)$_2$OR$_{7A}$, -alkylenyl-S(O)$_2$NR$_{7A}$R$_b$, -alkylenyl-C(O)R$_{7A}$, -alkylenyl-C(O)OR$_{7A}$, -alkylenyl-C(O) NR$_{7A}$R$_b$, -alkylenyl-NR$_{7A}$R$_b$, -alkylenyl-NOR$_{7A}$, -alkylenyl-N(R$_b$)C(O)R$_{7A}$, -alkylenyl-N(R$_b$)C(O)OR$_{7A}$, -alkylenyl-N(R$_b$)S(O)$_2$R$_{7A}$, -alkylenyl-N(R$_b$)C(O)NR$_{7A}$R$_b$, -alkylenyl-N(R$_b$)S(O)$_2$NR$_{7A}$R$_b$ and -alkylenyl-R$_7$. Moreover, R$_{7A}$ at each occurrence is independently selected from, but not limited to, hydrogen, alkyl, alkenyl, haloalkyl, —R$_7$ and -alkylenyl-R$_7$. Additionally, R$_7$ at each occurrence is independently selected from, but not limited to, aryl, heteroaryl, cycloalkyl, cycloalkenyl and heterocycle.

Compounds of the invention can have the formula (I) as described above. In compounds of formula (I), Ar$_1$ is selected from the group consisting of aryl and heteroaryl, each of which is unsubstituted or substituted as described in formula (I). Particularly, Ar$_1$ is unsubstituted or substituted aryl. More particularly, Ar$_1$ is unsubstituted or substituted phenyl. Even more particularly, Ar$_1$ is phenyl, unsubstituted or substituted with 1, 2, or 3 substituents selected from the group consisting of I, Cl, Br, and F. Preferably, Ar$_1$ is 2-chlorophenyl, 2,4-dichlorophenyl, 2-chloro-4-fluorophenyl, or 2,4,5-trifluorophenyl.

R$_1$ is selected from the group consisting of hydrogen, alkyl, haloalkyl, aryl, heteroaryl, heterocycle, cycloalkyl and cycloalkenyl; and R$_2$ is selected from the group consisting of hydrogen, alkyl, haloalkyl, cycloalkyl, heterocycle, aryl, heteroaryl, heterocyclealkyl, -alkylenyl-OR$_4$, -alkylenyl-O-alkylenyl-R$_4$, -alkylenyl-NR$_5$R$_6$, and —C(O)G; or R$_1$ is selected from the group consisting of hydrogen, alkyl, haloalkyl, cycloalkyl, heterocycle, aryl, heteroaryl, heterocyclealkyl, -alkylenyl-OR$_4$, -alkylenyl-O-alkylenyl-R$_4$, -alkylenyl-NR$_5$R$_6$, and —C(O)G, and R$_2$ is selected from the group consisting of hydrogen, alkyl, haloalkyl, aryl, heteroaryl, heterocycle, cycloalkyl and cycloalkenyl; wherein R$_4$, R$_5$, R$_6$ and G are as described in formula (I), and the aryl, heteroaryl, heterocycle, cycloalkyl, cycloalkenyl and the heterocycle moiety of the heterocycle as represented by R$_1$ and R$_2$ are each independently unsubstituted or substituted with substituents as described in formula (I). Preferably, R$_1$ is selected from the group consisting of hydrogen, unsubstituted or substituted aryl, and unsubstituted or substituted heteroaryl, and R$_2$ is selected from the group consisting of hydrogen, unsubstituted or substituted aryl, -alkylenyl-OR$_4$, -alkylenyl-NR$_5$R$_6$, unsubstituted or substituted heteroaryl, unsubstituted or substituted heteroaryl, —C(O)G, unsubstituted or substituted heterocyclealkyl, and unsubstituted or substituted heterocycle.

In one embodiment, R$_1$ and R$_2$ are each selected from the group of hydrogen.

In another embodiment, R$_1$ is hydrogen and R$_2$ is unsubstituted or substituted aryl.

In another embodiment, R$_1$ is unsubstituted or substituted aryl and R$_2$ is hydrogen.

In another embodiment, R$_1$ is hydrogen and R$_2$ is unsubstituted or substituted heteroaryl.

In another embodiment, R$_1$ is hydrogen and R$_2$ is unsubstituted or substituted heterocycle.

In another embodiment, R$_1$ is unsubstituted or substituted heteroaryl and R$_2$ is hydrogen.

In another embodiment, R$_1$ is hydrogen, unsubstituted or substituted aryl, or unsubstituted or substituted heteroaryl; and R$_2$ is -alkylenyl-OR$_4$. Suitably, R$_2$ is hydrogen or —CH$_2$—OR$_4$ wherein R$_4$ is unsubstituted or substituted aryl or unsubstituted or substituted heteroaryl.

In another embodiment, R$_1$ is hydrogen and R$_2$ is -alkylenyl-NR$_5$R$_6$ wherein R$_5$ is selected from the group consisting of hydrogen, alkyl and haloalkyl, and R$_6$ is selected from the group consisting of R$_4$, -alkylenyl-R$_4$, and —C(O)R$_4$. Suitably, R$_1$ is hydrogen and R$_2$ is —CH$_2$—NR$_5$R$_6$, wherein R$_5$ is hydrogen, and R$_6$ is selected from the group consisting of R$_4$, —CH$_2$—R$_4$, and —C(O)R$_4$, wherein R$_4$ is selected from the group consisting of aryl, heterocycle and heteroaryl, each of which is independently unsubstituted or substituted.

In another embodiment, R$_1$ is hydrogen and R$_2$ is —C(O)G wherein G is as described herein. Suitably, G is selected from the group consisting of R$_4$, —NR$_5$R$_4$, and N(R$_5$)(-alkylenyl-R$_4$) wherein R$_4$ and R$_5$ are as described herein. Preferably, G is R$_4$, —NR$_5$R$_4$, and N(R$_5$)(—CH$_2$—R$_4$). R$_5$ is selected from the group consisting of hydrogen, alkyl and haloalkyl, and R$_4$ is selected from the group consisting of aryl, heterocycle and heteroaryl, each of which is independently unsubstituted or substituted. Preferably, R$_5$ is selected from the group consisting of hydrogen, C$_1$-C$_6$ alkyl, and haloalkyl. More preferably, R$_5$ is selected from the group consisting of hydrogen, methyl, ethyl, n-propyl, 1-propyl, n-butyl, and trifluoromethyl. Most preferably, R$_5$ is hydrogen.

In another embodiment, R$_1$ is hydrogen and R$_2$ is heterocyclealkyl. Preferably, R$_1$ is hydrogen and R$_2$ is —CH$_2$-heterocycle wherein the heterocycle moiety is unsubstituted or substituted.

R$_3$ is selected from the group consisting of hydrogen, alkyl and haloalkyl. Preferably, R$_3$ is hydrogen.

It is appreciated that the present invention contemplates compounds of formula (I) with combinations of the above embodiments, including preferred, more preferred and most preferred embodiments.

Accordingly, one aspect of the invention is related to compounds of formula (I) wherein Ar$_1$ is unsubstituted or substituted aryl with substituents as described herein; R$_1$ is selected from the group consisting of hydrogen, alkyl, haloalkyl, aryl, heteroaryl, heterocycle, cycloalkyl, and cycloalkenyl; and R$_2$ is selected from the group consisting of hydrogen, alkyl, haloalkyl, cycloalkyl, heterocycle, aryl, heteroaryl, heterocyclealkyl, -alkylenyl-OR$_4$, -alkylenyl-O-alkylenyl-R$_4$, -alkylenyl-NR$_5$R$_6$ and —C(O)G, wherein each of the aryl, heteroaryl, heterocycle, cycloalkyl, cycloalkenyl, and the heterocycle moiety of the heterocyclealkyl is independently unsubstituted or substituted with substituents as described in formula (I), and wherein R$_4$, R$_5$, R$_6$ and G are as described in formula (I).

Another aspect of the invention is related to compounds of formula (I) wherein Ar$_1$ is unsubstituted or substituted phenyl; R$_1$ is hydrogen, and R$_2$ is selected from the group consisting of hydrogen, aryl, heteroaryl, heterocycle, heterocyclealkyl, -alkylenyl-OR$_4$, -alkylenyl-NR$_5$R$_6$ and —C(O)G, wherein each of the aryl, heteroaryl, heterocycle, and the heterocycle moiety of the heterocyclealkyl is independently unsubstituted or substituted with substituents as described in formula (I), and wherein R$_4$, R$_5$, R$_6$ and G are as described in formula (I).

One embodiment of the compounds of the invention is that of formula (II)

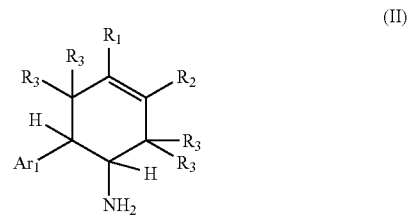

(II)

or a pharmaceutically acceptable salt, metabolite, prodrug, salt of a prodrug, or a combination thereof, wherein Ar$_1$, R$_1$, R$_2$ and R$_3$ are as previously described. It is understood that embodiments of Ar$_1$, R$_1$, R$_2$ and R$_3$ and combinations of embodiments, including preferred, more preferred and most preferred embodiments as described in formula (I) are also contemplated for compounds of formula (II).

Accordingly, one aspect of the invention relates to compounds of formula (II) wherein Ar$_1$ is unsubstituted or substituted aryl, R$_1$ is selected from the group consisting of hydrogen, unsubstituted or substituted aryl and unsubstituted or substituted heteroaryl, and R$_2$ is selected from the group consisting of hydrogen, aryl, heteroaryl, heterocycle, heterocyclealkyl, -alkylenyl-OR$_4$, -alkylenyl-NR$_5$R$_6$ and —C(O)G; wherein R$_4$, R$_5$, R$_6$ and G are as described in formula (I) and each of the aryl, heteroaryl, heterocycle, and heterocycle moiety of the heterocyclealkyl is independently unsubstituted or substituted.

Another aspect of the invention relates to compounds of formula (II) wherein Ar$_1$ is unsubstituted or substituted phenyl; R$_1$ is selected from the group consisting of hydrogen, unsubstituted or substituted aryl and unsubstituted or substituted heteroaryl, and R$_2$ is selected from the group consisting of hydrogen, aryl, heteroaryl, heterocycle, heterocyclealkyl, —CH$_2$—OR$_4$, —CH$_2$—NR$_5$R$_6$ (and —C(O)G; wherein R$_4$, R$_5$, R$_6$ and G are as described in formula (I) and each of the aryl, heteroaryl, heterocycle, and heterocycle moiety of the heterocyclealkyl is independently unsubstituted or substituted.

Another aspect of the invention relates to compounds of formula (II) wherein Ar$_1$ is phenyl, unsubstituted or substituted with 1, 2 or 3 substituents selected from the group consisting of —I, —Br, —Cl, and —F; R$_1$ is selected from the group consisting of hydrogen, aryl and heteroaryl, and R$_2$ is selected from the group consisting of hydrogen, aryl, heteroaryl, heterocycle, —CH$_2$-heterocycle, —CH$_2$—OR$_4$, —CH$_2$—NR$_5$R$_6$ and —C(O)G; wherein R$_4$, R$_5$, R$_6$ and G are as described in formula (I) and each of the aryl, heteroaryl, heterocycle, and heterocycle moiety of the heterocyclealkyl is independently unsubstituted or substituted.

Another aspect of the invention relates to compounds of formula (II) wherein Ar$_1$ is 2-chlorophenyl, 2,4-dichlorophenyl, 2-chloro-4-fluorophenyl or 2,4,5-trifluorophenyl; R$_1$ is selected from the group consisting of hydrogen, aryl and heteroaryl, and $R_2$ is selected from the group consisting of hydrogen, aryl, heteroaryl, heterocycle, —$CH_2$-heterocycle, —$CH_2$—$OR_4$, —$CH_2$—$NR_5R_6$ and —C(O)G; wherein $R_4$, $R_5$, $R_6$ and G are as described in formula (I) and each of the aryl, heteroaryl, heterocycle, and heterocycle moiety of the heterocyclealkyl is independently unsubstituted or substituted.

Another aspect of the invention relates to compounds of formula (II) wherein $Ar_1$ is unsubstituted or substituted aryl, $R_1$ is selected from the group consisting of hydrogen and unsubstituted or substituted aryl, and $R_2$ is selected from the group consisting of hydrogen and unsubstituted or substituted aryl.

Another aspect of the invention relates to compounds of formula (II) wherein $Ar_1$ is unsubstituted or substituted phenyl, $R_1$ is selected from the group consisting of hydrogen, unsubstituted or substituted phenyl, and unsubstituted or substituted naphthyl, and $R_2$ is selected from the group consisting of hydrogen, unsubstituted and substituted phenyl and unsubstituted or substituted naphthyl.

Another aspect of the invention relates to compounds of formula (II) wherein $Ar_1$ is unsubstituted or substituted phenyl, $R_1$ is selected from the group consisting of hydrogen, unsubstituted and substituted phenyl, and $R_2$ is selected from the group consisting of hydrogen, unsubstituted and substituted phenyl.

Another aspect of the invention relates to compounds of formula (II) wherein $Ar_1$ is phenyl, unsubstituted or substituted with 1, 2, or 3 substituents selected from the group consisting of —I, —Br, —Cl, and —F; $R_1$ is selected from the group consisting of hydrogen, unsubstituted and substituted phenyl, and $R_2$ is selected from the group consisting of hydrogen, unsubstituted and substituted phenyl.

Another aspect of the invention relates to compounds of formula (II) wherein $Ar_1$ is 2-chlorophenyl, 2,4-dichlorophenyl, 2-chloro-4-fluorophenyl, or 2,4,5-trifluorophenyl; $R_1$ is selected from the group consisting of hydrogen, unsubstituted and substituted phenyl, and $R_2$ is selected from the group consisting of hydrogen, unsubstituted and substituted phenyl.

Another aspect of the invention relates to compounds of formula (II) wherein $Ar_1$ is aryl, $R_1$ is selected from the group consisting of hydrogen, aryl and heteroaryl, and $R_2$ is -alkylenyl-$OR_4$.

Another aspect of the invention relates to compounds of formula (II) wherein $Ar_1$ is unsubstituted or substituted phenyl, $R_1$ is selected from the group consisting of hydrogen and an unsubstituted or substituted ring selected from the group consisting of phenyl, naphthyl, pyridinyl, pyrimidinyl, pyrazinyl, pyrrolyl, thienyl, furanyl, isoxazolyl, thiazolyl, oxazolyl, and imidazolyl; and $R_2$ is —$CH_2$—$OR_4$ wherein $R_4$ is an unsubstituted or substituted ring selected from the group consisting of phenyl, naphthyl, pyridinyl, pyrimidinyl, pyrazinyl, pyrrolyl, thienyl, furanyl, isoxazolyl, thiazolyl, oxazolyl, and imidazolyl; wherein each of the rings as represented by $R_1$ and $R_4$ is independently unsubstituted or substituted.

Another aspect of the invention relates to compounds of formula (II) wherein $Ar_1$ is unsubstituted or substituted phenyl, $R_1$ is selected from the group consisting of hydrogen, phenyl and pyridinyl, and $R_2$ is —$CH_2$—$OR_4$ wherein $R_4$ is selected from the group consisting of phenyl and pyridinyl; wherein each of the phenyl and pyridinyl as represented by $R_1$ and $R_4$ is independently unsubstituted or substituted.

Another aspect of the invention relates to compounds of formula (II) wherein $Ar_1$ is phenyl, unsubstituted or substituted with 1, 2, or 3 substituents selected from the group consisting of —I, —Br, l, and I; $R_1$ is selected from the group consisting of hydrogen, phenyl and pyridinyl, and $R_2$ is —$CH_2$—$OR_4$ wherein $R_4$ is selected from the group consisting of phenyl and pyridinyl; wherein each of the phenyl and pyridinyl as represented by $R_1$ and $R_4$ is independently unsubstituted or substituted.

Another aspect of the invention relates to compounds of formula (II) wherein $Ar_1$ is unsubstituted or substituted aryl, $R_1$ is hydrogen, and $R_2$ is heterocyclealkyl wherein the heterocycle moiety of the heterocycle is unsubstituted or substituted.

Another aspect of the invention relates to compounds of formula (II) wherein $Ar_1$ is unsubstituted or substituted aryl, $R_1$ is hydrogen, and $R_2$ is —$CH_2$-heterocycle wherein the heterocycle moiety of the —$CH_2$-heterocycle is unsubstituted or substituted.

Another aspect of the invention relates to compounds of formula (II) wherein $Ar_1$ is unsubstituted or substituted phenyl, $R_1$ is hydrogen, and $R_2$ is —$CH_2$-heterocycle wherein the heterocycle moiety of the —$CH_2$-heterocycle is an unsubstituted or substituted ring selected from the group consisting of piperidinyl, pyrrolidinyl, 5,6-dihydro[1,2,4]triazolo[4,3-a]pyrazin-7(8H)-yl, piperazinyl, 1,2,3,4-tetrahydroisoquinolin-2-yl, 1,2,3,4-tetrahydroisoquinolinyl, morpholinyl, 1,3-thiazolidinyl, 5,6-dihydroimidazo[1,2-a]pyrazin-7(8H)-yl, 2,3-dihydro-1H-indolyl, and 1,3-dihydroisoindol-2-yl.

Another aspect of the invention relates to compounds of formula (II) wherein $Ar_1$ is unsubstituted or substituted phenyl, $R_1$ is hydrogen, and $R_2$ is heterocyclealkyl wherein the heterocycle moiety of the heterocyclealkyl is an unsubstituted or substituted ring selected from the group consisting of piperidinyl, 5,6-dihydro[1,2,4]triazolo[4,3-a]pyrazin-7(8H)-yl, piperazinyl, 1,2,3,4-tetrahydroisoquinolin-2-yl, 5,6-dihydroimidazo[1,2-a]pyrazin-7(8H)-yl, pyrrolidinyl, and 1,3-dihydroisoindol-2-yl.

Another aspect of the invention relates to compounds of formula (II) wherein $Ar_1$ is phenyl, unsubstituted or substituted with 1, 2, or 3 substituents selected from the group consisting of —I, —Br, —Cl and —F; $R_1$ is hydrogen, and $R_2$ is —$CH_2$-heterocycle wherein the heterocycle moiety of the —$CH_2$-heterocycle is an unsubstituted or substituted ring selected from the group consisting of piperidinyl, 5,6-dihydro[1,2,4]triazolo[4,3-a]pyrazin-7(8H)-yl, piperazinyl, 1,2,3,4-tetrahydroisoquinolin-2-yl, 5,6-dihydroimidazo[1,2-a]pyrazin-7(8H)-yl, pyrrolidinyl, and 1,3-dihydroisoindol-2-yl.

Another aspect of the invention relates to compounds of formula (II) wherein $Ar_1$ is unsubstituted or substituted aryl, $R_1$ is hydrogen, and $R_2$ is —C(O)G wherein G is —$NR_5R_4$ or —$N(R_5)$(-alkylenyl-$R_4$) wherein $R_4$ is selected from the group consisting of aryl and heteroaryl.

Another aspect of the invention relates to compounds of formula (II) wherein $Ar_1$ is unsubstituted or substituted aryl, $R_1$ is hydrogen, and $R_2$ is —C(O)G wherein G is —$NR_5R_4$ or —$N(R_5)$(—$CH_2$—$R_4$) wherein —$R_5$ is selected from the group consisting of hydrogen, $C_1$-$C_6$ alkyl and haloalkyl; and $R_4$ is selected from the group consisting of aryl and heteroaryl, each of which is independently unsubstituted or substituted.

Another aspect of the invention relates to compounds of formula (II) wherein $Ar_1$ is unsubstituted or substituted phenyl, $R_1$ is hydrogen, and $R_2$ is —C(O)G wherein G is —$NR_5R_4$ or —$N(R_5)$(—$CH_2$—$R_4$); wherein —$R_5$ is selected from the group consisting of hydrogen, $C_1$-$C_6$ alkyl and haloalkyl; $R_4$ is an unsubstituted or substituted ring selected from the group consisting of phenyl, naphthyl, pyridinyl, pyrimidinyl, pyrazinyl, pyrrolyl, thienyl, furanyl, isoxazolyl, thiazolyl, oxazolyl, and imidazolyl.

Another aspect of the invention relates to compounds of formula (II) wherein $Ar_1$ is unsubstituted or substituted phenyl, $R_1$ is hydrogen, and $R_2$ is —C(O)G wherein G is —$NR_5R_4$ or —$N(R_5)$(—$CH_2$—$R_4$); wherein —$R_5$ is selected from the group consisting of hydrogen, $C_1$-$C_6$ alkyl, and haloalkyl; $R_4$ is an unsubstituted or substituted ring selected from the group consisting of phenyl and pyridinyl.

Another aspect of the invention relates to compounds of formula (II) wherein $Ar_1$ is phenyl, unsubstituted or substituted with 1, 2, or 3 substituents selected from the group consisting of —I, —Br, —Cl, and —F; $R_1$ is hydrogen, and $R_2$ is —C(O)G wherein G is —$NR_5R_4$ or —$N(R_5)$(—$CH_2$—$R_4$); wherein —$R_5$ is hydrogen, methyl, ethyl, isopropyl or n-propyl; $R_4$ is an unsubstituted or substituted ring selected from the group consisting of phenyl and pyridinyl.

Another aspect of the invention relates to compounds of formula (II) wherein $Ar_1$ is unsubstituted or substituted aryl, $R_1$ is hydrogen, and $R_2$ is —C(O)G wherein G is $R_4$.

Another aspect of the invention relates to compounds of formula (II) wherein $Ar_1$ is unsubstituted or substituted aryl, $R_1$ is hydrogen, and $R_2$ is —C(O)G wherein G is heterocycle.

Another aspect of the invention relates to compounds of formula (II) wherein $Ar_1$ is unsubstituted or substituted phenyl, $R_1$ is hydrogen, and $R_2$ is —C(O)G wherein G is an unsubstituted or substituted heterocycle ring selected from the group consisting of piperidinyl, pyrrolidinyl, 5,6-dihydro[1,2,4]triazolo[4,3-a]pyrazin-7(8H)-yl, piperazinyl, 1,2,3,4-tetrahydroisoquinolin-2-yl, 1,2,3,4-tetrahydroquinolinyl, morpholinyl, 1,3-thiazolidinyl, 5,6-dihydroimidazo[1,2-a]pyrazin-7(8H)-yl, pyrrolidinyl, 2,3-dihydro-1H-indolyl, and 1,3-dihydroisoindol-2-yl.

Another aspect of the invention relates to compounds of formula (II) wherein $Ar_1$ is unsubstituted or substituted phenyl, $R_1$ is hydrogen, and $R_2$ is —C(O)G wherein G is an unsubstituted or substituted heterocycle ring selected from the group consisting of piperidinyl, pyrrolidinyl, 1,2,3,4-tetrahydroisoquinolin-2-yl, 5,6-dihydroimidazo[1,2-a]pyrazin-7(8H)-yl, 5,6-dihydro[1,2,4]triazolo[4,3-a]pyrazin-7(8H)-yl, piperazinyl, morpholinyl, and 1,3-thiazolidin-3-yl.

Another aspect of the invention relates to compounds of formula (II) wherein $Ar_1$ is phenyl, unsubstituted or substituted with 1, 2, or 3 substituents selected from the group consisting of —I, —Br, —Cl, and —F; $R_1$ is hydrogen, and $R_2$ is —C(O)G wherein G is an unsubstituted or substituted heterocycle ring selected from the group consisting of piperidinyl, pyrrolidinyl, 1,2,3,4-tetrahydroisoquinolin-2-yl, 5,6-dihydroimidazo[1,2-a]pyrazin-7(8H)-yl, 5,6-dihydro[1,2,4]triazolo[4,3-a]pyrazin-7(8H)-yl, piperazinyl, morpholinyl, and 1,3-thiazolidin-3-yl.

Another aspect of the invention relates to compounds of formula (II) wherein $Ar_1$ is unsubstituted or substituted aryl, $R_1$ is hydrogen, and $R_2$ is -alkylenyl-$NR_5R_6$; wherein $R_5$ is selected from the group consisting of hydrogen, alkyl and haloalkyl, and $R_6$ is selected from the group consisting of $R_4$, -alkylenyl-$R_4$, and —C(O)$R_4$; wherein $R_4$ is selected from an unsubstituted or substituted ring consisting of aryl, heteroaryl and heterocycle.

Another aspect of the invention relates to compounds of formula (II) wherein $Ar_1$ is unsubstituted or substituted aryl, $R_1$ is hydrogen, and $R_2$ is —$CH_2$—$NR_5R_6$; wherein $R_5$ is selected from the group consisting of hydrogen, $C_1$-$C_6$ alkyl and halomethyl, and $R_6$ is selected from the group consisting of $R_4$, —$CH_2$—$R_4$, and —C(O)$R_4$; wherein $R_4$ is selected from an unsubstituted or substituted ring consisting of aryl, heteroaryl and heterocycle.

Another aspect of the invention relates to compounds of formula (II) wherein $Ar_1$ is unsubstituted or substituted phenyl, $R_1$ is hydrogen, and $R_2$ is —$CH_2$—$NR_5R_6$; wherein $R_5$ is selected from the group consisting of hydrogen, methyl, ethyl, propyl, isopropyl, n-butyl and trifluoromethyl; and $R_6$ is $R_4$, —$CH_2$—$R_4$, or —C(O)$R_4$; wherein $R_4$ is an unsubstituted or substituted ring selected from the group consisting of phenyl, naphthyl, pyridinyl, pyrimidinyl, pyrazinyl, pyrrolyl, thienyl, furanyl, isoxazolyl, thiazolyl, oxazolyl, imidazolyl, piperidinyl, pyrrolidinyl, 5,6-dihydro[1,2,4]triazolo[4,3-a]pyrazin-7(8H)-yl, piperazinyl, 1,2,3,4-tetrahydroisoquinolin-2-yl, 1,2,3,4-tetrahydroquinolinyl, morpholinyl, 1,3-thiazolidinyl, 5,6-dihydroimidazo[1,2-a]pyrazin-7(8H)-yl, pyrrolidinyl, 2,3-dihydro-1H-indolyl, and 1,3-dihydroisoindol-2-yl.

Another aspect of the invention relates to compounds of formula (II) wherein $Ar_1$ is unsubstituted or substituted phenyl, $R_1$ is hydrogen, and $R_2$ is —$CH_2$—$NR_5R_6$; wherein $R_5$ is hydrogen, and $R_6$ is $R_4$, —$CH_2$—$R_4$, or —C(O)$R_4$; wherein $R_4$ is an unsubstituted or substituted ring selected from the group consisting of phenyl, pyridinyl, 2,3-dihydro-(1H)-indol-6-yl, and pyrimidinyl.

Exemplary compounds of the present invention having formula (II) include, but are not limited to,
trans-6-(2-chlorophenyl)cyclohex-3-en-1-amine;
trans-6-(2,4-dichlorophenyl)cyclohex-3-en-1-amine;
trans-6-(2-chloro-4-fluorophenyl)cyclohex-3-en-1-amine;
trans-6-(2-chlorophenyl)-3-phenylcyclohex-3-en-1-amine compound;
trans-6-(2-chlorophenyl)-4-phenylcyclohex-3-en-1-amine;
trans-6-(2,4-dichlorophenyl)-3-phenylcyclohex-3-en-1-amine;
trans-6-(2,4-dichlorophenyl)-4-phenylcyclohex-3-en-1-amine;
trans-6-(2-chlorophenyl)-3-(4-methoxyphenyl)cyclohex-3-en-1-amine;
trans-6-(2-chlorophenyl)-4-(4-methoxyphenyl)cyclohex-3-en-1-amine;
4-{[trans-5-amino-4-(2,4-dichlorophenyl)-2-phenylcyclohex-1-en-1-yl]methoxy}benzonitrile;
4-{[trans-5-amino-4-(2,4-dichlorophenyl)-2-pyridin-3-ylcyclohex-1-en-1-yl]methoxy}benzonitrile;
trans-methyl 3-{[5-amino-4-(2,4-dichlorophenyl)-2-pyridin-3-ylcyclohex-1-en-1-yl]methoxy}benzoate;
trans-6-(2,4-dichlorophenyl)-4-pyridin-3-yl-3-[(pyridin-4-yloxy)methyl]cyclohex-3-en-1-amine;
3-{[trans-5-amino-4-(2,4-dichlorophenyl)-2-pyridin-3-ylcyclohex-1-en-1-yl]methoxy}benzoic acid;
trans-3-(phenoxymethyl)-6-(2,4,5-trifluorophenyl)cyclohex-3-en-1-amine;
trans-3-{[4-(methylsulfonyl)phenoxy]methyl}-6-(2,4,5-trifluorophenyl)cyclohex-3-en-1-amine;
3-{[trans-5-amino-4-(2,4,5-trifluorophenyl)cyclohex-1-en-1-yl]methoxy}benzamide;
4-{[trans-5-amino-4-(2,4,5-trifluorophenyl)cyclohex-1-en-1-yl]methoxy}benzamide;
N-(3-{[trans-5-amino-4-(2,4,5-trifluorophenyl)cyclohex-1-en-1-yl]methoxy}phenyl)-N,N-dimethylamine;
trans-3-[(1,3-benzodioxol-5-yloxy)methyl]-6-(2,4,5-trifluorophenyl)cyclohex-3-en-1-amine;
trans-3-{[2-(methylsulfonyl)phenoxy]methyl}-6-(2,4,5-trifluorophenyl)cyclohex-3-en-1-amine;
N-(3-{[trans-5-amino-4-(2,4,5-trifluorophenyl)cyclohex-1-en-1-yl]methoxy}phenyl)acetamide;
3-{[trans-5-amino-4-(2,4,5-trifluorophenyl)cyclohex-1-en-1-yl]methoxy}-4-fluorobenzoic acid;

trans-3-{[2-chloro-5-(trifluoromethyl)phenoxy]methyl}-6-(2,4,5-trifluorophenyl)cyclohex-3-en-1-amine;
trans-3-[(1-naphthyloxy)methyl]-6-(2,4,5-trifluorophenyl)cyclohex-3-en-1-amine;
1-{[trans-5-amino-4-(2,4-dichlorophenyl)cyclohex-1-en-1-yl]methyl}piperidine-4-carboxylic acid;
1-{[trans-5-amino-4-(2,4-dichlorophenyl)cyclohex-1-en-1-yl]methyl}piperidin-4-ol;
(3S)-1-{[trans-5-amino-4-(2,4-dichlorophenyl)cyclohex-1-en-1-yl]methyl}piperidine-3-carboxylic acid;
(3R)-1-{[trans-5-amino-4-(2,4-dichlorophenyl)cyclohex-1-en-1-yl]methyl}piperidine-3-carboxylic acid;
trans-3-{[3-(trifluoromethyl)-5,6-dihydro[1,2,4]triazolo[4,3-a]pyrazin-7(8H)-yl]methyl}-6-(2,4,5-trifluorophenyl)cyclohex-3-en-1-amine;
trans-3-[(4-acetylpiperazin-1-yl)methyl]-6-(2,4,5-trifluorophenyl)cyclohex-3-en-1-amine;
trans-3-(3,4-dihydroisoquinolin-2(1H)-ylmethyl)-6-(2,4,5-trifluorophenyl)cyclohex-3-en-1-amine;
ethyl 4-{[trans-5-amino-4-(2,4,5-trifluorophenyl)cyclohex-1-en-1-yl]methyl}piperazine-1-carboxylate;
trans-3-{[2-(trifluoromethyl)-5,6-dihydroimidazo[1,2-a]pyrazin-7(8H)-yl]methyl}-6-(2,4,5-trifluorophenyl)cyclohex-3-en-1-amine;
trans-3-[(4-phenylpiperazin-1-yl)methyl]-6-(2,4,5-trifluorophenyl)cyclohex-3-en-1-amine;
1-{[trans-5-amino-4-(2,4,5-trifluorophenyl)cyclohex-1-en-1-yl]methyl}piperidine-4-carboxamide;
trans-1-{[5-amino-4-(2,4,5-trifluorophenyl)cyclohex-1-en-1-yl]methyl}-L-prolinamide;
trans-3-(7,8-dihydro[1,3]dioxolo[4,5-g]isoquinolin-6(5H)-ylmethyl)-6-(2,4,5-trifluorophenyl)cyclohex-3-en-1-amine;
2-{[trans-5-amino-4-(2,4,5-trifluorophenyl)cyclohex-1-en-1-yl]methyl}-1,2,3,4-tetrahydroisoquinoline-7-carboxamide;
2-{[trans-5-amino-4-(2,4,5-trifluorophenyl)cyclohex-1-en-1-yl]methyl}-1,2,3,4-tetrahydroisoquinoline-7-carbonitrile;
2-{[trans-5-amino-4-(2,4,5-trifluorophenyl)cyclohex-1-en-1-yl]methyl}-1H-isoindole-1,3(2H)-dione;
trans-5-amino-N-phenyl-4-(2,4,5-trifluorophenyl)cyclohex-1-ene-1-carboxamide;
trans-5-amino-N-benzyl-4-(2,4,5-trifluorophenyl)cyclohex-1-ene-1-carboxamide;
4-({[trans-5-amino-4-(2,4,5-trifluorophenyl)cyclohex-1-en-1-yl]carbonyl}amino)benzamide;
3-({[trans-5-amino-4-(2,4,5-trifluorophenyl)cyclohex-1-en-1-yl]carbonyl}amino)benzamide;
trans-N-[3-(acetylamino)phenyl]-5-amino-4-(2,4,5-trifluorophenyl)cyclohex-1-ene-1-carboxamide;
trans-5-amino-N-1,3-benzodioxol-5-yl-4-(2,4,5-trifluorophenyl)cyclohex-1-ene-1-carboxamide;
6-({[trans-5-amino-4-(2,4,5-trifluorophenyl)cyclohex-1-en-1-yl]carbonyl}amino)nicotinamide;
3-({[trans-5-amino-4-(2,4,5-trifluorophenyl)cyclohex-1-en-1-yl]carbonyl}amino)-N-methylbenzamide;
3-({[trans-5-amino-4-(2,4,5-trifluorophenyl)cyclohex-1-en-1-yl]carbonyl}amino)-N,N-dimethylbenzamide;
2-{[trans-5-amino-4-(2,4,5-trifluorophenyl)cyclohex-1-en-1-yl]carbonyl}-1,2,3,4-tetrahydroisoquinoline-7-carboxamide;
1-{[trans-5-amino-4-(2,4,5-trifluorophenyl)cyclohex-1-en-1-yl]carbonyl}piperidine-4-carboxamide;
trans-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;
trans-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine;
trans-3-(piperidin-1-ylcarbonyl)-6-(2,4,5-trifluorophenyl)cyclohex-3-en-1-amine;
trans-3-(morpholin-4-ylcarbonyl)-6-(2,4,5-trifluorophenyl)cyclohex-3-en-1-amine;
(1R,6S)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;
(1S,6R)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;
trans-3-{[4-(1,3-benzodioxol-5-ylmethyl)piperazin-1-yl]carbonyl}-6-(2,4,5-trifluorophenyl)cyclohex-3-en-1-amine;
trans-3-(piperazin-1-ylcarbonyl)-6-(2,4,5-trifluorophenyl)cyclohex-3-en-1-amine;
(1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine;
(1S,6R)-3-(1,3-thiazolidin-3-ylcarbonyl)-6-(2,4,5-trifluorophenyl)cyclohex-3-en-1-amine;
(1S,6R)-3-(3,4-dihydroisoquinolin-2(1H)-ylcarbonyl)-6-(2,4,5-trifluorophenyl)cyclohex-3-en-1-amine;
N-{[trans-5-amino-4-(2,4-dichlorophenyl)cyclohex-1-en-1-yl]methyl}-3-chloro-4-(methylsulfonyl)thiophene-2-carboxamide;
N-{[trans-5-amino-4-(2,4-dichlorophenyl)cyclohex-1-en-1-yl]methyl}-5-bromonicotinamide;
4-[({[trans-5-amino-4-(2,4-dichlorophenyl)cyclohex-1-en-1-yl]methyl}amino)carbonyl]benzoic acid;
N-{[trans-5-amino-4-(2,4,5-trifluorophenyl)cyclohex-1-en-1-yl]methyl}-N-phenylamine;
4-({[trans-5-amino-4-(2,4,5-trifluorophenyl)cyclohex-1-en-1-yl]methyl}amino)benzamide;
N-{[trans-5-amino-4-(2,4,5-trifluorophenyl)cyclohex-1-en-1-yl]methyl}-N-benzylamine;
N-{[trans-5-amino-4-(2,4,5-trifluorophenyl)cyclohex-1-en-1-yl]methyl}pyridin-2-amine;
N-{[trans-5-amino-4-(2,4,5-trifluorophenyl)cyclohex-1-en-1-yl]methyl}-N-[4-(methylsulfonyl)phenyl]amine;
4-({[trans-5-amino-4-(2,4,5-trifluorophenyl)cyclohex-1-en-1-yl]methyl}amino)-N,N-dimethylbenzamide;
N-{[trans-5-amino-4-(2,4,5-trifluorophenyl)cyclohex-1-en-1-yl]methyl}-N-[2-(methylsulfonyl)phenyl]amine;
4-({[trans-5-amino-4-(2,4,5-trifluorophenyl)cyclohex-1-en-1-yl]methyl}amino)benzoic acid;
6-({[trans-5-amino-4-(2,4,5-trifluorophenyl)cyclohex-1-en-1-yl]methyl}amino)nicotinamide;
3-({[trans-5-amino-4-(2,4,5-trifluorophenyl)cyclohex-1-en-1-yl]methyl}amino)benzamide;
N-{[trans-5-amino-4-(2,4,5-trifluorophenyl)cyclohex-1-en-1-yl]methyl}-N-1,3-benzodioxol-5-ylamine;
N-{[trans-5-amino-4-(2,4,5-trifluorophenyl)cyclohex-1-en-1-yl]methyl}-N-2,3-dihydro-1,4-benzodioxin-6-ylamine;
2-({[trans-5-amino-4-(2,4,5-trifluorophenyl)cyclohex-1-en-1-yl]methyl}amino)benzamide;
3-({[trans-5-amino-4-(2,4,5-trifluorophenyl)cyclohex-1-en-1-yl]methyl}amino)-N-isopropylbenzamide;
3-({[trans-5-amino-4-(2,4,5-trifluorophenyl)cyclohex-1-en-1-yl]methyl}amino)benzoic acid;
N-[3-({[trans-5-amino-4-(2,4,5-trifluorophenyl)cyclohex-1-en-1-yl]methyl}amino)phenyl]acetamide;
1-acetyl-N-{[trans-5-amino-4-(2,4,5-trifluorophenyl)cyclohex-1-en-1-yl]methyl}indolin-6-amine;

1-[3-({[trans-5-amino-4-(2,4,5-trifluorophenyl)cyclohex-1-en-1-yl]methyl}amino)phenyl]ethanone;
3-({[trans-5-amino-4-(2,4,5-trifluorophenyl)cyclohex-1-en-1-yl]methyl}amino)-N-methylbenzamide;
[3-({[trans-5-amino-4-(2,4,5-trifluorophenyl)cyclohex-1-en-1-yl]methyl}amino)phenyl]acetic acid;
N-{[trans-5-amino-4-(2,4,5-trifluorophenyl)cyclohex-1-en-1-yl]methyl}-N-[3-methoxy-5-(trifluoromethyl)phenyl]amine;
3-({[trans-5-amino-4-(2,4,5-trifluorophenyl)cyclohex-1-en-1-yl]methyl}amino)benzonitrile;
N-{[trans-5-amino-4-(2,4,5-trifluorophenyl)cyclohex-1-en-1-yl]methyl}-N-(3-methylphenyl)amine;
N-{[trans-5-amino-4-(2,4,5-trifluorophenyl)cyclohex-1-en-1-yl]methyl}-N-(3-chlorophenyl)amine;
N-{[trans-5-amino-4-(2,4,5-trifluorophenyl)cyclohex-1-en-1-yl]methyl}-N-(3-fluorophenyl)amine;
N-{[trans-5-amino-4-(2,4,5-trifluorophenyl)cyclohex-1-en-1-yl]methyl}-6-thien-3-ylpyrimidin-4-amine
Methyl(4R,5S)-5-amino-4-(2,4,5-trifluorophenyl)cyclohex-1-enecarboxylate; and
(4R,5S)-[5-Amino-4-(2,4,5-trifluoro-phenyl)-cyclohex-1-enyl]-(2-trifluoromethyl-5,6-dihydro-8H-imidazo[1,2-a]pyrazin-7-yl)-methanone, tosylate salt;
or a pharmaceutically acceptable salt, metabolite, prodrug, salt of a prodrug, or a combination thereof.

Another aspect of the invention relates to compounds of formula (II) wherein $Ar_1$ is unsubstituted or substituted aryl, $R_1$ is hydrogen, and $R_2$ is an unsubstituted or substituted ring selected from the group consisting of heteroaryl and heterocycle.

Another aspect of the invention relates to compounds of formula (II) wherein $Ar_1$ is unsubstituted or substituted phenyl, $R_1$ is hydrogen, and $R_2$ is unsubstituted or substituted ring selected from the group consisting of 1,3-benzoxazol-2-yl, 1,3-benzothiazolyl, [1,3]thiazolo[5,4-b]pyridin-2-yl, [1,3]oxazolo[5,4-b]pyridin-2-yl, [1,3]thiazolo[4,5-b]pyridin-2-yl, [1,3]oxazolo[4,5-b]pyridin-2-yl, [1,3]thiazolo[5,4-d]pyrimidin-2-yl, [1,3]oxazolo[5,4-d]pyrimidin-2-yl, 6,8-dihydrofuro[3,4-g][1,3]benzothiazol-2-yl, 6,8-dihydrofuro[3,4-g][1,3]benzoxazol-2-yl, [1,3]thiazolo[5,4-h]quinolin-2-yl, [1,3]oxazolo[5,4-h]quinolin-2-yl, naphtho[1,2-d][1,3]oxazol-2-yl, naphtho[1,2-d][1,3]thiazol-2-yl naphtho[2,3-d][1,3]oxazol-2-yl, and naphtho[2,3-d][1,3]thiazol-2-yl.

Another aspect of the invention relates to compounds of formula (II) wherein $Ar_1$ is unsubstituted or substituted phenyl, $R_1$ is hydrogen, and $R_2$ is unsubstituted or substituted ring selected from the group consisting of 1,3-benzoxazol-2-yl, 1,3-benzothiazolyl, [1,3]thiazolo[5,4-b]pyridin-2-yl, 1,[1,3]thiazolo[5,4-b]pyrimidin-2-yl, 6,8-dihydrofuro[3,4-g][1,3]benzothiazol-2-yl, [1,3]thiazolo[5,4-h]quinolin-2-yl, [1,3]oxazolo[4,5-b]pyridin-2-yl, naphtho[1,2-d][1,3]oxazol-2-yl, and naphtho[2,3-d][1,3]oxazol-2-yl.

Another aspect of the invention relates to compounds of formula (II) wherein $Ar_1$ is phenyl, unsubstituted or substituted with 1, 2 or 3 substituents selected from the group consisting of —I, —Br, —Cl, and —F; $R_1$ is hydrogen, and $R_2$ is an unsubstituted or substituted ring selected from the group consisting of 1,3-benzoxazol-2-yl, 1,3-benzothiazolyl, [1,3]thiazolo[5,4-b]pyridin-2-yl, 1,[1,3]thiazolo[5,4-b]pyrimidin-2-yl, 6,8-dihydrofuro[3,4-g][1,3]benzothiazol-2-yl, [1,3]thiazolo[5,4-h]quinolin-2-yl, [1,3]oxazolo[4,5-b]pyridin-2-yl, naphtho[1,2-d][1,3]oxazol-2-yl, and naphtho[2,3-d][1,3]oxazol-2-yl.

Another aspect of the invention relates to compounds of formula (II) wherein $Ar_1$ is 2-chlorophenyl, 2,4-dichlorophenyl, 2-chloro-4-fluorophenyl or 2,4,5-trifluorophenyl; $R_1$ is hydrogen, and $R_2$ is an unsubstituted or substituted ring selected from the group consisting of 1,3-benzoxazol-2-yl, 1,3-benzothiazolyl, [1,3]thiazolo[5,4-b]pyridin-2-yl, 1,[1,3]thiazolo[5,4-b]pyrimidin-2-yl, 6,8-dihydrofuro[3,4-g][1,3]benzothiazol-2-yl, [1,3]thiazolo[5,4-h]quinolin-2-yl, [1,3]oxazolo[4,5-b]pyridin-2-yl, naphtho[1,2-d][1,3]oxazol-2-yl, and naphtho[2,3-d][1,3]oxazol-2-yl.

Exemplary compounds having formula (II) include, but are not limited to,
(1S,6R)-3-[5-(ethylsulfonyl)-1,3-benzoxazol-2-yl]-6-(2,4,5-trifluorophenyl)cyclohex-3-en-1-amine;
2-[(4R,5S)-5-amino-4-(2,4,5-trifluorophenyl)cyclohex-1-en-1-yl][1,3]thiazolo[5,4-b]pyridin-5-ol;
(1S,6R)-3-(5-methoxy[1,3]thiazolo[5,4-b]pyridin-2-yl)-6-(2,4,5-trifluorophenyl)cyclohex-3-en-1-amine;
2-[(4R,5S)-5-amino-4-(2,4,5-trifluorophenyl)cyclohex-1-en-1-yl]-N-methyl[1,3]thiazolo[5,4-d]pyrimidin-7-amine;
2-[(4R,5S)-5-amino-4-(2,4,5-trifluorophenyl)cyclohex-1-en-1-yl]furo[3,4-g][1,3]benzothiazol-8(6H)-one;
(1S,6R)-3-(7-chloro[1,3]thiazolo[5,4-h]quinolin-2-yl)-6-(2,4,5-trifluorophenyl)cyclohex-3-en-1-amine;
(1S,6R)-3-[1,3]oxazolo[4,5-b]pyridin-2-yl-6-(2,4,5-trifluorophenyl)cyclohex-3-en-1-amine;
(1S,6R)-3-naphtho[1,2-d][1,3]oxazol-2-yl-6-(2,4,5-trifluorophenyl)cyclohex-3-en-1-amine; and
(1S,6R)-3-naphtho[2,3-d][1,3]oxazol-2-yl-6-(2,4,5-trifluorophenyl)cyclohex-3-en-1-amine;

or a pharmaceutically acceptable salt, metabolite, prodrug, salt of a prodrug or a combination thereof.

The present invention also relates to compounds of formula (III)

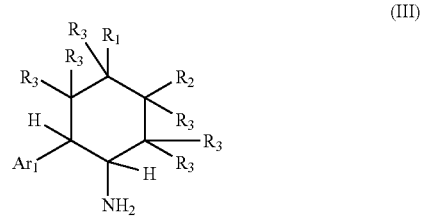

(III)

or a pharmaceutically acceptable salt, metabolite, prodrug, salt of a prodrug or a combination thereof; wherein $Ar_1$, $R_1$, $R_2$ and $R_3$ are as previously described in formula (I). It is understood that embodiments of $Ar_1$, $R_1$, $R_2$ and $R_3$ and combinations of embodiments, including preferred, more preferred and most preferred embodiments as described in formula (I) are also contemplated for compounds of formula (III).

Accordingly, one aspect of the invention relates to compounds of formula (III) wherein $Ar_1$ is aryl or heteroaryl, each of which is independently unsubstituted or substituted; $R_1$ is selected from the group consisting of hydrogen, alkyl, haloalkyl, aryl, heteroaryl, heterocycle, cycloalkyl and cycloalkenyl; and $R_2$ is selected from the group consisting of hydrogen, alkyl, haloalkyl, cycloalkyl, heterocycle, aryl, heteroaryl, heterocyclealkyl, -alkylenyl-$OR_4$, -alkylenyl-O-alkylenyl-$R_4$, -alkylenyl-$NR_5R_6$, and —C(O)G; wherein $R_4$, $R_5$, $R_6$ and G are as defined in formula (I), and each of the aryl, heteroaryl, heterocycle, cycloalkyl, cycloalkenyl and the heterocycle moiety of the heterocyclealkyl is independently unsubstituted or substituted with substituent as described herein.

Another aspect of the invention relates to compounds of formula (III) wherein $Ar_1$ is aryl, $R_1$ is selected from the group consisting of hydrogen, aryl, and heteroaryl; and $R_2$ is selected from the group consisting of hydrogen, aryl, heteroaryl, heterocycle, heterocyclealkyl, -alkylenyl-$OR_4$, -alkylenyl-$NR_5R_6$, and —C(O)G; wherein $R_4$, $R_5$, $R_6$ and G are as defined in formula (I), and wherein each of the aryl, heteroaryl, heterocycle, and the heterocycle moiety of the heterocyclealkyl is independently unsubstituted or substituted with substituent as described herein.

Another aspect of the invention relates to compounds of formula (III) wherein $Ar_1$ is unsubstituted or substituted aryl. $R_1$ is hydrogen; and $R_2$ is selected from the group consisting of hydrogen and —C(O)G; wherein G is an unsubstituted or substituted heterocycle.

Another aspect of the invention relates to compounds of formula (III) wherein $Ar_1$ is unsubstituted or substituted aryl; $R_1$ is hydrogen; $R_2$ is selected from the group consisting of hydrogen and —C(O)G; wherein G is an unsubstituted or substituted heterocycle; and $R_3$ is hydrogen.

Another aspect of the invention relates to compounds of formula (III) wherein $Ar_1$ is unsubstituted or substituted phenyl; $R_1$ is hydrogen; $R_2$ is selected from the group consisting of hydrogen and —C(O)G; wherein G is an unsubstituted or substituted heterocycle selected from the group consisting of piperidinyl, pyrrolidinyl, 5,6-dihydro[1,2,4]triazolo[4,3-a]pyrazin-7(8H)-yl, piperazinyl, 1,2,3,4-tetrahydroisoquinolin-2-yl, 1,2,3,4-tetrahydroquinolinyl, morpholinyl, 1,3-thiazolidinyl, 5,6-dihydroimidazo[1,2-a]pyrazin-7(8H)-yl, 2,3-dihydro-1H-indolyl, and 1,3-dihydroisoindol-2-yl.

Another aspect of the invention relates to compounds of formula (III) wherein $Ar_1$ is phenyl, unsubstituted or substituted with 1, 2, or 3 substituents selected from the group consisting of —I, —Br, —Cl and —I; $R_1$ is hydrogen; $R_2$ is selected from the group consisting of hydrogen and —C(O)G; wherein G is an unsubstituted or substituted heterocycle selected from the group consisting of piperidinyl, pyrrolidinyl, 5,6-dihydro[1,2,4]triazolo[4,3-a]pyrazin-7(8H)-yl, piperazinyl, 1,2,3,4-tetrahydroisoquinolin-2-yl, 1,2,3,4-tetrahydroquinolinyl, morpholinyl, 1,3-thiazolidinyl, 5,6-dihydroimidazo[1,2-a]pyrazin-7(8H)-yl, 2,3-dihydro-1H-indolyl, and 1,3-dihydroisoindol-2-yl.

Another aspect of the invention relates to compounds of formula (III) wherein $Ar_1$ is unsubstituted or substituted phenyl; $R_1$ is hydrogen and $R_2$ is selected from the group consisting of hydrogen and —C(O)G; wherein G is an unsubstituted or substituted heterocycle ring selected from the group consisting of piperidinyl, pyrrolidinyl, 1,2,3,4-tetrahydroisoquinolin-2-yl, 5,6-dihydroimidazo[1,2-a]pyrazin-7(8H)-yl, 5,6-dihydro[1,2,4]triazolo[4,3-a]pyrazin-7(8H)-yl, piperazinyl, morpholinyl, and 1,3-thiazolidin-3-yl.

Another aspect of the invention relates to compounds of formula (III) wherein $Ar_1$ is phenyl, unsubstituted or substituted with 1, 2, or 3 substituents selected from the group consisting of —I, —Br, —Cl and —I; $R_1$ is hydrogen; $R_2$ is selected from the group consisting of hydrogen and —C(O)G; wherein G is an unsubstituted or substituted 5,6-dihydroimidazo[1,2-a]pyrazin-7(8H)-yl; and $R_3$ is hydrogen.

Exemplary compounds of the present invention having formula (III) include, but are not limited to, 6-(2,4-dichlorophenyl)cyclohexane-1-amine; and (1S,2R)-5-{[2-(trifluoromethyl)-5,6-dihydroimidazo[1,2-a]pyrazin-7(8H)-yl]carbonyl}-2-(2,4,5-trifluorophenyl)cyclohexanamine;

or a pharmaceutically acceptable salt, metabolite, prodrug, salt of a prodrug, or a combination thereof.

According to one embodiment of the present invention, there is provided a method to improve glucose tolerance in type II diabetes comprising administering a therapeutically effective amount of a compound of formula (I), (II), (II), or (IV). According to another embodiment of the present invention, there is provided a method for treating type 2 diabetes, insulin resistance, hyperinsulinemia, impaired glucose tolerance, obesity, hypercholesterolemia, and hypertriglyceridemia comprising administering a therapeutically effective amount of a compound of formula (I), (II), (III) or (IV).

According to still another embodiment, the present invention is directed to a pharmaceutical composition comprising a therapeutically effective amount of a compound of formula (I), (II), (III), or (IV) in combination with a pharmaceutically suitable carrier.

According to another embodiment of the present invention there is provided a method of inhibiting DPP-IV comprising administering a therapeutically effective amount of a compound of formula (I), (II), (III) or (IV).

According to another embodiment of the present invention there is provided a method of treating disorders by inhibiting DPP-IV comprising administering a therapeutically effective amount of a compound of formula (I), (II), (III) or (IV).

According to another embodiment of the present invention there is provided a method of treating diabetes, comprising administering a therapeutically effective amount of a compound of formula (I), (II), (III) or (IV).

According to another embodiment of the present invention there is provided a method of treating type II diabetes, comprising administering a therapeutically effective amount of a compound of formula (I), (II), (III) or (IV).

According to another embodiment of the present invention there is provided a method of treating hyperglycemia, comprising administering a therapeutically effective amount of a compound of formula (I), (II), (III) or (IV).

According to another embodiment of the present invention there is provided a method of treating metabolic syndrome or Syndrome X, comprising administering a therapeutically effective amount of a compound of formula (I), (II), (III) or (IV).

According to another embodiment of the present invention there is provided a method of treating hyperinsulinemia, comprising administering a therapeutically effective amount of a compound of formula (I), (II), (III) or (IV).

According to another embodiment of the present invention there is provided a method of treating obesity, comprising administering a therapeutically effective amount of a compound of formula (I), (II), (III) or (IV).

According to another embodiment of the present invention there is provided a pharmaceutical composition comprising a therapeutically effective amount of a compound of formula (I), (II), (III) or (IV) in combination with a pharmaceutically suitable carrier.

The present invention is also directed to a method of treating disorders mediated by DPP-IV through inhibition of enzymatic activity. Disorders known to be regulated through enzymatic activity are diabetes, especially type II diabetes, as well as hyperglycemia, Syndrome X, hyperinsulinemia, obesity, atherosclerosis, and various immunomodulatory diseases. Therefore, according to an embodiment of the present invention there are provided compounds of formula (I), which are useful for the treatment of diabetes, especially type II diabetes, as well as hyperglycemia, Syndrome X, hyperinsulinemia, obesity, atherosclerosis, and various immunomodulatory diseases.

The present invention is further directed to a method of treating diseases such as, but not limited to, cardiovascular disease, atherosclerosis, cerebrovascular diseases, diseases and disorders of the central nervous system, schizophrenia, anxiety, bipolar disease, depression, insomnia, cognitive disorders, gastrointestinal diseases and disorders, cancer, inflammation and inflammatory diseases, respiratory diseases and disorders, musculo-skeletal disorders, osteoporosis, menopausal symptoms, periodontal diseases, gingivitis, and various immunomodulatory diseases comprising administering a therapeutically effective amount of a compound of formula (I), (II), (III), or (IV).

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I).

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I) for example, by hydrolysis in blood.

The present compounds can exhibit the phenomena of tautomerism or structural isomerism. As the drawings within this specification can only represent one possible tautomeric or structural isomeric form, it should be understood that the invention encompasses any tautomeric or structural isomeric form, or mixtures thereof, which possess the ability to inhibit DPP-IV, and is not limited to any one tautomeric or structural isomeric form utilized within the drawings.

Compounds comprising geometric isomers of carbon-carbon double bonds and carbon-nitrogen double are meant to be included in this invention. Substituents around a carbon-carbon or a carbon-nitrogen double bond are designated as being of Z or E configuration and substituents around a cycloalkyl or heterocycloalkyl are designated as being of cis or trans configuration.

It will be appreciated by those skilled in the art that the compounds of this invention, exemplified by formula (I), (II) or (III), can exist as geometric isomers. All geometric isomeric forms and mixtures thereof of the compounds described herein are intended to be encompassed within the scope of the present invention. Examples of some of the possible geometric isomeric forms of the compounds of this invention include, but are not limited to: cis isomer comprising mixture of compounds of formulae (VI) and (VII), trans isomer comprising of compounds of formulae (IV) and (V), and mixture of geometric isomer (any mixture comprising of compounds of formulae (IV)-(VII)).

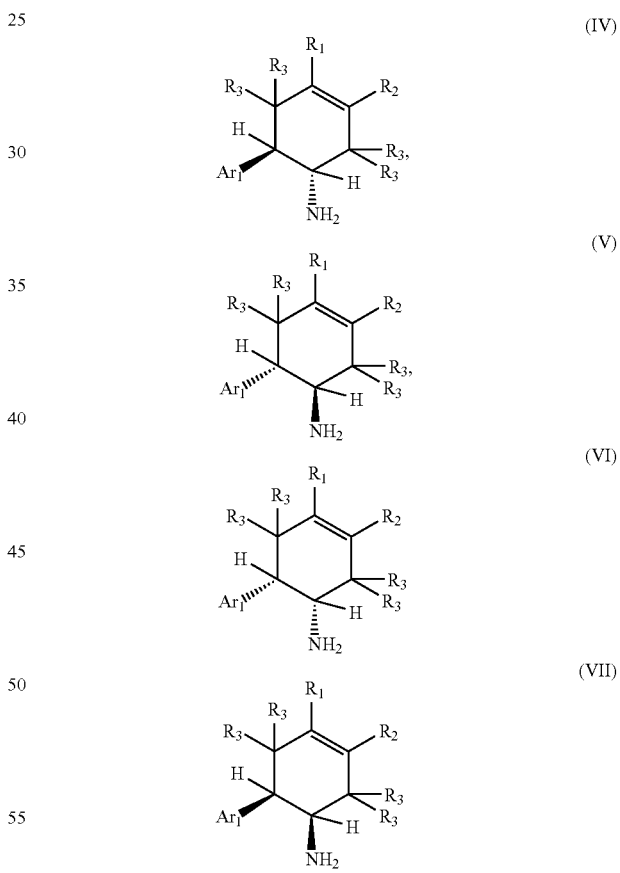

or a pharmaceutically acceptable salt, metabolite, prodrug, salt of a prodrug or a combination thereof; wherein $Ar_1$, $R_1$, $R_2$ and $R_3$ are as described in formula (I). It is understood that embodiments of $Ar_1$, $R_1$, $R_2$ and $R_3$ and combinations of embodiments, including preferred, more preferred and most preferred embodiments as described in formula (I) are also contemplated for compounds of formula (IV), (V), (VI) or (VII).

Asymmetric centers exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well-known in the art.

Compounds of this invention contain at least one chiral center and can exist as single stereoisomers (e.g. single enantiomer), mixtures of stereoisomers (e.g. any mixture of enantiomers or diastereomers) or racemic mixtures thereof. As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds containing either stereoisomer of each chiral center present in the compound.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of DPP-IV by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) to effectively ameliorate disorders by inhibiting DPP-IV at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DPP-IV in single or divided doses can be in amounts, for example, from about 0.01 to 50 mg/kg body weight. In a more preferred range, compounds of the present invention inhibit the action of DPP-IV in a single or divided doses from about 0.05 to 25 mg/kg body weight. Single dose compositions can contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

BIOLOGICAL DATA

Isolation of Rat DPP-IV

DPP-IV was purified to homogeneity (electrophoretic) from rat kidney as described in *Arch. Biochem. Biophy.* 1995, 323, 148-154. Rat kidney (120 g) was homogenized in 4 volumes of water and the homogenate centrifuged for 15 minutes at 1000 g. The pH of the supernatant was adjusted to 3.9 with 1 M HCl and the enzyme solubilized by autolysis for 18 hours at 37° C. The pH of the supernatant collected after centrifugation was adjusted to 7.2 with 1 M Trizma base and the enzyme was precipitated with $(NH_4)_2SO_4$ at 90% saturation (662 g solid ammonium sulfate per liter of solution). The solubilized precipitate was chromatographed on Sephadex G-200 (1 m×5 cm) equilibrated with a 10 mM Tris-HCl buffer pH 7.5 containing NaCl at a final concentration of 0.1 M and developed from the bottom. Fractions containing enzymatic activity were pooled, chromatographed on DE-52 (16×2.5 cm) equilibrated with 10 mM Tris-HCl, pH 7.5, and eluted with a 250-mL linear 0-0.4 M NaCl gradient prepared in 10 mM Tris-HCl. DPP-IV was then resolved from other brush border peptidases by chromatography on a phenyl Sepharose column (12×2 cm) equilibrated with 25% $(NH_4)_2SO_4$ at saturation (144 g ammonium sulfate per liter of 0.05 M Tris-HCl, pH 7.5). The enzyme was eluted in a homogeneous form with a 200-mL linear gradient of 25-0% $(NH_4)_2SO_4$, prepared in 0.05 M Tris HCl buffer.

Isolation of Human DPP-IV

Caco-2 cells were obtained from American Type Culture Collection (P.O. Box 3605, Manassas, Va.), cultured and maintained at 37° C. with 5% $CO_2$ in low glucose DMEM media supplemented with 10% Fetal Bovine Serum and antibiotic/antimycotic. In preparation for making an extract, cells were seeded at a density to achieve confluence within 7 days. The cells were cultured for an additional 14 days to allow for maximal DPPIV expression. On the day of harvest, cells were washed once with Dulbecco's PBS and solubilized in a 10 mM NaCl containing 50 mM Tris HCl, 0.5% Nonidet P40 and 0.3 ug/mL aprotinin at pH 8.0. The extract was clarified by centrifugation at 35,000 g for 30 minutes at 4° C. Human DPP-IV was purified from this extract supernatant, using precipitation with $(NH_4)_2SO_4$ at 90% saturation, as described for the rat DPP-IV. Human DPP-IV was purified from this solubilized precipitate by the same procedure as described for the solubilized precipitate of rat DPP-IV. The purified enzyme was stored frozen at –70° C. as drops collected in liquid nitrogen.

Inhibition Constant Determination for DPP-IV

DPP-IV activity was determined by measuring the rate of hydrolysis of a surrogate substrate Gly-Pro-7-amido-methyl-coumarin (Gly-Pro-AMC, Catalogue #G-2761, Sigma, St. Louis, Mo.). The assay is carried out at room temperature in black 96 well polypropylene or polyethylene plates in a total volume of 100 μL per well. Appropriate dilutions of the compounds are made in DMSO and then diluted ten fold into water. 10 μL of 5 concentrations of the compound of formula (I) (inhibitor) or 10% DMSO in water are added to individual wells containing 80 μL of DPP-IV diluted in assay buffer containing 25 mM HEPES (pH 7.5), 150 mM NaCl and 0.12 mg/mL BSA. After 10 minutes at room temperature, the reaction is initiated by adding 10 μL of either 280, 700, 1750, or 3500 μM Gly-Pro-AMC in water. The DPP-IV activity results in the formation of the fluorescent product amido-methylcoumarin (AMC) which is continuously monitored by excitation at 350 nm and measurement of fluorescent emission at 460 nm every 112 seconds for 37 minutes using an appropriate plate reader. The fluorescence at 460 nm is converted to nanomoles of AMC using a standard curve and the initial rate of AMC formation is calculated. For each concentration of each of the compounds of formula (I) (inhibitor) or DMSO control, the initial rates are used to fit the rectangular hyperbola of Michaelis-Menten by non-linear regression analysis (GraphPad Software Prism 3.0). The ratio of the apparent Km/Vmax vs. inhibitor concentration is plotted and the competitive Ki is calculated by linear regression to be the negative x-intercept. The uncompetitive Ki is similarly calculated from the x-intercept of the plot of the reciprocal of the apparent Vmax versus the inhibitor concentration (Cornish-Bowden , A. 1995. Fundamentals of Enzyme Kinetics. Revised edition. Portland Press, Ltd., London, U.K.).

The compounds of the present invention were found to inhibit DPP-IV induced fluorescence with inhibitory constants in a range of about 0.0001 μM to about 7 μM. In a preferred range, the compounds of the present invention inhibited DPP-IV induced fluorescence with inhibitory constants in a range of about of about 0.0001 μM to about 1 μM; and in a more preferred range, the compounds of the present invention inhibited DPP-IV induced fluorescence with inhibitory constants in a range of about of about 0.0001 μM to about 0.1 μM.

TABLE 1

DPP-IV Inhibition of compounds of the present invention ($K_{IC}$ nM).

| | | | | |
|---|---|---|---|---|
| 255 | 144 | 416 | 190 | 322 |
| 254 | 135 | 258 | 140 | 146 |
| 46 | 157 | 136 | 40 | 62 |
| 30 | 5 | 71 | 73 | 91 |
| 164 | 23 | 28 | 11 | 11 |
| 41 | 27 | 21 | 36 | 12 |
| 29 | 11 | 27 | 29 | 6 |
| 4 | 34 | 8 | 19 | 24 |
| 34 | 14 | 48 | 12 | 58 |
| 2 | 82 | 58 | 2 | 23 |
| 17 | 14 | 9 | 3 | 3 |
| 4 | 5 | 144 | 45 | 14 |
| 18 | 226 | 123 | 5 | 29 |
| 13 | 4 | 11 | 61 | 26 |
| 27 | 34 | 17 | 12 | 50 |
| 65 | 70 | 101 | 172 | 97 |
| 13 | 28 | 14 | 22 | 16 |
| 17 | 15 | <1 | 9 | 1 |
| <1 | 25 | 16 | 271 | 45 |

As inhibitors of DPP-IV action, the compounds of the present invention are useful in treating disorders that are mediated by DPP-IV. Disorders that are mediated by DPP-IV include diabetes, type II diabetes, hyperglycemia, Syndrome X, hyperinsulinemia and obesity. Therefore the compounds of the present invention are useful in treating the disorder of diabetes, type II diabetes, hyperglycemia, Syndrome X, hyperinsulinemia and obesity.

Dipeptidyl-peptidase IV (DPP-IV, EC 3.4.14.5; CD26) is a post-proline cleaving serine protease with significant homology to other alpha-beta hydroxylases (e.g. prolyl oligopeptidase). DPP-IV is found throughout the body, both circulating in plasma and as a type II membrane protein produced by a variety of tissues, including kidney, liver and intestine. DPP-IV plays a role in the cleavage of specific substrates with accessible amino-terminal Xaa-Pro- or Xaa-Ala-dipeptide sequences, resulting in their inactivation or alteration in their biological activities. Important DPP-IV substrates include growth hormone releasing hormone, glucagon-like peptides GLP-1 and 2, gastric inhibitory polypeptide (GIP) and certain chemokines like RANTES (regulated on activation, normal T cell expressed and secreted), stromal cell-derived factor, eotaxin, and macrophage-derived chemokine (Mentlein, R. *Regulatory Peptides,* 1999, 85, 9-24).

The DPP-IV substrate, glucagon-like peptide GLP-1, is released from L cells in the distal small intestine and colon after oral ingestion of nutrients. The active GLP-1 (7-36) amide is an incretin that increases glucose stimulated insulin secretion (Drucker, D. J. *Diabetes,* 1998, 47, 159-169). Other activities attributed to GLP-1 (7-36) amide include stimulation of insulin gene expression, trophic effects on pancreatic beta cells, inhibition of glucagon secretion, promotion of satiety, inhibition of food intake, and slowing of gastric emptying (Drucker, D. J. *Diabetes,* 1998, 47, 159-169). These effects of GLP-1 (7-36) amide contribute to glucose homeostasis and the normalization of blood glucose levels in conditions of impaired glucose tolerance. In this regard, GLP-1 (7-36) amide has been demonstrated to reduce postprandial and fasting glycemia in patients with insulin-dependent and non-insulin-dependent diabetes mellitus (Nauck, et al., *Hormone Metab. Res.* 2002, 29, 411-416; Gutniak et al., *J. Internal Medicine,* 2001, 250, 81-87; Rauchman, et al., *Diabetologia.* 1997, 40, 205-11; Ahren, B., *BioEssays* 1998, 20, 642-51). GLP-1 based therapy has therapeutic potential for the treatment of type 2 diabetes. However, active GLP-1 (7-36) amide is rapidly converted to GLP-1 (9-36) amide by DPP-IV cleavage of the amino-terminal His-Ala-dipeptide of GLP-1 (7-36) amide (Mentlein, et al., *Eur. J. Biochem.* 1993, 214, 829-835). The resulting GLP-1 (9-36) amide is inactive and is an antagonist of the GLP-1 receptor (Knudson, et al., *Eur. J. Pharmacol.* 1996, 318, 429-35). The short half-life of GLP-1 (7-36) amide in the circulation (1-1.5 minutes) makes it impractical as a therapeutic agent and has led to the development of alternative strategies to enhance the anti-diabetogenic activity of GLP-1. One strategy is to increase the circulating half-life of GLP-1, by inhibiting DPP-IV activity (Deacon, et al., *Diabetes* 1995, 44 1126-31). Inhibition of DPP-IV in vivo increases the level of circulating GLP-1 (7-36) amide with a concomitant increase in its insulinotropic effect (Deacon, et al., *Diabetes.* 1998, 47, 764-9). A DPP-IV inhibitor has been demonstrated to improve glucose tolerance in non-insulin-dependent diabetes mellitus (Ahren B, et al., *Diabetes Care* 2002, 25, 869-875). Therefore, the compounds of the present invention, including but not limited to those specified in the examples can be used in the treatment of conditions caused by or associated with impaired glucose tolerance including the prevention or treatment of diabetes, especially non-insulin-dependent diabetes mellitus, hyperglycemia, hyperinsulinemia and metabolic syndrome (Johannsson, et al., *J. Endocrinol. Invest.* 1999, 22(5 Suppl), 41-6).

Striking similarities exist between the metabolic syndrome (syndrome X) and untreated growth hormone deficiency. Abdominal/visceral obesity and insulin resistance characterize both syndromes (Reaven, G M, *Physiol. Rev.* 1995, 75, 473-86; Johansson, et al., *Metabolism* 1995, 44, 1126-29). Growth hormone favorably effects some of the perturbations associated with abdominal/visceral obesity, including reduction in abdominal/visceral obesity, improved insulin sensitivity and lipoprotein metabolism and reduction in diastolic blood pressure (Barreto-Filho, et al., *J. Clin. Endocrinol. Metab.* 2002, 87(5), 2018-23; Colao et al., *J. Clin. Endocrinol. Metab.* 2002, 87(3), 1088-93; Gotherstrom, et al., *J. Clin. Endocrinol. Metab.* 2001, 86(10), 4657-65; Johannsson, et al., *J. Endocrinol. Invest.* 1999, 22(5 Suppl), 41-6; Johannsson, et al., *J. Clin. Endocrinol. Metab.* 1997, 82(3), 727-34).

For the treatment of diabetes or Syndrome X, compounds of the present invention can be used alone, or in combination with any existing anti-diabetic agent. Agents which can be used in combination with the compounds of the present invention include, but are not limited to insulin, an insulin analog such as mecasermin and the like, an insulin secretagogue such as nateglinide and the like, a biguanide such as metformin and the like, a sulfonylurea such as chlorpropamide, glipizide, glyburide, and the like, an insulin sensitizing agent such as a PPARγ agonist such as troglitazone, pioglitazone, rosiglitazone, and the like, an α-glucosidase inhibitor such as acarbose, voglibose, miglitol and the like, an aldose reductase inhibitor such as zopolrestat and the like, a metiglinide such as repaglinide and the like, a glycogen phosphorylase inhibitor, GLP-1 or a mimetic of GLP-1 such as exendin-4, or other such anti-diabetic agents that are known to one skilled in the art. The ability of the compounds of the present invention to treat diabetes, alone or in combination with another agent, can be demonstrated according to the methods described by Zander, M.; Mustafa, T.; Toft-Nielsen, M.-B.; Madsbad, S.; Holst, J. J. in *Diabetes Care* 2001, 24, 720-725; or, according to the methods described herein.

DPP-IV-mediated proteolysis has been established as a major route of growth hormone releasing hormone (GHRH) degradation and inactivation (Kubiak, et al., *Drug Metab. Dispos.* 1989, 17, 393-7). GHRH-derivatives that are resistant to DPP-IV cleavage are more potent in increasing serum growth hormone levels when administered i.v. due to longer stability in vivo. DPP-IV inhibition would be predicted to increase GHRH levels and thus serum growth hormone levels. Therefore, the compounds of the present invention, including but not limited to those specified in the examples can be used in the treatment of conditions associated with deficiency in growth hormone including metabolic disorders (central obesity, dyslipidemia), osteoporosis and frailty of aging.

Diabetic dyslipidemia is characterized by multiple lipoprotein defects including moderately high serum levels of cholesterol and triglycerides, small LDL particles and low levels of HDL cholesterol. The dyslipidemia associated with non-insulin-dependent diabetes mellitus is improved in conjunction with improved diabetic condition following treatment with GLP-1 (Junti-Berggren, et al., *Diabetes Care* 1996, 19, 1200-6). DPP-IV inhibition is predicted to increase the level of circulating GLP-1 (7-36) amide and thereby would be effective in the treatment of diabetic dyslipidemia and associated complications. Therefore, the compounds of the present invention, including but not limited to those specified in the examples can be used in the treatment of hypercholesterolemia, hypertriglyceridemia and associated cardiovascular disease.

Parenteral injection of GLP-1 (7-36) amide in healthy men, obese men or patients with non-insulin-dependent diabetes mellitus has been reported to promote satiety and to suppress food intake (Flint, et al., *J. Clin. Invest.* 1998, 101, 515-520; Naslund, et al., *Am. J. Clin. Nutr.* 1998, 68, 525-530; Gutzwiller, et al., *Am. J. Physiol.* 1999, 276, R1541-R1544.) DPP-IV inhibition is predicted to increase the level of circulating GLP-1 (7-36) amide and thereby increases satiety in obesity and non-insulin-dependent diabetes mellitus. Therefore, the compounds of the present invention, including but not limited to those specified in the examples can be used in the treatment of obesity.

For the treatment of obesity, compounds of the present invention can be used alone, or in combination with any existing anti-obesity agent as described by Flint, A.; Raben, A.; Astrup, A.; Holst, J. J. in *J. Clin. Invest.* 1998, 101, 515-520 or by Toft-Nielsen, M.-B.; Madsbad, S.; Holst, J. J. in *Diabetes Care* 1999, 22, 1137-1143. Agents which can be used in combination with the compounds of the present invention include, but are not limited to fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, thyromimetic agents, or other such anti-obesity agents that are known to one skilled in the art.

DPP-IV is expressed on a fraction of resting T cells at low density but is strongly upregulated following T-cell activation. DPP-IV can have important functions on T cells and in the immune system. Synthetic inhibitors of the enzymatic activity of CD26 have been shown to suppress certain immune reactions in vitro and in vivo. In vitro recombinant soluble DPP-IV enhances proliferative responses of peripheral blood lymphocytes to stimulation with soluble tetanus toxoid antigen. In addition, the enhancing effect requires DPP-IV enzyme activity (Tanaka, et al., *Proc. Natl. Acad. Sci.* 1994, 91, 3082-86; Tanaka, et al., *Proc. Natl. Acad. Sci.* 1993, 90, 4583). Soluble DPP-IV up-regulates the expression of the costimulatory molecule CD86 on monocytes through its dipeptidyl peptidase IV activity suggesting that soluble DPP-IV enhances T cell immune response to recall antigen via its direct effect on antigen presenting cells (Ohnuma, et al., *J. Immunol.* 2001, 167(12), 6745-55). Consequently, DPP-IV inhibition would be predicted to suppress certain immune responses and thus have therapeutic benefit in the treatment of immunomodulatory diseases. Therefore, the compounds of the present invention, including but not limited to those specified in the examples can be used in the treatment of rheumatoid arthritis, multiple sclerosis, scleraderma, chronic inflammatory bowel disease or syndrome and allograft rejection in transplantation.

Chemokine receptors, especially CCR5 and CXCR4, act as cofactors for HIV-1 entry into CD4+ cells and their corresponding ligands can suppress HIV entry and thus replication. The CXC chemokine, stromal cell derived factor-1 (SDF-1) is a chemokine for resting T-lymphocytes and monocytes. SDF-1 exists as two splice variants, SDF-1alpha and SDF-1beta that differ by four additional C-terminal residues in SDF-1beta. Truncation of the N-terminal Lys-Pro-residues from both SDF-1 alpha and SDF-1 beta results in the loss of their chemotactic and antiviral activities in vitro (Ohtsuki, et al, *FEBS Lett.* 1998, 431, 236-40; Shioda, et al., *Proc. Natl. Acad. Sci.* 1998, 95(11), 6331-6; Proost, et al., *FEBS Lett.* 1998, 432, 73-6). DPP-IV inactivates SDF-1 alpha as a ligand for CXCR4 that is a T cell chemotactic receptor as well as the major co-receptor for T-tropic HIV-1 strains. DPP-IV inhibition would be predicted to increase full-length SDF-1 levels and thereby suppress HIV-1 entry into CXCR4+ cells. Therefore, the compounds of the present invention, including but not limited to those specified in the examples can be used in the treatment of HIV infection (AIDS).

Dipeptidyl-peptidase IV (DPPIV, EC 3.4.14.5; CD26) is a post-proline cleaving serine protease with significant homology to other alpha-beta hydroxylases (e.g. prolyl oligopeptidase). DPPIV is found throughout the body, both circulating in plasma and as a type II membrane protein produced by a variety of tissues, including kidney, liver and intestine. DPPIV plays a role in the cleavage of specific substrates with accessible amino-terminal Xaa-Pro- or Xaa-Ala-dipeptide sequences, resulting in their inactivation or alteration in their biological activities. Important DPPIV substrates include growth hormone releasing hormone, glucagon-like peptides (GLP)-1 and 2, gastric inhibitory polypeptide (GIP) and certain chemokines like RANTES (regulated on activation, normal T cell expressed and secreted), stromal cell-derived factor, eotaxin, and macrophage-derived chemokine (Mentlein, R. *Regulatory Peptides,* 1999, 85, 9-24).

The DPPIV substrate, glucagon-like peptide (GLP)-1, is released from L cells in the distal small intestine and colon after oral ingestion of nutrients. The active GLP-1 (7-36) amide is an incretin that increases glucose stimulated insulin secretion (Drucker, D. J. *Diabetes,* 1998, 47, 159-169). Other activities attributed to GLP-1 (7-36) amide include stimulation of insulin gene expression, trophic effects on pancreatic beta cells, inhibition of glucagon secretion, promotion of satiety, inhibition of food intake, and slowing of gastric emptying (Drucker, D. J. *Diabetes,* 1998, 47, 159-169). These effects of GLP-1 (7-36) amide contribute to glucose homeostasis and the normalization of blood glucose levels in conditions of impaired glucose tolerance. In this regard, GLP-1 (7-36) amide has been demonstrated to reduce postprandial and fasting glycemia in patients with insulin-dependent and non-insulin-dependent diabetes mellitus (Nauck, et al., *Hormone Metab. Res.* 2002, 29, 411-416; Gutniak et al., *J. Internal Medicine,* 2001, 250, 81-87; Rauchman, et al., *Diabetologia.* 1997, 40, 205-11; Ahren, B., *BioEssays* 1998, 20, 642-51). GLP-1 based therapy has therapeutic potential for the treatment of type 2 diabetes. However, active GLP-1 (7-36) amide is rapidly converted to GLP-1 (9-36) amide by DPPIV cleavage of the amino-terminal His-Ala-dipeptide of GLP-1 (7-36) amide (Mentlein, et al., *Eur. J. Biochem.* 1993, 214, 829-835). The resulting GLP-1 (9-36) amide is inactive and is an antagonist of the GLP-1 receptor (Knudson, et al., *Eur. J. Pharmacol.* 1996, 318, 429-35).

The short half-life of GLP-1 (7-36) amide in the circulation (1-1.5 minutes) makes it impractical as a therapeutic agent and has led to the development of alternative strategies to enhance the anti-diabetogenic activity of GLP-1. One strategy is to increase the circulating half-life of GLP-1, by inhibiting DPPIV activity (Deacon, et al., *Diabetes* 1995, 44 1126-31). Inhibition of DPPIV in vivo increases the level of circulating GLP-1 (7-36) amide with a concomitant increase in its insulinotropic effect (Deacon, et al., *Diabetes.* 1998, 47, 764-9). A DPPIV inhibitor has been demonstrated to improve glucose tolerance in non-insulin-dependent diabetes mellitus (Ahren B, et al., *Diabetes Care* 2002, 25, 869-875). Therefore, the compounds of the present invention, including but not limited to those specified in the examples, can be used in the treatment of conditions caused by or associated with impaired glucose tolerance including the prevention or treatment of diabetes, especially non-insulin-dependent diabetes mellitus, hyperglycemia, hyperinsulinemia and metabolic syndrome (Johannsson, et al., *J. Endocrinol. Invest.* 1999, 22(5 Suppl), 41-6).

Striking similarities exist between the metabolic syndrome (syndrome X) and untreated growth hormone deficiency. Abdominal/visceral obesity and insulin resistance characterize both syndromes (Reaven, G M, *Physiol. Rev.* 1995, 75, 473-86; Johansson, et al., *Metabolism* 1995, 44, 1126-29). Growth hormone favorably effects some of the perturbations associated with abdominal/visceral obesity, including reduction in abdominal/visceral obesity, improved insulin sensitivity and lipoprotein metabolism and reduction in diastolic blood pressure (Barreto-Filho, et al., *J. Clin. Endocrinol. Metab.* 2002, 87(5), 2018-23; Colao et al., *J. Clin. Endocrinol. Metab.* 2002, 87(3), 1088-93; Gotherstrom, et al., *J.*

*Clin. Endocrinol. Metab.* 2001, 86(10), 4657-65; Johannsson, et al., *J. Endocrinol. Invest.* 1999, 22(5 Suppl), 41-6; Johannsson, et al., *J. Clin. Endocrinol. Metab.* 1997, 82(3), 727-34). DPPIV-mediated proteolysis has been established as a major route of growth hormone releasing hormone (GHRH) degradation and inactivation (Kubiak, et al., *Drug Metab. Dispos.* 1989, 17, 393-7). GHRH-derivatives that are resistant to DPPIV cleavage are more potent in increasing serum growth hormone levels when administered i.v. due to longer stability in vivo. DPPIV inhibition would be predicted to increase GHRH levels and thus serum growth hormone levels. Therefore, the compounds of the present invention, including but not limited to those specified in the examples, can be used in the treatment of conditions associated with deficiency in growth hormone including metabolic disorders (central obesity, dyslipidemia), osteoporosis and frailty of aging.

For the treatment of diabetes or metabolic syndrome, compounds of the present invention can be used alone, or in combination with any existing anti-diabetic agent. Agents which can be used in combination with the compounds of the present invention include, but are not limited to, insulin, an insulin analog such as mecasermin and the like, an insulin secretagogue such as nateglinide and the like, a biguanide such as metformin and the like, a sulfonylurea such as chlorpropamide, glipizide, glyburide, and the like, an insulin sensitizing agent such as a PPARγ agonist such as troglitazone, pioglitazone, rosiglitazone, and the like, an α-glucosidase inhibitor such as acarbose, voglibose, miglitol and the like, an aldose reductase inhibitor such as zopolrestat and the like, a metiglinide such as repaglinide and the like, a glycogen phosphorylase inhibitor, GLP-1 or a mimetic of GLP-1 such as exendin-4, or other such anti-diabetic agents that are known to one skilled in the art. The ability of the compounds of the present invention to treat diabetes, alone or in combination with another agent, can be demonstrated according to the methods described by Zander, M.; Mustafa, T.; Toft-Nielsen, M.-B.; Madsbad, S.; Holst, J. J. in *Diabetes Care* 2001, 24, 720-725; or, according to the methods described herein.

Diabetic dyslipidemia is characterized by multiple lipoprotein defects including moderately high serum levels of cholesterol and triglycerides, small LDL particles and low levels of HDL cholesterol. The dyslipidemia associated with non-insulin-dependent diabetes mellitus is improved in conjunction with improved diabetic condition following treatment with GLP-1 (Junti-Berggren, et al., *Diabetes Care* 1996, 19, 1200-6). DPPIV inhibition is predicted to increase the level of circulating GLP-1 (7-36) amide and thereby would be effective in the treatment of diabetic dyslipidemia and associated complications. Therefore, the compounds of the present invention, including but not limited to those specified in the examples, can be used in the treatment hypercholesterolemia, hypertriglyceridemia and associated cardiovascular disease.

Parenteral injection of GLP-1 (7-36) amide in healthy men, obese men or patients with non-insulin-dependent diabetes mellitus has been reported to promote satiety and to suppress food intake (Flint, et al., *J. Clin. Invest.* 1998, 101, 515-520; Naslund, et al., *Am. J. Clin. Nutr.* 1998, 68, 525-530; Gutzwiller, et al., *Am. J. Physiol.* 1999, 276, R1541-R1544.) DPPIV inhibition is predicted to increase the level of circulating GLP-1 (7-36) amide and thereby increases satiety in obesity and non-insulin-dependent diabetes mellitus. Therefore, the compounds of the present invention, including but not limited to those specified in the examples, can be used in the treatment of obesity.

For the treatment of obesity, compounds of the present invention can be used alone, or in combination with any existing anti-obesity agent as described by Flint, A.; Raben, A.; Astrup, A.; Holst, J. J. in *J. Clin. Invest.* 1998, 101, 515-520 or by Toft-Nielsen, M.-B.; Madsbad, S.; Holst, J. J. in *Diabetes Care* 1999, 22, 1137-1143. Agents which can be used in combination with the compounds of the present invention include, but are not limited to, fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, thyromimetic agents, or other such anti-obesity agents that are known to one skilled in the art.

DPPIV is expressed on a fraction of resting T cells at low density, but is strongly upregulated following T-cell activation. DPPIV can have important functions on T cells and in the immune system. Synthetic inhibitors of the enzymatic activity of CD26 have been shown to suppress certain immune reactions in vitro and in vivo. In vitro recombinant soluble DPPIV enhances proliferative responses of peripheral blood lymphocytes to stimulation with soluble tetanus toxoid antigen. In addition, the enhancing effect requires DPPIV enzyme activity (Tanaka, et al., *Proc. Natl. Acad. Sci.* 1994, 91, 3082-86; Tanaka, et al., *Proc. Natl. Acad. Sci.* 1993, 90, 4583). Soluble DPPIV up-regulates the expression of the costimulatory molecule CD86 on monocytes through its dipeptidyl peptidase IV activity suggesting that soluble DPPIV enhances T cell immune response to recall antigen via its direct effect on antigen presenting cells (Ohnuma, et al., *J. Immunol.* 2001, 167(12), 6745-55). Consequently, DPPIV inhibition would be predicted to suppress certain immune responses and thus have therapeutic benefit in the treatment of immunomodulatory diseases. Therefore, the compounds of the present invention, including but not limited to those specified in the examples, can be used in the treatment of rheumatoid arthritis, multiple sclerosis, scleraderma, chronic inflammatory bowel disease or syndrome and allograft rejection in transplantation.

Chemokine receptors, especially CCR5 and CXCR4, act as cofactors for HIV-1 entry into CD4+ cells and their corresponding ligands can suppress HIV entry and thus replication. The CXC chemokine, stromal cell derived factor-1 (SDF-1) is a chemokine for resting T-lymphocytes and monocytes. SDF-1 exists as two splice variants, SDF-1alpha and SDF-1beta that differ by four additional C-terminal residues in SDF-1beta. Truncation of the N-terminal Lys-Pro-residues from both SDF-1 alpha and SDF-1 beta results in the loss of their chemotactic and antiviral activities in vitro (Ohtsuki, et al, *FEBS Lett.* 1998, 431, 236-40; Shioda, et al., *Proc. Natl. Acad. Sci.* 1998, 95(11), 6331-6; Proost, et al., *FEBS Lett.* 1998, 432, 73-6). DPPIV inactivates SDF-1 alpha as a ligand for CXCR4 that is a T cell chemotactic receptor as well as the major co-receptor for T-tropic HIV-1 strains. DPPIV inhibition would be predicted to increase full-length SDF-1 levels and thereby suppress HIV-1 entry into CXCR4+ cells. Therefore, the compounds of the present invention, including but not limited to those specified in the examples, can be used in the treatment of HIV infection (AIDS).

The loss of DPPIV activity in DPPIV-deficient F344 rats is associated with reduced stress-like responses in tasks such as the open field, social interaction and passive avoidance tests compared to wild-type animals (Karl, et al., *Physiology and Behavior* 2003, 80, 123-134). Consequently, inhibition of DPPIV activity is predicted to be anxiolytic. DPPIV inhibitors are efficacious in established models of psychosis including mescaline-induced scratching and amphetamine-induced hyperactivity models (Lautar, et al., *Brain Research* 2005, 1048, 177-184). Therefore, the compounds of the present invention, including but not limited to those specified in the examples, can be used in the treatment of anxiety, schizophrenia, bipolar disorder, and depression.

*Porphyromonas gingivalis* is a pathogen associated with adult peridontitis. *P. gingivalis* produces dipeptidyl peptidase IV, which acts as a virulence factor by contributing to the degradation of connective tissue and thus having a pathological role in the progression of periodontitis (Kumagai, et al., *Infection and Immunity* 2005, 73, 2655-2664). The catalytic pocket is identical between human DPPIV and *P. gingvalis* DPPIV. Thus, DPPIV inhibitors designed against human DPPIV are highly likely to inhibit *P. gingvalis* DPPIV. Therefore, the compounds of the present invention, including but not limited to those specified in the examples, can be used in the treatment of adult peridontitis.

In addition to GLP-1, GLP-2 is also secreted from endocrine L cells in response to nutrient intake. GLP-2 acts to slow gastric emptying, reduce gastric secretions, increase intestinal blood flow and stimulate the growth of the small and large intestine (Jeppesen, P B, et al., *Gut* 2005, 54, 1224-1231). GLP-2 promotes nutrient absorption by expansion of the mucosal epithelium in the small and large bowel by stimulation of crypt cell proliferation and inhibition of enterocyte apoptosis (Drucker, D J, et al., *Proc Natl Acad Sci,* 1996, 93, 7911-7916). GLP-2 improves intestinal wound healing (Bulut, K, et al., *Regulatory Peptides,* 2004, 121, 137-143) and improves intestinal function in short bowel syndrome patients (Jeppesen, P B, et al., *Gut* 2005, 54, 1224-1231). Like GLP-1, GLP-2 is degraded by the action of DPPIV. Consequently, agents that inhibit DPPIV activity would be predicted to elevate levels of active GLP-2. Therefore, the compounds of the present invention, including but not limited to those specified in the examples, can be used in the treatment of gastrointestinal diseases and disorders including short bowel syndrome and to improve nutrient uptake in the frail and elderly.

DPP-IV is a member of a family of dipeptidyl peptidases that share significant sequence homology. It has been suggested (Lankas, et al., *Diabetes* 2005, 54, 2988-2994) that selectivity can play a significant role in determining the safety profile of DPP-IV inhibitors. In particular, these workers have demonstrated that inhibitors of DPP8 and DPP9 demonstrate substantial toxicity in several preclinical toxicology models. Compounds of the present invention are highly selective for DPP-IV over DPP8 and DPP9, as demonstrated below:

Inhibition Constant Determination for DPP8 and DPP9:

Compounds of the present invention can be assayed for inhibitory activity against DPP8 or DPP9 using a procedure and reagents identical with that described above for DPP-IV, only substituting the appropriate enzyme. Representative data are shown in Tables 2 and 3 below.

TABLE 2

DPP-8 Inhibition of compounds of the present invention ($K_{IC}$ nM).

| | | | | |
|---|---|---|---|---|
| ND | ND | ND | ND | ND |
| ND | ND | ND | ND | ND |
| ND | ND | ND | ND | ND |
| ND | 2,430 | ND | ND | ND |
| ND | ND | ND | ND | 478 |
| ND | ND | ND | ND | 336 |
| ND | ND | ND | ND | 10,100 |
| 232 | ND | ND | ND | ND |
| ND | ND | ND | ND | ND |
| 20,000 | ND | ND | 13,500 | >30,000 |
| ND | ND | ND | 13,100 | 23,300 |
| 29,500 | ND | ND | ND | ND |

TABLE 2-continued

DPP-8 Inhibition of compounds of the present invention ($K_{IC}$ nM).

| | | | | |
|---|---|---|---|---|
| ND | ND | ND | 8,750 | ND |
| 516 | 559 | ND | ND | ND |
| ND | ND | ND | ND | ND |
| ND | ND | ND | ND | ND |
| ND | ND | ND | ND | ND |
| ND | ND | 5,130 | ND | 19,400 |
| ND | ND | ND | ND | ND |

TABLE 3

DPP-9 Inhibition of compounds of the present invention ($K_{IC}$ nM).

| | | | | |
|---|---|---|---|---|
| ND | ND | ND | ND | ND |
| ND | ND | ND | ND | ND |
| ND | ND | ND | ND | ND |
| ND | 721 | ND | ND | ND |
| ND | ND | ND | ND | 1,070 |
| ND | ND | ND | ND | 73 |
| ND | ND | ND | ND | 9,270 |
| 549 | ND | ND | ND | ND |
| ND | ND | ND | ND | ND |
| 4,350 | ND | ND | 2,960 | 23,900 |
| ND | ND | ND | >30,000 | 4,570 |
| 6,250 | ND | ND | ND | ND |
| ND | ND | ND | 13,800 | ND |
| 608 | 432 | ND | ND | ND |
| ND | ND | ND | ND | ND |
| ND | ND | ND | ND | ND |
| ND | ND | ND | ND | ND |
| ND | ND | ND | ND | ND |
| ND | ND | 2,870 | ND | 3,100 |
| ND | ND | ND | ND | ND |

Synthetic Methods

The compounds and processes of the present invention are better understood in connection with the following synthetic schemes, which together illustrate the methods by which the compounds of the invention can be prepared. The syntheses of compounds of formula (I) wherein the groups $R_1$, $R_2$, $Ar_1$, and G are as defined above unless otherwise noted, are exemplified in Schemes 1-5.

The compounds and processes of the present invention are better understood in connection with the following synthetic schemes, which together illustrate the methods by which the compounds of the invention can be prepared. Starting materials can be obtained from commercial sources or prepared by well-established literature methods known to those of ordinary skill in the art.

This invention is intended to encompass compounds having formula (I) when prepared by synthetic processes or by metabolic processes. Preparation of the compounds of the invention by metabolic processes includes those occurring in the human or animal body (in vivo) or processes occurring in vitro.

Scheme 1

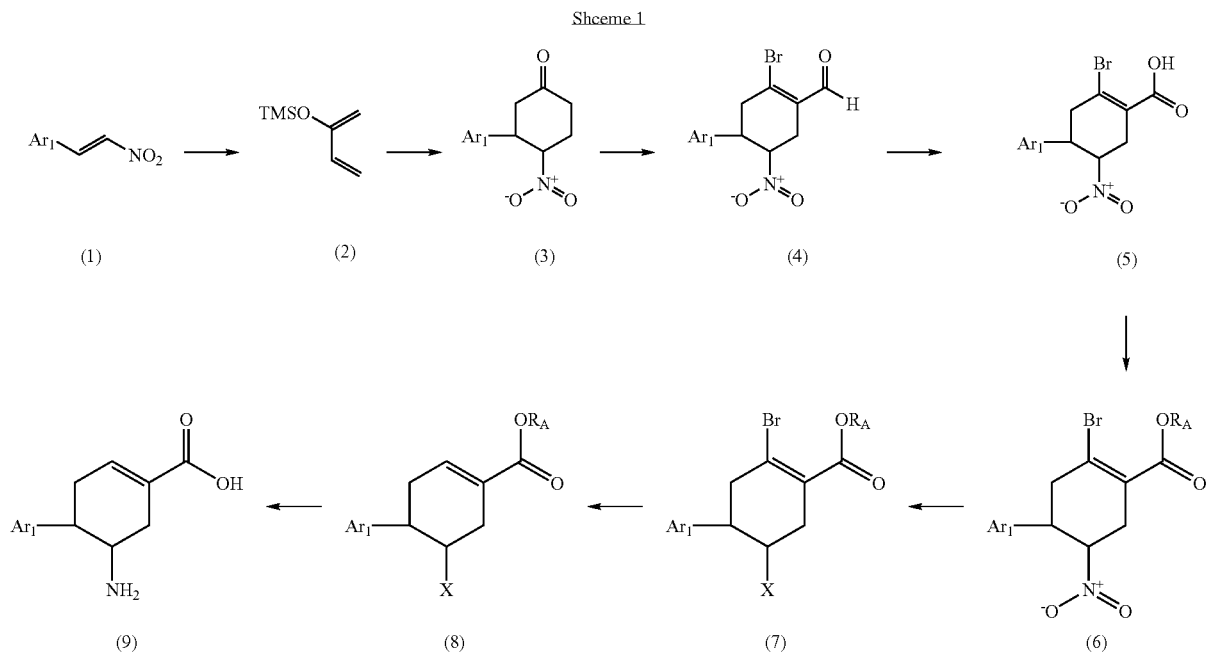

Compounds of formula (9) wherein $Ar_1$ is as defined in formula (I), can be prepared as shown in Scheme 1.

Alkenes of formula (1), purchased or prepared using methodologies known to one skilled in the art, can be reacted with dienes of formula (2) to afford cycloalkanes of formula (3). The reaction is generally conducted in a solvent such as, but not limited to, toluene, at a temperature from about 100° C. to about 150° C. in a sealed tube. Aldehydes of formula (4) can be obtained by reaction of cycloalkanes of formula (3) with a dehydrating agent such as, but not limited to phosphorous tribromide, and a formylating agent such as, but not limited to, N,N-dimethylformamide, in the presence of a solvent such as, but not limited to, dichloromethane. The reaction is generally conducted at a temperature of about 0° C. to about room temperature. Aldehydes of formula (3) can be oxidized to acids of formula (4) by reaction with an oxidizing agent such as, but not limited to, sodium chlorite in the presence of a buffer of about pH=7 and a solvent such as, but not limited to, dimethylsulfoxide. Esterification of acids of formula (5) provides esters of formula (6) wherein $R_A$ is alkyl. This can be achieved by reaction of (5) with (trimethylsilyl)diazomethane. Reduction of compounds of formula (6) using a reducing agent such as, but not limited to, zinc dust in the presence of an acid such as, but not limited to, acetic acid, at room temperature provided amines of formula (7) wherein X is $NH_2$. Protection of the amines to provide compounds of formula (7) wherein X is —NHC(O)$OR_B$ wherein $R_B$ is alkyl, benzyl or substituted benzyl can be achieved by, for example, reaction with di-tert-butyl dicarbonate or $R_B$OC(O)Cl wherein $R_B$ is alkyl, benzyl or substituted benzyl. Debromination of compounds of formula (7) wherein X is —N(H)C(O)$OR_B$ can be realized by reaction with formic acid in the presence a palladium reagent such as, but not limited to, bis(triphenylphosphine) palladium(II) chloride, to provide compounds of formula (8). Compounds of formula (8) wherein X is —N(H)C(O)$OR_B$ wherein $R_B$ is benzyl or substituted benzyl can be deprotected to provide compounds of formula (8) wherein X is $NH_2$ by hydrogenation. One example of such hydrogenation employs hydrogen source such as, hydrogen gas, in the presence of catalyst such as palladium on carbon. Compounds of formula (8) wherein X is —N(H)C(O)$OR_B$ wherein $R_B$ is alkyl can be converted to compounds of formula (8) wherein X is $NH_2$ by stirring with an acid such as, but not limited to, trifluoroacetic acid. Saponification of compounds of formula (8) wherein X is —$NH_2$, using conditions that are known to one skilled in the art (for example, reaction of (8) with an hydroxide base such as sodium hydroxide) provides compounds of formula (9).

Scheme 2

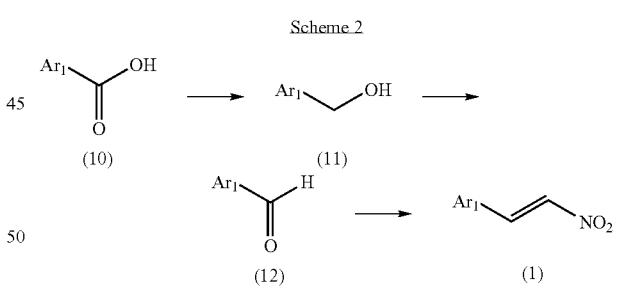

Alkenes of formula (1) can be prepared as outlined in Scheme 2.

Acids of formula (10) can be reduced to alcohols of formula (11) by reacting with a reducing agent such as, but not limited to, lithium aluminum hydride in a solvent such as, but not limited to, tetrahydrofuran, at a temperature from about −78° C. to about room temperature. Alcohols of formula (11) when subjected to oxidizing conditions such as, but not limited to, tetrapropylammonium perruthenate, provide aldehydes of formula (12), which in turn can be treated with ammonium acetate and nitromethane in a solvent such as, but not limited to, toluene, under heated conditions afford alkenes of formula (1).

Scheme 3

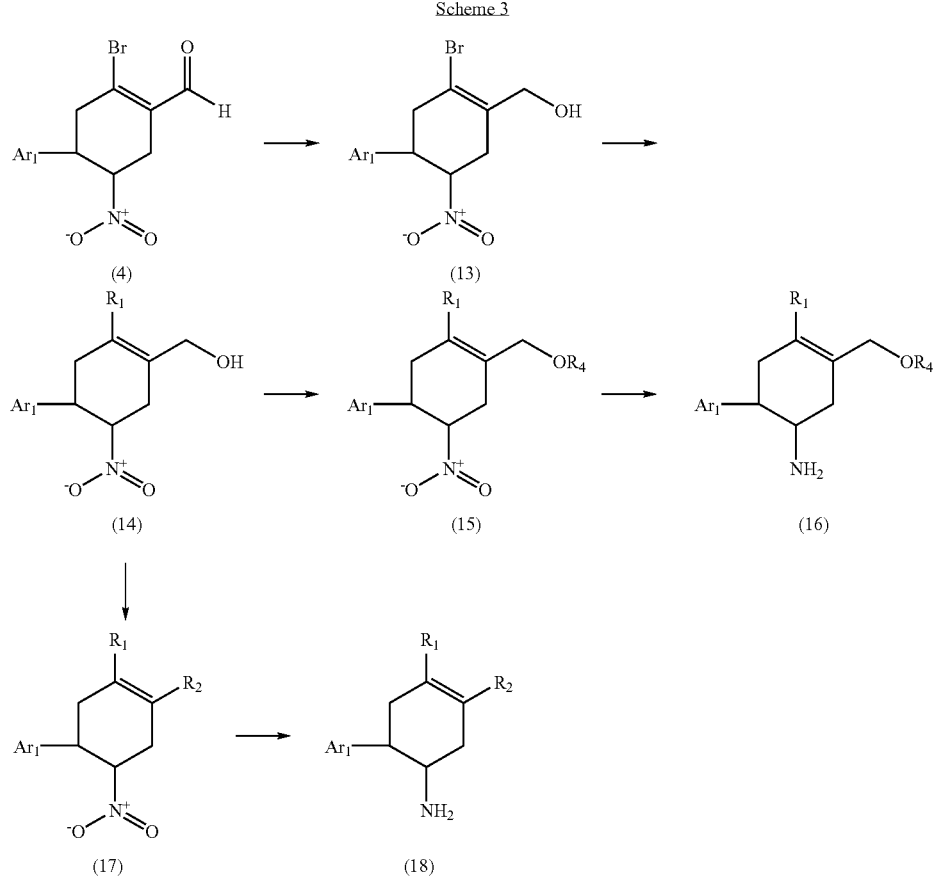

Compounds of formula (16) wherein $Ar_1$ and $R_4$ are as defined in formula (I) and $R_1$ is hydrogen, aryl, heterocycle, heteroaryl, cycloalkyl or cycloalkenyl can be synthesized as depicted in Scheme 3.

Compounds of formula (4) can be transformed to alcohols of formula (13) by subjecting to a reducing agent such as, but not limited to, sodium borohydride in a solvent such as, but not limited to alcohol (for example, ethanol, 2-propanol, methanol and the like, or mixture thereof). The reaction is generally conducted from about 0° C. to about room temperature. Compounds of formula (13) can be converted to compounds of formula (14) wherein $R_1$ is aryl, heterocycle, heteroaryl, cycloalkyl or cycloalkenyl, when reacted with compounds of formula $R_1X_1$ wherein $X_1$ is —B(OH)$_2$ or —Sn(alkyl)$_3$ in the presence of a palladium reagent such as, but not limited to, (triphenylphosphine)palladium (II) chloride, tetrakis(triphenylphosphine)palladium(0), tris(dibenzylideneacetone)dipalladium or palladium diacetate, optionally in the presence of a Pd ligand added such as (dicyclohexylphosphinyl)biphenyl, tri(2-furyl)phosphine or triphenyl arsine or trifurylphosphine, and optionally in a base such as, but not limited to, aqueous 0.2 M $K_3PO_4$. The reaction is generally conducted at a temperature from about room temperature to about 150° C., in a solvent such as, but not limited to, N,N-dimethylformamide.

Compounds of formula (14) wherein $R_1$ is hydrogen can be obtained by reacting compounds of formula (13) with formic acid in the presence a palladium reagent such as, but not limited to, bis(triphenylphosphine) palladium(II) chloride.

Alcohols of formula (14) can be converted to compounds of formula (15) by treatment with alcohols of formula $R_4OH$, in the presence of triphenylphosphine and di-t-butyl azidocarboxylate, in a solvent such as, but not limited to, toluene.

Reduction of compounds of formula (14) by treatment with a reducing agent such as, but not limited to, zinc dust in the presence of an acid such as, but not limited to, acetic acid, at room temperature, provided amines of formula (16).

Compounds of formula (17) wherein $Ar_1$ is as defined in formula (I), $R_1$ is hydrogen, aryl, heterocycle, heteroaryl, cycloalkyl or cycloalkenyl, and $R_2$ is —CH$_2$—NR$_5$R$_6$ wherein $R_5$ and $R_6$ are hydrogen, and $Ar_1$ is as defined in formula (I), can be prepared from compounds of formula (14) via (a) treatment with methanesulfonyl chloride and a base such as, but not limited to, triethyl amine, in a solvent such as, but not limited to, dichloromethane, and at a temperature from about 0° C. to about room temperature; (b) treating the product from step (a) with sodium azide in a solvent such as, but not limited to, N,N-dimethylformamide, at room temperature; and (c) reacting the product of step (b) with triphenylphosphine at a temperature from about room temperature to about 80° C.

Compounds of formula (17) wherein $R_1$ is hydrogen, aryl, heterocycle, heteroaryl, cycloalkyl or cycloalkenyl, and $R_2$ is —CH$_2$-heterocycle or —CH$_2$—NR$_5$R$_6$, and $Ar_1$, $R_5$ and $R_6$ are as defined in formula (I), can be prepared by reacting the product of step (a) as describe above, with an amine of formula N(H)R$_5$R$_6$ or a heterocycle containing at least one NH group in the ring (for example unsubstituted or substituted piperazine, piperidine, 1,3-thiazolidine, and the like).

Alternatively, Compounds of formula (17) wherein $R_1$ is hydrogen, aryl, heterocycle, heteroaryl, cycloalkyl or cycloalkenyl, and $R_2$ is —$CH_2$-heterocycle and $Ar_1$, $R_5$ and $R_6$ are as defined in formula (I), can be prepared by reacting compounds of formula (17) wherein $R_2$ is —$CH_2NH_2$ with a halide or triflate having formula heterocycle-X wherein X is Cl, Br, I or triflate, in the presence of a base such as, but not limited to, triethylamine, at a temperature from about room temperature to about 150° C.

Compounds of formula (17) can be converted to compounds of formula (18) by reacting with a reducing agent such as, but not limited to, zinc dust in the presence of an acid such as, but not limited to, acetic acid, at room temperature.

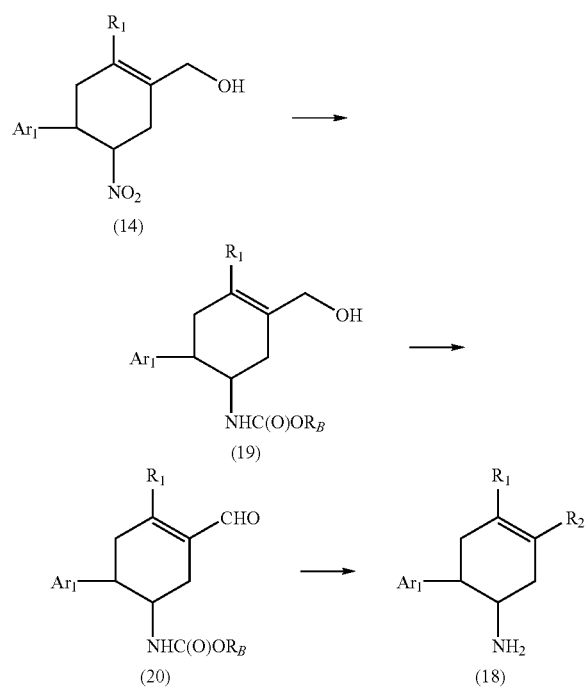

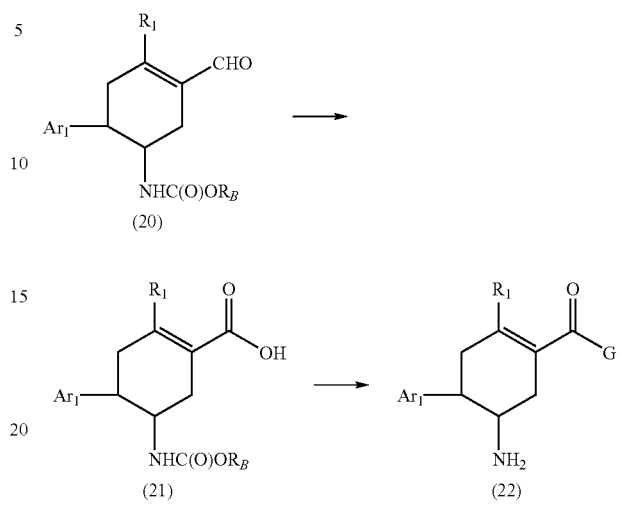

Compounds of formula (18) wherein $R_1$ is hydrogen, aryl, heterocycle, heteroaryl, cycloalkyl or cycloalkenyl, and $R_2$ is —$CH_2$-heterocycle or —$CH_2$—$NR_5R_6$ and $Ar_1$, $R_5$ and $R_6$ are as defined in formula (I), can be prepared from compounds of formula (14) as outlined in Scheme 4.

Compounds of formula (14) can be converted to compounds of formula (19) using the reaction conditions employed for the transformation of compounds of formula (6) to compounds of formula (7) as shown in Scheme 1. Compounds of formula (19) when (a) reacted with an oxidizing agent such as, but not limited to, Dess-Martin periodinane in a solvent such as, but not limited to, methylene chloride at about room temperature; and (b) treating the aldehydes obtained from step (a) with an acid such as, but not limited to, trifluoroacetic acid if $R_B$ is alkyl, or with a hydrogen source such as, but not limited to, hydrogen gas, in the presence of a catalyst such as, but not limited to, palladium on carbon if $R_B$ is unsubstituted or substituted benzyl, provides compounds of formula (18).

Compounds of formula (22) wherein $Ar_1$, and G are as defined in formula (I), and $R_1$ is hydrogen, aryl, heterocycle, heteroaryl, cycloalkyl or cycloalkenyl, can be prepared from compounds of formula (20) as outlined in Scheme 5.

Compounds of formula (20) when subjected to oxidation conditions such as the one utilized in the conversion of compounds of formula (4) to compounds of formula (5) shown in Scheme 1, provides compounds of formula (21).

Compounds of formula (21) can be converted to compounds of formula (22) by (a) activation of the acid moiety, for example with isobutyl chloroformate, 1-(3-dimethylaminopropyl)-3-ethylcarbodiimide hydrochloride (EDCI), O-benzotriazol-1-yl-N,N,N',N'-tetramethyluronium tetrafluoroborate )TBTU), or the like, optionally in the presence of a base such as triethylamine, with concurrent or subsequent addition of the coupling partner G-H; and (b) treating the product of step (a) with an acid such as trifluoroacetic acid if $R_B$ is alkyl, or a hydrogen source such as, but not limited to, hydrogen gas, in the presence of a catalyst such as, but not limited to, palladium on carbon if $R_B$ is unsubstituted or substituted benzyl.

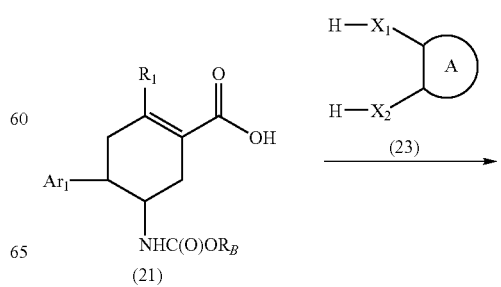

-continued

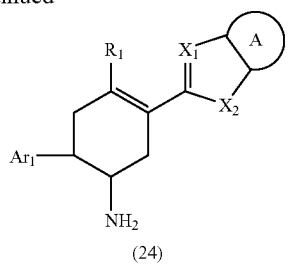

(24)

Compounds of formula (24) wherein $Ar_1$ is as defined in formula (I), $R_1$ is hydrogen, aryl, heterocycle, heteroaryl, cycloalkyl or cycloalkenyl, and A is an unsubstituted or substituted ring selected from the group consisting of phenyl, monocyclic heteroaryl, bicyclic aryl, bicyclic heteroaryl and bicyclic heterocycle, can be prepared from compounds of formula (21) as outlined in Scheme 6.

Compounds of formula (21) can be converted to compounds of formula (24) through a sequence of (a) condensation with an compound of formula (23) wherein $X_1$ is NH, and $X_2$ is NH, O or S, or $X_1$ is NH, O or S and $X_2$ is NH, in the presence of a dehydrating agent such as polyphosphoric acid at a temperature from about room temperature to about 200° C., and (b) an optional treatment of the product of step (a) with an acid such as trifluoroacetic acid if $R_B$ is alkyl, or a hydrogen source such as, but not limited to, hydrogen gas, in the presence of a catalyst such as, but not limited to, palladium on carbon if $R_B$ is unsubstituted or substituted benzyl.

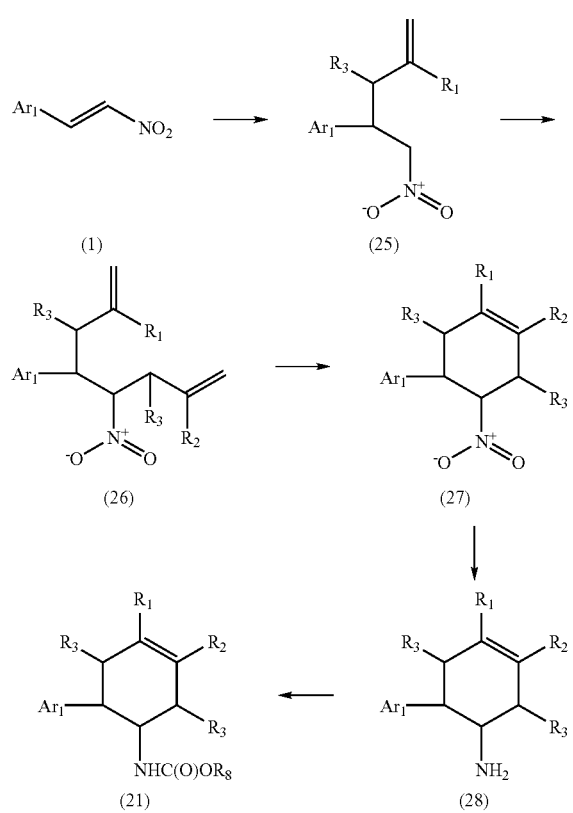

Compounds of formula (21) can alternatively be prepared as described in Scheme 7. Michael addition of an allylic organometallic reagent, for example allyl magnesium chloride or the like, to nitrosytrene (1) provides olefin (25). Alkylation of (25) with an allylic electrophile, for example, methyl 2-bromomethyl acrylate or the like, using a base such as sodium hydroxide or the like, leads to the formation of diene (26). Olefin metathesis of (26) using a ruthenium, molybdenum, or tungsten catalyst such as Grubbs' first- or second-generation catalyst or catMETium or the like, produces cyclohexene (27). Reduction of the nitro group, for example using catalytic hydrogenation or zinc metal or iron metal or the like, provides the amine (28), which is subsequently protected by reaction with di-tert-butyldicarbonate or benzylchloroformate or the like to give (21). Compound (21) can be further processed as described in Scheme 5 or Scheme 6.

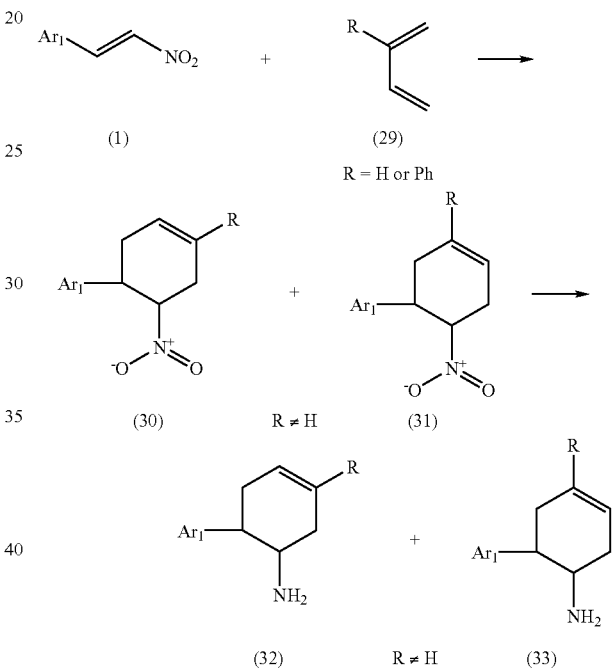

Compounds of formula (32) and (33) can be synthesized according to Scheme 8. Nitrostyrene (1) and 1,3-butadiene (either substituted or unsubstituted) of formula (29) underwent thermal Diels-Alder reaction to afford regioisomers of cyclohexene (30) and (31) when R≠H. The nitro group was then reduced with an appropriate metal, e.g., Zinc, to give the desired products (32) and (33).

The present invention will now be described in connection with certain preferred embodiments, which are not intended to limit its scope. On the contrary, the present invention covers all alternatives, modifications, and equivalents as can be included within the scope of the claims. Routine experimentation, including appropriate manipulation of the reaction conditions, reagents used and sequence of the synthetic route, protection of any chemical functionality that can not be compatible with the reaction conditions, and deprotection are included in the scope of the invention. Synthesis of the compounds of formula (I) can be accomplished by methods analogous to those described above and in the following examples. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

The compounds and processes of the present invention are better understood by reference to the following examples, which are intended as an illustration of and not a limitation upon the scope of the invention. Further, all citations herein are incorporated by reference.

EXPERIMENTALS

Example 1 trans-6-(2-chlorophenyl)cyclohex-3-en-1-amine

Example 1A trans-1-chloro-2-(6-nitrocyclohex-3-en-1-yl)benzene

A 10 mL solution of 1:1 1,3-butadiene and toluene stored at −20° C. and 2-chloro-β-nitrostyrene (2.0 g, 11 mmol) were added to a pressure tube and sealed. The solution was heated to 110° C. and stirred for three days. The reaction mixture was cooled to room temperature, concentrated, and the residue was crystallized from hexanes to give the title compound. $^1$H NMR (300 MHz, CDCl$_3$) δ ppm 7.35-7.38 (m, 1H), 7.15-7.29 (m, 3H), 5.71-5.84 (m, 2H), 5.09-5.16 (m, 1H), 4.04-4.13 (m, 1H), 2.76-2.84 (m, 2H), 2.54-2.60 (m, 1H), 2.19-2.28 (m, 1H).

Example 1B trans-6-(2-chlorophenyl)cyclohex-3-en-1-amine

To a solution of Example 1A (100 mg, 0.042 mmol) in a 2 mL solution of 1:1 aqueous concentrated HCl in methanol at 0° C., Zn dust (32 mg, 0.5 mmol) was added in several portions. The solution was allowed to warm to room temperature over three hours. Afterwards, the solution was carefully basified with saturated NaHCO$_3$. The mixture was extracted with ethyl acetate, concentrated, taken up in dichloromethane, and filtered through Celite. Concentration of the filtrate gave the title compound. $^1$H NMR (300 MHz, C$_5$D$_5$N) δ ppm 7.41-7.43 (m, 2H), 7.24-7.28 (m, 1H), 7.12-7.14 (m, 1H), 5.70-5.73 (m, 2H), 3.49-3.54 (m, 2H), 2.55-2.58 (m, 1H), 2.37-2.41 (m, 1H), 2.14-2.24 (m, 2H). MS (ESI+) m/z 208 (M+H)$^+$ Example 2 trans-6-(2,4-dichlorophenyl)cyclohex-3-en-1-amine

Example 2A trans-2,4-dichloro-1-(6-nitrocyclohex-3-en-1-yl)benzene

A 10 mL solution of 1:1 1,3-butadiene in toluene stored at −20° C. and 2,4-chloro-β-nitrostyrene (2.0 g, 9.6 mmol) were added to a pressure tube and sealed. The solution was heated to 110° C. and stirred for three days. The reaction mixture was cooled to room temperature, concentrated and the residue was crystallized from hexanes to give the title compound. $^1$H NMR (300 MHz, CDCl$_3$) δ ppm 7.38-7.39 (m, 1H), 7.19-7.23 (m, 2H), 5.71-5.83 (m, 2H), 5.04-5.13 (m, 1H), 3.99-4.08 (m, 1H), 2.72-2.83 (m, 2H), 2.52-2.61 (m, 1H), 2.16-2.25 (m, 1H).

Example 2B trans-6-(2,4-dichlorophenyl)cyclohex-3-en-1-amine

To a solution of Example 2A (100 mg, 0.037 mmol) in a 2 mL solution of 1:1 aqueous concentrated HCl in methanol at 0° C., Zn dust (32 mg, 0.5 mmol) was added in several portions. The solution was allowed to warm to room temperature over three hours, after which the solution was carefully basified with saturated NaHCO$_3$. The mixture was extracted with ethyl acetate, concentrated, taken up in dichloromethane, and filtered through Celite. Concentration of the filtrate gave the title compound. $^1$H NMR (300 MHz, C$_5$D$_5$N) δ ppm 7.48 (s, 1H), 7.31-7.33 (m, 2H), 5.68-5.73 (m, 2H), 3.28-3.37 (m, 2H), 2.45-2.49 (m, 1H), 2.29-2.36 (m, 1H), 2.06-2.13 (m, 2H). MS (ESI+) m/z 243 (M+H)$^+$.

Example 3 trans-6-(2-chloro-4-fluorophenyl)cyclohex-3-en-1-amine

Example 3A trans-2-chloro-4-fluoro-1-(6-nitrocyclohex-3-en-1-yl)benzene

A 10 mL solution of 1:1 1,3-butadiene in toluene stored at −20° C. and 2-chloro-4-fluoro-β-nitrostyrene (2.0 g, 10 mmol) were added to a pressure tube and sealed. The solution was heated to 110° C. and stirred for three days. The reaction mixture was cooled to room temperature, concentrated and the residue was crystallized from hexanes to give the title compound. $^1$H NMR (300 MHz, CDCl$_3$) δ ppm 7.23-7.28 (m, 1H), 7.11-7.25 (m, 3H), 6.94-7.01 (m, 1H), 5.73-5.83 (m, 2H), 5.04-5.13 (m, 1H), 3.99-4.08 (m, 1H), 2.71-2.82 (m, 2H), 2.51-2.61 (m, 1H), 2.15-2.26 (m, 1H).

Example 3B trans-6-(2-chloro-4-fluorophenyl)cyclohex-3-en-1-amine

To a solution of Example 3A (100 mg, 0.039 mmol) in 2 mL of 1:1 aqueous concentrated HCl in methanol at 0° C., Zn dust (32 mg, 0.5 mmol) was added in several portions. The solution was allowed to warm to room temperature over three hours, after which the solution was carefully basified with saturated NaHCO$_3$. The mixture was extracted with ethyl acetate, concentrated, taken up in dichloromethane, and filtered through Celite. Concentration of the filtrate gave the title compound. $^1$H NMR (300 MHz, C$_5$D$_5$N) δ ppm 7.33-7.35 (m, 1H), 7.22-7.28 (m, 1H), 7.06-7.10 (m, 1H), 5.68-5.77 (m, 2H), 3.22-3.37 (m, 2H), 2.43-2.48 (m, 1H), 2.29-2.36 (m, 1H), 2.06-2.14 (m, 2H). MS (ESI+) m/z 227 (M+H)$^+$.

Example 4 trans-6-(2-chlorophenyl)-3-phenylcyclohex-3-en-1-amine compound with trans-6-(2-chlorophenyl)-4-phenylcyclohex-3-en-1-amine

Example 4A 1-phenyl-2-(trimethylsilyl)ethanol

To benzaldehyde (2.17 g, 20.4 mmol) in 20 mL of ether, 1 M (trimethylsilyl)methyl magnesium chloride solution in ether (28.6 mL) was added at 0° C. After two hours of stirring at 0° C., a saturated $NH_4Cl$ solution was added and the mixture was extracted with ether (3×). The combined organic extract was dried ($Na_2SO_4$), filtered, and concentrated to give the title product (4.12 g).

Example 4B 1-phenyl-2-(trimethylsilyl)ethanone

Example 4A (4.12 g) in 60 mL of $CH_2Cl_2$ was treated with pyridinium dichromate (11.5 g, 1.5 eq.). After one hour of stirring at room temperature, another 3.2 g of pyridinium dichromate was added. After the reaction was done, the mixture was filtered through Celite. The filtrate was concentrated and filtered through a silica gel plug. The filtrate was concentrated again, and the resulting oil was purified by column chromatography (eluting with 5-10% ethyl acetate/hexane) to give the title compound. $^1H$ NMR (500 MHz, $CDCl_3$) δ ppm -0.01 (s, 9H), 2.67 (s, 2H), 7.33-7.41 (m, 2H), 7.42-7.49 (m, 1H), 7.79-7.85 (m, 2H).

Example 4C 2-phenyl-1-(trimethylsilyl)but-3-en-2-ol

Example 4B (422 mg, <2.3 mmol) in 4.5 mL of ether was cooled to 0° C. Then, vinyl magnesium bromide solution (1M in tetrahydrofuran, 4.4 mL) was added to the solution. After the reaction was done, a saturated $NH_4Cl$ solution was added and the mixture was extracted with ether (3×). The combined organic extracts were dried ($Na_2SO_4$), filtered, and concentrated. The resulting oil was purified by column chromatography (eluting with 5-10% ethyl acetate/hexane) to give the title compound (328 mg, 65% two steps). $^1H$ NMR (500 MHz, $CDCl_3$) δ ppm 0.01 (s, 9H), 1.51 (d, J=14.7 Hz, 1H), 1.58 (d, J=15 Hz, 1H), 5.17 (dd, J=10.61, 1.25 Hz, 1H), 5.35 (dd, J=17.16, 0.94 Hz, 1H), 6.34 (dd, J=17.16, 10.61 Hz, 1H), 7.30-7.37 (m, 1H), 7.39-7.46 (m, 2H), 7.53-7.59 (m, 2H).

Example 4D (1-methyleneprop-2-enyl)benzene

Example 4C (409 mg, 1.85 mmol) was mixed in 4 mL of acetic acid saturated with sodium acetate and then heated to 60° C. After stirring for 45 minutes at 60° C., the mixture was cooled to room temperature and then added into a mixture of saturated $NaHCO_3$ and ether. The mixture was extracted with ether (3×). The combined organic extract was dried ($Na_2SO_4$), filtered, and concentrated to give the title product (167 mg). $^1H$ NMR (300 MHz, $CDCl_3$) δ ppm 5.14-5.34 (m, 4H), 6.62 (dd, J=17.29, 11.19 Hz, 1H), 7.29-7.37 (m, 5H).

Example 4E trans-1-chloro-2-[-6-nitro-4-phenylcyclohex-3-en-1-yl]benzene compound with trans-1-chloro-2-[6-nitro-3-phenylcyclohex-3-en-1-yl]benzene Example 4D (104 mg, 0.8 mmol), 2-chloro-β-nitrostyrene (124 mg, 0.67 mmol) and 1.2 mL of toluene were mixed in a pressure reaction tube. The tube was heated to 125° C. and stirred for two days. The mixture was cooled to room temperature, concentrated, and then purified by column chromatography (eluting with 10% ethyl acetate/hexanes) to afford the title compounds as a mixture (126 mg, 60%). $^1H$ NMR (400 MHz, $CDCl_3$) δ ppm 2.5 and 2.7 (m, 1H), 2.75-3.07 (m, 2H), 3.2-3.3 and 3.1-3.15 (m, 1H), 4.07-4.35 (m, 1H), 5.16-5.35 (m, 1H), 6.11 and 6.18 (m, 1H), 7.16-7.29 (m, 3H), 7.29-7.42 (m, 6H).

Example 4F trans-6-(2-chlorophenyl)-3-phenylcyclohex-3-en-1-amine compound with trans-6-(2-chlorophenyl)-4-phenylcyclohex-3-en-1-amine To Example 4E (110 mg, 0.35 mmol), zinc dust (106 mg, 7 eq.) in 2 mL of methanol, 1 mL of 1,4-dioxane, 2 mL of 6N HCl were added. The mixture was then heated to 75° C. After the reaction was done, the mixture was cooled to room temperature and purified by reverse-phase high pressure liquid chromatography, eluting with 0-70% acetonitrile/water with 0.1% trifluoroacetic acid to give the title products. $^1H$ NMR (300 MHz, methanol-$d_4$) δ ppm 2.40-2.61 (m, 1H), 2.62-3.01 (m, 3H), 3.62-3.84 (m, 1H), 3.91-4.11 (m, 1H), 6.29 and 6.14 (dd, m, 37:63, 1H), 7.20-7.39 (m, 4H), 7.39-7.47 (m, 3H), 7.48-7.57 (m, 2H). MS (DCI) m/z 284/286 $(M+H)^+$.

Example 5 trans-6-(2,4-dichlorophenyl)-3-phenylcyclohex-3-en-1-amine with trans-6-(2,4-dichlorophenyl-4-phenyl-cyclohex-3-en-1-amine The title compound was synthesized by substituting 2-chloro-β-nitrostyrene in Example 4E with 2,4-dichloro-β-nitrostyrene as a mixture. $^1H$ NMR (500 MHz, DMSO-$d_6$) δ ppm 2.09-2.30 (m, 1H), 2.32-2.49 (m, 1H), 2.53-2.81 (m, 2H), 3.13-3.4 (m, 2H), 6.17 (d, J=2.18 Hz, 1H), 7.20-7.37 (m, 3.35H), 7.38-7.47 (m, 3H), 7.47-7.55 (m, 1H), 7.59 (dd, J=3.74, 2.18 Hz, 0.65H). MS (DCI) m/z 318 $(M+H)^+$.

Example 6 trans-6-(2-chlorophenyl)-3-(4-methoxyphenyl)cyclohex-3-en-1-amine with trans-6-(2-chlorophenyl)-4-(4-methoxyphenyl)cyclohex-3-en-1-amine

Example 6A 3-(4-methoxyphenyl)-2,3-dihydrothiophene 1,1-dioxide

4-Methoxyphenyldiazonium borate (688 mg, 3.1 mmol), 2,5-dihydrothiophene-1,1-dioxide (465 mg, 3.94 mmol), and palladium(II) acetate (20.8 mg, 3 mol %) were mixed in 6 mL of methanol and then heated to reflux. Two additional portions of the diazonium borate (300 mg and 400 mg) along with 20 mg of palladium(II) acetate were added after one hour and five hours, respectively. After stirring overnight at reflux, the reaction mixture was cooled to room temperature, concentrated, and purified by column chromatography (eluting with 40-45% ethyl acetate/hexane) to give the title compound (644 mg). $^1$H NMR (300 MHz, CDCl$_3$) δ ppm 3.14 (dd, J=13.90, 4.75 Hz, 1H), 3.69 (dd, J=13.73, 8.65 Hz, 1H), 3.80 (s, 3H), 4.25-4.35 (m, 1H), 6.65-6.78 (m, 2H), 6.89 (d, J=8.48 Hz, 2H), 7.15 (d, J=8.48 Hz, 2H). MS (DCI) m/z 242 (M+NH$_4$)$^+$.

Example 6B 3-(4-methoxyphenyl)-2,5-dihydrothiophene 1,1-dioxide

Example 6A (617 mg) was mixed with 10 mL of CH$_2$Cl$_2$ and 3.75 mL of triethyl amine and then heated to reflux and stirred for six and a half hours. The mixture was cooled to room temperature and concentrated to give the title compound. $^1$H NMR (300 MHz, CDCl$_3$) δ ppm 3.83 (s, 3H), 3.97-4.04 (m, 2H), 4.11 (q, J=1.58 Hz, 2H), 6.18-6.25 (m, J=1.86, 1.86 Hz, 1H), 6.91 (d, J=8.82 Hz, 2H), 7.30 (d, J=8.82 Hz, 2H).

Example 6C trans-1-chloro-2-[3-(4-methoxyphenyl)-6-nitrocyclohex-3-en-1-yl]benzene compound with trans-1-chloro-2-[4-(4-methoxyphenyl)-6-nitrocyclohex-3-en-1-yl]benzene Example 6B (258 mg, 1.04 mmol), dihydroquinone (5 mg), and 2-chloro-β-nitrostyrene (136 mg, 0.74 mmol) were mixed in 2 mL of toluene in a pressure reaction tube. The tube was heated at 125° C. overnight. The mixture was cooled to room temperature, concentrated, and then purified by column chromatography (eluting with 10% ethyl acetate/hexane) to give the title compound (178 mg). $^1$H NMR (300 MHz, CDCl$_3$) δ ppm 2.31-2.72 (m, 1H), 2.71-2.87 (m, 0.34H), 2.87-3.03 (m, 2H), 3.04-3.28 (m, 1.66H), 3.81 and 3.83 (s, 3H), 4.09-4.34 (m, 1H), 5.13-5.36 (m, 1H), 6.02 and 6.09 (m, 1H), 6.82-6.94 (m, 2H), 7.16-7.44 (m, 6H). MS (DCI) m/z 361 (M+NH$_4$)$^+$.

Example 6D trans-6-(2-chlorophenyl)-4-(4-methoxyphenyl)cyclohex-3-en-1-amine and trans-6-(2-chlorophenyl)-3-(4-methoxyphenyl)cyclohex-3-en-1-amine Example 6C (163 mg, 0.47 mmol) and zinc dust (310 mg, 10 eq.) were mixed in 2 mL of 1,4-dioxane. Then 1.5 mL of 6N HCl was added. The mixture was heated to 70° C. and stirred for one hour. The mixture was then cooled to room temperature, poured into a mixture of saturated NaHCO$_3$ and ethyl acetate. The organic layer was separated and the water layer was extracted with ethyl acetate (2×). The combined organic layers were dried (Na$_2$SO$_4$), filtered, and concentrated to give the title compounds. $^1$H NMR (300 MHz, methanol-d$_4$) δ ppm 2.13-2.28 (m, 0.62H), 2.33-2.93 (m, 3.4H), 3.33-3.52 (m, 2H), 3.79 and 3.77 (s, 3H), 5.99-6.12 (m, 1H), 6.81-6.93 (m, 2H), 7.18-7.41 (m, 4H), 7.40-7.50 (m, 2H). MS (DCI) m/z 314 (M+H)$^+$.

Example 7

4-{[trans-5-amino-4-(2,4-dichlorophenyl)-2-phenyl-cyclohex-1-en-1-yl]methoxy}benzonitrile Example 7A trans-3-(2,4-dichlorophenyl)-4-nitrocyclohexanone In a high pressure tube, 2,4-dichloro-β-nitrostyrene (3.14 g, 14.4 mmol) and 2-trimetylsiloxy-1,3-butadiene (5 ml, 28.8 mmol) were dissolved in toluene (10 mL). The tube was sealed and heated to 120° C. for two days. The crude product was obtained after the solvent was removed under reduced pressure.

To a CH$_2$Cl$_2$ (5 mL) solution of the crude product at room temperature, trifluoroacetic acid (5 mL) was added slowly. The reaction mixture was stirred for ten minutes and then concentrated under reduced pressure to give the crude product as dark brown oil. The residue was chromatographed on a Biotage flash 40 M column eluting with 70% hexane/30% ethyl acetate to afford the title compound (2.54 g, 61%). $^1$H NMR (300 MHz, CDCl$_3$) δ ppm 7.14-7.35 (m, 3H), 5.13-5.34 (m, 1H), 4.19-4.36 (m, 1H), 2.43-2.87 (m, 6H). MS (DCI) m/z 305 (M+NH$_4$)$^+$.

Example 7B trans-2-bromo-4-(2,4-dichlorophenyl)-5-nitrocyclohex-1-ene-1-carbaldehyde To a cold solution (0° C.) of CH$_2$Cl$_2$ (30 mL) and N,N-dimethylformamide (2.33 mL, 30 mmol), PBr$_3$ (2.36 mL, 25 mmol) was added slowly. The reaction mixture was stirred at 0° C. for one hour and then Example 7A (2.88 g, 10 mmol) in CH$_2$Cl$_2$ (10 mL) was added dropwise. The reaction was allowed to warm up to room temperature and stirred overnight. It was quenched with ice carefully, basified with solid NaHCO$_3$ until the pH reached 7, and extracted with ethyl acetate (3×50 mL). The combined ethyl acetate layers were washed with water and brine, dried over sodium sulfate, filtered, concentrated under reduced pressure, and purified by flash chromatography with 30% ethyl acetate/hexane to provide the title compound (1.3 g, 34%). $^1$H NMR (300 MHz, CDCl$_3$) δ ppm 10.03 (s, 1H), 7.38-7.50 (m, 1H), 7.25-7.32 (m, 1H), 7.10-7.20 (m, 1H), 5.02-5.16 (m, 1H), 4.17-4.32 (m, 1H), 2.80-3.35 (m, 4H). MS (DCI) m/z 397 (M+H)$^+$.

Example 7C

[trans-2-bromo-4-(2,4-dichlorophenyl)-5-nitrocyclohex-1-en-1-yl]methanol

To a cold (0° C.) ethanol/2-propanol (3 mL/3 mL) solution of Example 7B (758 mg, 2 mmol) under N$_2$ flow, NaBH$_4$ (80 mg, 2.1 mmol) was added. The reaction mixture was stirred and the temperature was allowed to increase from 0° C. to room temperature over two hours. The solution was treated with saturated NH$_4$Cl, and diluted with ethyl acetate. The organic layer was washed with water and brine, dried over sodium sulfate, and then filtered. The filtrate was concentrated under reduced pressure and then purified by flash chromatography with 30% ethyl acetate/hexane to provide the title compound (642 mg, 84%). $^1$H NMR (300 MHz, CDCl$_3$)

δ ppm 7.39-7.51 (m, 1H), 7.26-7.32 (m, 1H), 7.11-7.22 (m, 1H), 5.04-5.20 (m, 1H), 4.31-4.45 (m, 2H), 4.14-4.27 (m, 1H), 2.59-3.32 (m, 4H). MS (DCI) m/z 399 (M+H)$^+$.

Example 7D

[trans-4-(2,4-dichlorophenyl)-5-nitro-2-phenylcyclohex-1-en-1-yl]methanol

In a high pressure tube, Example 7C (114 mg, 0.3 mmol), phenylboronic acid (44 mg, 0.45 mmol), bis(triphenylphosphine)palladium(II) dichloride (11 mg, 0.015 mmol) and 2N Na$_2$CO$_3$ (0.3 mL, 0.6 mmol) were dissolved in a mixture of 1,2-dimethoxyethane/ethanol/H$_2$O (1.4 mL/0.4 mL/0.6 mL). The tube was sealed, heated to 85° C. and stirred for four hours. The reaction mixture was cooled to room temperature, filtered through Celite, and washed with ethyl acetate. The filtrate was concentrated under reduced pressure and purified by flash chromatography, eluting with 30% ethyl acetate/hexane to provide the title compound (82 mg, 73%). $^1$H NMR (400 MHz, CDCl3) δ ppm 7.09-7.51 (m, 8H), 5.15-5.31 (m, 1H), 4.12-4.28 (m, 1H), 4.00-4.14 (m, 2H), 2.95-3.17 (m, 2H), 2.77-2.90 (m, 1H), 2.40-2.60 (m, 1H). MS (DCI) m/z 395 (M+NH$_4$)$^+$.

Example 7E

4-{[trans-4-(2,4-dichlorophenyl)-5-nitro-2-phenylcyclohex-1-en-1-yl]methoxy}benzonitrile In a high pressure tube, Example 7D (52 mg, 0.137 mmol), 4-cyanophenol (21 mg, 0.172 mmol), triphenylphosphine (58 mg, 0.22 mmol) and di-t-butyl azodicarboxylate (51 mg, 0.22 mmol) were dissolved in toluene (1 mL). The stirred tube was sealed and heated to 85° C. overnight. The reaction mixture was cooled to room temperature, concentrated under reduced pressure and purified by flash chromatography (eluting with 30% ethyl acetate/hexane to provide the title compound (45 mg, 68%)). $^1$H NMR (300 MHz, CDCl$_3$) δ ppm 7.48-7.59 (m, 2H), 7.29-7.45 (m, 4H), 7.21-7.28 (m, 4H), 6.74-6.89 (m, 2H), 5.18-5.31 (m, 1H), 4.38-4.55 (m, 2H), 4.16-4.30 (m, 1H), 3.01-3.15 (m, 2H), 2.82-2.99 (m, 1H), 2.47-2.65 (m, 1H). MS (ESI) m/z 478 (M+H)$^+$.

Example 7F

4-{[trans-5-amino-4-(2,4-dichlorophenyl)-2-phenylcyclohex-1-en-1-yl]methoxy}benzonitrile To a solution of Example 7E (42 mg, 0.088 mmol) in a mixture of methanol/acetic acid (0.75 mL/0.75 mL), Zn powder (57 mg, 0.88 mmol) was added at room temperature. The reaction mixture was stirred for thirty minutes, filtered, concentrated under reduced pressure and purified by high-pressure liquid chromatography (eluting with 0-70% acetonitrile/water and 0.1% trifluoroacetic acid to provide the title compound (30 mg, 76%)). $^1$H NMR (400 MHz, CDCl$_3$) δ ppm 7.44-7.53 (m, 2H), 7.24-7.39 (m, 4H), 7.12-7.23 (m, 4H), 6.68-6.82 (m, 2H), 4.40-4.51 (m, 1H), 4.27-4.40 (m, 1H), 2.68-2.88 (m, 2H), 2.45-2.64 (m, 2H). MS (ESI) m/z 449 (M+H)$^+$.

Example 8

4-{[trans-5-amino-4-(2,4-dichlorophenyl)-2-pyridin-3-ylcyclohex-1-en-1-yl]methoxy}benzonitrile Example 8A

[trans-4-(2,4-dichlorophenyl)-5-nitro-2-pyridin-3-ylcyclohex-1-en-1-yl]methanol

In a high pressure tube, Example 7C (485 mg, 1.27 mmol), 3-pyridine boronic acid (233 mg, 1.91 mmol), bis(triphenylphosphine)palladium(II) dichloride (45 mg, 0.064 mmol), and 2N Na$_2$CO$_3$ (1.27 mL, 2.54 mmol) were dissolved in mixture of 1,2-dimethoxyethane/ethanol/H$_2$O (5.6 mL/1.6 mL/2.4 mL). The tube was sealed, heated to 85° C., and stirred overnight. The reaction mixture was cooled to room temperature, filtered through Celite, and washed with ethyl acetate. The filtrate was concentrated under reduced pressure and purified by flash chromatography (eluting with 30% ethyl acetate/hexane) to provide the title compound (310 mg, 64%). $^1$H NMR (300 MHz, CDCl$_3$) δ ppm 7.28-7.74 (m, 7H), 5.16-5.30 (m, 1H), 4.11-4.31 (m, 1H), 4.01-4.10 (m, 2H), 2.98-3.21 (m, 2H), 2.73-2.88 (m, 1H), 2.38-2.60 (m, 1H). MS (DCI) m/z 379 (M+H)$^+$.

Example 8B

4-{[trans-4-(2,4-dichlorophenyl)-5-nitro-2-pyridin-3-ylcyclohex-1-en-1-yl]methoxy}benzonitrile In a high pressure tube, Example 8A (52 mg, 0.137 mmol), 4-cyanophenol (21 mg, 0.172 mmol), triphenylphosphine (58 mg, 0.22 mmol) and di-t-butyl azodicarboxylate (51 mg, 0.22 mmol) were dissolved in toluene (1 mL). The stirred tube was sealed and heated to 85° C. overnight. The reaction mixture was cooled to room temperature, concentrated under reduced pressure and purified by flash chromatography (eluting with 30% ethyl acetate/hexane) to provide the title compound (43 mg, 68%). $^1$H NMR (300 MHz, CDCl3) δ ppm 7.61-7.76 (m, 2H), 7.35-7.61 (m, 7H), 6.78-7.00 (m, 2H), 5.22-5.35 (m, 1H), 4.35-4.48 (m, 2H), 4.19-4.31 (m, 1H), 3.07-3.20 (m, 2H), 2.82-2.96 (m, 1H), 2.50-2.67 (m, 1H). MS (ESI) m/z 480 (M+H)$^+$.

Example 8C

4-{[trans-5-amino-4-(2,4-dichlorophenyl)-2-pyridin-3-ylcyclohex-1-en-1-yl]methoxy}benzonitrile To a solution of Example 8B (40 mg, 0.083 mmol) in a mixture of methanol/acetic acid (0.5 mL/0.5 mL), Zn powder (54 mg, 0.83 mmol) was added at room temperature. The reaction mixture was stirred for thirty minutes, filtered, concentrated under reduced pressure and purified by high pressure liquid chromotography (eluting with 0-70% acetonitrile/water and 0.1% trifluoroacetic acid) to provide the title compound (20 mg, 53%). $^1$H NMR (400 MHz, DMSO-d$_6$) δ ppm 7.34-7.54 (m, 2H), 6.25-6.98 (m, 9H), 5.82-5.96 (m, 2H), 5.73-5.83 (m, 1H), 3.30-3.47 (m, 1H), 1.28-1.80 (m, 4H). MS (ESI) m/z 450 (M+H)$^+$.

Example 9 trans-methyl 3-{[5-amino-4-(2,4-dichlorophenyl)-2-pyridin-3-ylcyclohex-1-en-1-yl]methoxy}benzoate

Example 9A methyl 3-{[trans-4-(2,4-dichlorophenyl)-5-nitro-2-pyridin-3-ylcyclohex-1-en-1-yl]methoxy}benzoate In a high pressure tube, Example 8A (52 mg, 0.137 mmol), 3-hydroxy-benzoic acid methyl ester (27 mg, 0.172 mmol), triphenylphosphine (58 mg, 0.22 mmol) and di-t-butyl azodicarboxylate (51 mg, 0.22 mmol) were dissolved in toluene (1 mL). The stirred tube was sealed and heated to 85° C. overnight. The reaction mixture was cooled to room temperature, concentrated under reduced pressure and purified by flash chromatography (eluting with 30% ethyl acetate/hexane) to provide the title compound (39 mg, 56%). $^1$H NMR (400 MHz, CDCl$_3$) δ ppm 8.41-8.73 (m, 2H), 7.14-7.75 (m, 8H), 6.95-7.10 (m, 1H), 5.18-5.35 (m, 1H), 4.36-4.51 (m, 2H), 4.19-4.33 (m, 1H), 3.87-3.92 (m, 3H), 3.04-3.18 (m, 2H), 2.79-2.96 (m, 1H), 2.49-2.65 (m, 1H). MS (ESI) m/z 513 (M+H)$^+$.

Example 9B methyl 3-{[trans-5-amino-4-(2,4-dichlorophenyl)-2-pyridin-3-ylcyclohex-1-en-1-yl]methoxy}benzoate To a solution of Example 9A (35 mg, 0.068 mmol) in mixture of methanol/acetic acid (0.5 mL/0.5 mL) Zn powder (45 mg, 0.68 mmol) was added at room temperature. The reaction mixture was stirred for thirty minutes, filtered, concentrated under reduced pressure and purified by high-pressure liquid chromatography (eluting with 0-70% acetonitrile/water and 0.1% trifluoroacetic acid) to provide the title compound (25 mg, 76%). $^1$H NMR (400 MHz, DMSO-d$_6$) δ ppm 8.54-8.72 (m, 1H), 7.89-8.11 (m, 2H), 6.96-7.72 (m, 8H), 4.46-4.58 (m, 2H), 3.80-3.87 (m, 4H), 3.59-3.72 (m, 1H), 2.53-2.88 (m, 4H). MS (ESI) m/z 483 (M+H)$^+$.

Example 10 trans-6-(2,4-dichlorophenyl)-4-pyridin-3-yl-3-[(pyridin-4-yloxy)methyl]cyclohex-3-en-1-amine

Example 10A

3-{trans-5-(2,4-dichlorophenyl)-4-nitro-2-[(pyridin-4-yloxy)methyl]cyclohex-1-en-1-yl}pyridine To a high pressure tube, Example 8A (52 mg, 0.137 mmol), 4-hydroxy-pyridine (17 mg, 0.172 mmol), triphenylphosphine (58 mg, 0.22 mmol) and di-t-butyl azodicarboxylate (51 mg, 0.22 mmol) were dissolved in toluene (1 mL). The stirred tube was sealed and heated to 85° C. overnight. The reaction mixture was cooled to room temperature, concentrated under reduced pressure and purified by flash chromatography (eluting with 30% ethyl acetate/hexane) to provide the title compound (30 mg, 48%). $^1$H NMR (400 MHz, CDCl$_3$) δ ppm 8.49-8.81 (m, 4H), 7.68-7.84 (m, 1H), 7.40-7.61 (m, 2H), 7.11-7.35 (m, 4H), 5.21-5.41 (m, 1H), 4.60-4.76 (m, 2H), 4.21-4.37 (m, 1H), 2.84-3.29 (m, 4H). MS (ESI) m/z 456 (M+H)$^+$.

Example 10B trans-6-(2,4-dichlorophenyl)-4-pyridin-3-yl-3-[(pyridin-4-yloxy)methyl]cyclohex-3-en-1-amine To a solution of Example 10A (25 mg, 0.055 mmol) in mixture of methanol/acetic acid (0.5 mL/0.5 mL), Zn powder (36 mg, 0.55 mmol) was added at room temperature. The reaction mixture was stirred for thirty minutes, filtered, concentrated under reduced pressure, and purified by high pressure liquid chromatography (eluting with 0-70% acetonitrile/water and 0.1% trifluoroacetic acid) to provide the title compound 9 (15 mg, 64%). $^1$H NMR (400 MHz, DMSO-d$_6$) δ ppm 8.46-8.81 (m, 3H), 7.35-8.25 (m, 8H), 4.64-4.83 (m, 2H), 3.57-3.75 (m, 2H), 2.50-2.97 (m, 4H). MS (ESI) m/z 426 (M+H)$^+$.

Example 11

1-{[trans-5-amino-4-(2,4-dichlorophenyl)cyclohex-1-en-1-yl]methyl}piperidine-4-carboxylic acid

Example 11A

[trans-4-(2,4-dichlorophenyl)-5-nitrocyclohex-1-en-1-yl]methanol

In a well stirred high pressure tube, Example 7C (380 mg, 1.06 mmol), formic acid (0.08 mL, 2.12 mmol), bis(triphenylphosphine)palladium(II) dichloride (38 mg, 0.053 mmol) and tributylamine (0.76 mL, 3.18 mmol) were dissolved in N,N-dimethylformamide (2 mL). The stirred tube was sealed and heated to 80° C. overnight. The reaction mixture was cooled to room temperature, filtered through Celite and then extracted with ethyl acetate. The combined ethyl acetate solution was washed with water and brine, dried over sodium sulfate, filtered, concentrated under reduced pressure and purified by flash chromatography (eluting with 30% ethyl acetate/hexane) to provide the title compound (210 mg, 80%). $^1$H NMR (300 MHz, CDCl$_3$) δ ppm 7.35-7.46 (m, 1H), 7.13-7.30 (m, 2H), 5.75-5.88 (m, 1H), 5.03-5.18 (m, 1H), 4.08-4.20 (m, 2H), 3.98-4.09 (m, 1H), 2.51-3.04 (m, 4H). MS (DCI) m/z 319 (M+NH$_3$)$^+$.

Example 11B ethyl 1-{[trans-4-(2,4-dichlorophenyl)-5-nitrocyclohex-1-en-1-yl]methyl}piperidine-4-carboxylate To a cold (0° C.) CH$_2$Cl$_2$ (1 mL) solution of Example 11A (61 mg, 0.2 mmol), methanesulfonyl chloride (0.017 mL, 0.22 mmol) and triethylamine (0.035 mL, 0.25 mmol) were added. After it was stirred at 0° C. for five minutes, more triethylamine (0.035 mL, 0.25 mmol) and ethyl isonipecotate (0.037 mL, 0.24 mmol) were added to the reaction mixture. The reaction was stirred from 0° C. to room temperature overnight, was diluted with CH$_2$Cl$_2$, washed with water and brine, dried over sodium sulfate, filtered, concentrated under reduced pressure and purified by high pressure liquid chromatography (eluting with 0-70% acetonitrile/water and 0.1% trifluoroacetic acid) to provide the title compound (65 mg, 73%). $^1$H NMR (300 MHz, CDCl$_3$) δ ppm 7.35-7.42 (m, 1H), 7.16-7.25 (m, 2H), 5.64-5.80 (m, 1H), 4.99-5.15 (m, 1H), 4.08-4.21 (m, 2H), 3.93-4.07 (m, 1H), 2.11-3.05 (m, 11H), 1.74-2.01 (m, 4H), 1.19-1.32 (m, 3H). MS (ESI) m/z 441 (M+H)$^+$.

Example 11C ethyl 1-{[trans-5-amino-4-(2,4-dichlorophenyl)cyclohex-1-en-1-yl]methyl}piperidine-4-carboxylate To a solution of Example 11B (60 mg, 0.136 mmol) in mixture of methanol/acetic acid (0.5 mL/0.5 mL), Zn powder (89 mg, 1.36 mmol) was added at room temperature. The reaction mixture was stirred for thirty minutes, filtered, concentrated under reduced pressure and purified by high pressure liquid chromotography (eluting with 0-70% acetonitrile/ water and 0.1% trifluoroacetic acid) to provide the title compound (50 mg, 89%). $^1$H NMR (400 MHz, DMSO-d$_6$) δ ppm 7.85-8.03 (m, 3H), 7.66 (s, 1H), 7.46-7.61 (m, 2H), 5.97-6.16 (m, 1H), 4.02-4.22 (m, 2H), 3.65-3.95 (m, 3H), 2.82-3.04 (m, 2H), 1.68-2.69 (m, 13H), 1.12-1.29 (m, 3H). MS (ESI) m/z 411 (M+H)$^+$.

Example 11D

1-{[trans-5-amino-4-(2,4-dichlorophenyl)cyclohex-1-en-1-yl]methyl}piperidine-4-carboxylic acid To a solution of Example 11C (36 mg, 0.088 mmol) in mixture of tetrahydrofuran/H$_2$O (0.3 mL/0.15 mL), LiOH (23 mg, 0.53 mmol) was added at room temperature. The reaction mixture was stirred overnight. It was acidified with 2N HCl in ether until pH=3 and purified by high pressure liquid chromotography (eluting with 0-70% acetonitrile/water and 0.1% trifluoroacetic acid) to provide the title compound (25 mg, 75%). $^1$H NMR (500 MHz, DMSO-d$_6$) δ ppm 7.90-8.07 (m, 3H), 7.67 (s, 1H), 7.47-7.58 (m, 2H), 6.01-6.14 (m, 1H), 3.66-3.96 (m, 2H), 2.57-3.04 (m, 4H), 1.65-2.46 (m, 9H). MS (ESI) m/z 383 (M+H)$^+$.

Example 12

N-{[trans-5-amino-4-(2,4-dichlorophenyl)cyclohex-1-en-1-yl]methyl}-3-chloro-4-(methylsulfonyl)thiophene-2-carboxamide Example 12A

[trans-4-(2,4-dichlorophenyl)-5-nitrocyclohex-1-en-1-yl]methyl methanesulfonate

To a cold (0° C.) CH$_2$Cl$_2$ (20 mL) solution of Example 11A (1.56 g, 5.17 mmol), methanesulfonyl chloride (0.49 mL, 6.2 mmol) and triethylamine (1.8 mL, 12.91 mmol) were added. The reaction mixture was stirred from 0° C. to room temperature overnight. It was diluted with CH$_2$Cl$_2$, washed with water and brine, dried over sodium sulfate, filtered, and concentrated under reduced pressure to provide the crude title compound. MS (DSI) m/z 397 (M+NH$_4$)$^+$.

Example 12B

1-[trans-4-(azidomethyl)-6-nitrocyclohex-3-en-1-yl]-2,4-dichlorobenzene

To a solution of crude Example 12A (5.17 mmol) in N,N-dimethylformamide (20 mL) NaN$_3$ (3.36 g, 51.7 mmol) was added. The reaction mixture was stirred at room temperature overnight. It was diluted with ethyl acetate, washed with water and brine, dried over sodium sulfate, filtered, concentrated under reduced pressure, and purified by flash chromatography (eluting with 30% ethyl acetate/hexane) to provide the title compound (1.04 g, 62% for two steps). $^1$H NMR (500 MHz, CDCl$_3$) δ ppm 7.40 (s, 1H), 7.16-7.29 (m, 2H), 5.86 (m, 1H), 5.05-5.17 (m, 1H), 3.99-4.11 (m, 1H), 3.71-3.89 (m, 2H), 2.57-2.90 (m, 4H). MS (DCI) m/z 344 (M+NH$_4$)$^+$.

Example 12C

[trans-4-(2,4-dichlorophenyl)-5-nitrocyclohex-1-en-1-yl]methyl amine

To a solution of Example 12B (700 mg, 2.14 mmol) in mixture of tetrahydrofuran/H$_2$O (15 mL/1.5 mL), triphenylphosphine (1.12 mg, 4.28 mmol) was added at room temperature. The reaction mixture was heated to 65° C. for five hours. It was cooled to room temperature, concentrated under reduced pressure, azeotroped with toluene, and purified by flash chromatography (eluting with 10% methanol/ CH$_2$Cl$_2$) to provide the title compound. $^1$H NMR (500 MHz, methanol-d$_4$) δ ppm 7.41-7.48 (m, 2H), 7.28-7.35 (m, 1H), 5.72 (m, 1H), 5.26-5.38 (m, 1H), 3.93-4.04 (m, 1H), 3.17-3.42 (m, 4H), 2.72-2.84 (m, 2H). MS (DCI) m/z 301 (M+H)$^+$.

Example 12D 3-chloro-N-{[trans-4-(2,4-dichlorophenyl)-5-nitrocyclohex-1-en-1-yl]methyl}-4-(methylsulfonyl)thiophene-2-carboxamide To a solution of Example 12C (33 mg, 0.11 mmol) in CH$_2$Cl$_2$ (1 mL), 3-chloro-4-methanesulfonyl-thiophene-2-carbonyl chloride (43 mg, 0.16 mmol) and diisopropylethyl amine (0.05 mL, 0.33 mmol) were added. The reaction mixture was stirred at room temperature overnight. It was concentrated under reduced pressure and purified by high pressure liquid chromotography (eluting with 0-70% acetonitrile/ water and 0.1% trifluoroacetic acid) to provide the title compound (48 mg, 84%). $^1$H NMR (300 MHz, CDCl$_3$) δ ppm 8.39 (s, 1H), 8.19 (s, 1H), 7.40 (s, 1H), 7.17-7.25 (m, 2H), 5.82 (m, 1H), 5.04-5.17 (m, 1H), 3.98-4.19 (m, 3H), 3.18-3.21 (m, 3H), 2.51-2.95 (m, 3H), 2.16-2.35 (m, 1H). MS (ESI) m/z 523 (M+H)$^+$.

Example 12E

N-{[trans-5-amino-4-(2,4-dichlorophenyl)cyclohex-1-en-1-yl]methyl}-3-chloro-4-(methylsulfonyl)thiophene-2-carboxamide To a solution of Example 12D (40 mg, 0.077 mmol) in mixture of methanol/acetic acid (0.5 mL/0.5 mL), Zn powder (50 mg, 0.77 mmol) was added at room temperature. The reaction mixture was stirred for thirty minutes, filtered, concentrated under reduced pressure, and purified by high pressure liquid chromotography (eluting with 0-70% acetonitrile/ water and 0.1% trifluoroacetic acid) to provide the title compound (25 mg, 66%). $^1$H NMR (400 MHz, methanol-d$_4$) δ ppm 8.45 (s, 1H), 8.03 (s, 1H), 7.54 (s, 1H), 7.35-7.47 (m, 2H), 5.82 (m, 1H), 3.82-4.06 (m, 3H), 3.49-3.61 (m, 1H), 3.18 (s, 3H), 2.43-2.62 (m, 2H), 2.24-2.42 (m, 2H). MS (ESI) m/z 493 (M+H)$^+$.

Example 13

N-{[trans-5-amino-4-(2,4-dichlorophenyl)cyclohex-1-en-1-yl]methyl}-5-bromonicotinamide

Example 13A 5-bromo-N-{[trans-4-(2,4-dichlorophenyl)-5-nitro-cyclohex-1-en-1-yl]methyl}nicotinamide To a solution of Example 12C (33 mg, 0.11 mmol) in CH$_2$Cl$_2$ (1 mL), 5-bromo-nictinoyl chloride (37 mg, 0.16 mmol) and diisopropylethyl amine (0.05 mL, 0.33 mmol) were added. The reaction mixture was stirred at room temperature overnight. It was concentrated under reduced pressure and purified by high pressure liquid chromatography (eluting with 0-70% acetonitrile/water and 0.1% trifluoroacetic acid) to provide the title compound (38 mg, 71%). $^1$H NMR (300 MHz, CDCl$_3$) δ ppm 9.13 (s, 1H), 8.85 (s, 1H), 8.54 (s, 1H), 8.45 (s, 1H), 7.40 (s, 1H), 7.16-7.25 (m, 2H), 5.82 (m, 1H), 5.03-5.18 (m, 1H), 4.00-4.21 (m, 3H), 2.51-2.98 (m, 4H). MS (ESI) m/z 486 (M+H)$^+$.

Example 13B

N-{[trans-5-amino-4-(2,4-dichlorophenyl)cyclohex-1-en-1-yl]methyl}-5-bromonicotinamide To a solution of Example 12D (35 mg, 0.072 mmol) in mixture of methanol/acetic acid (0.5 mL/0.5 mL), Zn powder (47 mg, 0.72 mmol) was added at room temperature. The reaction mixture was stirred for thirty minutes, filtered, concentrated under reduced pressure, and purified by high pressure liquid chromatography (eluting with 0-70% acetonitrile/water and 0.1% trifluoroacetic acid) to provide the title compound (30 mg, 91%). $^1$H NMR (400 MHz, MEOH-D4) δ ppm 8.96 (s, 1H), 8.83 (s, 1H), 8.42 (s, 1H), 7.54 (s, 1H), 7.36-7.50 (m, 2H), 5.83 (m, 1H), 3.97-4.01 (m, 2H), 3.82-3.95 (m, 1H), 3.48-3.64 (m, 1H), 2.45-2.62 (m, 2H), 2.25-2.41 (m, 2H). MS (ESI) m/z 456 (M+H)$^+$.

Example 14

3-{[trans-5-amino-4-(2,4-dichlorophenyl)-2-pyridin-3-ylcyclohex-1-en-1-yl]methoxy}benzoic acid To a solution of Example 9B (18 mg, 0.037 mmol) in mixture of tetrahydrofuran/H$_2$O (0.5 mL/0.25 mL), LiOH (9.4 mg, 0.22 mmol) was added at room temperature. The reaction mixture was stirred overnight. It was acidified with 2N HCl in ether until the pH=3 and purified by reverse-phase high pressure liquid chromatography (eluting with 0-70% acetonitrile/water and 0.1% trifluoroacetic acid) to provide the title compound (14 mg, 80%). $^1$H NMR (500 MHz, methanol-d$_4$) δ ppm 8.65-8.76 (m, 2H), 8.25-8.33 (m, 1H), 7.81-7.91 (m, 1H), 7.48-7.65 (m, 3H), 7.30-7.44 (m, 3H), 7.01-7.10 (m, 1H), 4.48-4.59 (m, 2H), 4.00-4.12 (m, 1H), 3.74-3.87 (m, 1H), 2.60-3.02 (m, 4H). MS (ESI) m/z 469 (M+H)$^+$.

Example 15

4-[({[trans-5-amino-4-(2,4-dichlorophenyl)cyclohex-1-en-1-yl]methyl}amino)carbonyl]benzoic acid

Example 15A methyl 4-[({[trans-4-(2,4-dichlorophenyl)-5-nitrocyclohex-1-en-1-yl]methyl}amino)carbonyl]benzoate To a solution of Example 12C (33 mg, 0.11 mmol) in CH$_2$Cl$_2$ (1 mL), 4-chlorocarbonyl-benzoic acid methyl ester (33 mg, 0.16 mmol) and diisopropylethyl amine (0.05 mL, 0.33 mmol) were added. The reaction mixture was stirred at room temperature overnight. It was concentrated under reduced pressure and purified by high pressure liquid chromatography (eluting with 0-70% acetonitrile/water and 0.1% trifluoroacetic acid) to provide the title compound (41 mg, 81%). $^1$H NMR (500 MHz, CDCL3) δ ppm 8.06-8.10 (m, 2H), 7.86-7.92 (m, 2H), 7.37-7.41 (m, 1H), 7.15-7.26 (m, 2H), 5.73-5.82 (m, 1H), 5.02-5.13 (m, 1H), 4.01-4.13 (m, 3H), 2.50-2.95 (m, 3H). MS (ESI) m/z 463 (M+H)$^+$.

Example 15B

4-[({[trans-5-amino-4-(2,4-dichlorophenyl)cyclohex-1-en-1-yl]methyl}amino)carbonyl]benzoic acid To a solution of Example 15A (35 mg, 0.076 mmol) in mixture of methanol/acetic acid (0.5 mL/0.5 mL), Zn powder (49 mg, 0.76 mmol) was added at room temperature. The reaction mixture was stirred for 30 minutes, filtered, concentrated under reduced pressure and purified by high pressure liquid chromatography (eluting with 0-70% acetonitrile/water and 0.1% trifluoroacetic acid) to provide the title compound (10 mg, 32%). $^1$H NMR (300 MHz, methanol-d$_4$) δ ppm 8.06-8.16 (m, 2H), 7.88-7.97 (m, 2H), 7.52-7.59 (m, 1H), 7.37-7.49 (m, 2H), 7.10-7.24 (m, 1H), 5.78-5.87 (m, 1H), 3.97-4.06 (m, 2H), 3.83-3.95 (m, 1H), 3.49-3.62 (m, 1H), 2.25-2.61 (m, 4H). MS (ESI) m/z 419 (M+H)$^+$.

Example 16

1-{[trans-5-amino-4-(2,4-dichlorophenyl)cyclohex-1-en-1-yl]methyl}piperidin-4-ol

Example 16A

1-{[trans-4-(2,4-dichlorophenyl)-5-nitrocyclohex-1-en-1-yl]methyl}piperidin-4-ol To a cold (0° C.) CH$_2$Cl$_2$ (1 mL) solution of Example 1A (61 mg, 0.2 mmol), methanesulfonyl chloride (0.017 mL, 0.22 mmol) and triethylamine (0.035 mL, 0.25 mmol) were added. After it was stirred at 0° C. for five minutes, more triethylamine (0.035 mL, 0.25 mmol) and piperidin-4-ol (25 mg, 0.24 mmol) were added to the reaction mixture. The reaction was allowed to warm from 0° C. to room temperature overnight. It was diluted with CH$_2$Cl$_2$, washed with water and brine, dried over sodium sulfate, filtered, concentrated under reduced pressure and purified by high pressure liquid chromatography (eluting with 0-70% acetonitrile/water and 0.1% trifluoroacetic acid) to provide the title compound (54 mg, 69%). MS (DCI) m/z 386 (M+H)$^+$.

Example 16B

1-{[trans-5-amino-4-(2,4-dichlorophenyl)cyclohex-1-en-1-yl]methyl}piperidin-4-ol To a solution of Example 16A (50 mg, 0.13 mmol) in mixture of methanol/acetic acid (0.5 mL/0.5 mL), Zn powder (85 mg, 1.3 mmol) was added at room temperature. The reaction mixture was stirred for thirty minutes, filtered, concentrated under reduced pressure and purified by high pressure liquid chromatography (eluting with 0-70% acetonitrile/water and 0.1% trifluoroacetic acid) to provide the title compound (35 mg, 76%). $^1$H NMR (300 MHz, methanol-$d_4$) δ ppm 7.54-7.61 (m, 1H), 7.39-7.49 (m, 2H), 6.14-6.34 (m, 1H), 3.89-4.02 (m, 1H), 3.73-3.84 (m, 1H), 3.51-3.69 (m, 1H), 2.36-3.13 (m, 3H), 1.91-2.19 (m, 1H). MS (ESI) m/z 356 (M+H)$^+$.

Example 17

(3S)-1-{[trans-5-amino-4-(2,4-dichlorophenyl)cyclohex-1-en-1-yl]methyl}piperidine-3-carboxylic acid

Example 17A ethyl(3S)-1-{[trans-4-(2,4-dichlorophenyl)-5-nitrocyclohex-1-en-1-yl]methyl}piperidine-3-carboxylate To a cold (0° C.) $CH_2Cl_2$ (1 mL) solution of Example 11A (141 mg, 0.47 mmol), methanesulfonyl chloride (0.041 mL, 0.57 mmol) and triethylamine (0.173 mL, 1.23 mmol) were added. After it was stirred at 0° C. for five minutes, more triethylamine (0.080 mL, 0.571 mmol) and (S)-(+)-ethyl nipecotate (94 mg, 1.2 mmol) were added to the reaction mixture. It was stirred from 0° C. to room temperature overnight. It was diluted with $CH_2Cl_2$, washed with water and brine, dried over sodium sulfate, filtered, concentrated under reduced pressure, and purified by high pressure liquid chromatography (eluting with 0-70% acetonitrile/water and 0.1% trifluoroacetic acid) to provide the title compound (115 mg, 55%). $^1$H NMR (400 MHz, $CDCl_3$) δ ppm 7.40 (d, 1H), 7.23-7.20 (m, 2H), 5.75-5.65 (m, 1H), 5.15-5.00 (m, 1H), 4.20-4.10 (m, 2H), 4.08-3.95 (m, 1H), 3.01-2.83 (m, 2H), 2.77-2.63 (m, 2H), 2.63-2.50 (m, 4H), 2.30-2.10 (m, 3H), 2.10-1.95 (m, 1H), 1.95-1.85 (m, 1H), 1.80-1.70 (m, 1H), 1.23 (t, 3H). MS (DCI) m/z 441 (M+H)$^+$.

Example 17B ethyl(3S)-1-{[trans-5-amino-4-(2,4-dichlorophenyl)cyclohex-1-en-1-yl]methyl}piperidine-3-carboxylate To a solution of Example 17A (75 mg, 0.16 mmol) in a mixture of methanol/acetic acid (1.0 mL/1.0 mL), Zn powder (170 mg, 2.60 mmol) was added at room temperature. The reaction mixture was stirred for thirty minutes, filtered, concentrated under reduced pressure and purified by high pressure liquid chromatography (eluting with 0-70% acetonitrile/water and 0.1% trifluoroacetic acid) to provide the title compound (60 mg, 86%). MS (DCI) m/z 411 (M+H)$^+$.

Example 17C (3S)-1-{[trans-5-amino-4-(2,4-dichlorophenyl)cyclohex-1-en-1-yl]methyl}piperidine-3-carboxylic acid To a solution of Example 17B (55 mg, 0.13 mmol) in a mixture of tetrahydrofuran/$H_2O$ (1.0 mL/0.5 mL), LiOH (19 mg, 0.80 mmol) was added at room temperature. The reaction mixture was stirred overnight. It was acidified with 2N HCl in ether until pH=3 and purified by high pressure liquid chromatography (eluting with 0-70% acetonitrile/water and 0.1% trifluoroacetic acid) to provide the title compound (32 mg, 63%). $^1$H NMR (400 MHz, methanol-$d_4$) δ ppm 7.78 (s, 1H), 7.55-7.52 (m, 1H), 7.42-7.38 (m, 1H), 6.21 (s, 1H), 4.0-3.90 (m, 1H) 3.85-3.70 (m, 2H), 3.65-3.50 (m, 1H), 3.20-2.8 (m, 3H), 2.75-2.55 (m, 3H), 2.50-2.40 (m, 3H), 2.35-2.20 (m, 2H), 2.05-1.85 (m, 2H). MS (APCI) m/z 383 (M+H)$^+$.

Example 18

(3R)-1-{[trans-5-amino-4-(2,4-dichlorophenyl)cyclohex-1-en-1-yl]methyl}piperidine-3-carboxylic acid

Example 18A ethyl(3R)-1-{[trans-4-(2,4-dichlorophenyl)-5-nitrocyclohex-1-en-1-yl]methyl}piperidine-3-carboxylate To a cold (0° C.) $CH_2Cl_2$ (3 μL) solution of Example 11A (150 mg, 0.50 mmol), methanesulfonyl chloride (0.043 mL, 0.58 mmol) and triethylamine (0.173 mL, 1.23 mmol) were added. After it was stirred at 0° C. for five minutes, more triethylamine (0.080 mL, 0.571 mmol) and (R)-(+)-ethyl nipecotate (94 mg, 1.2 mmol) were added to the reaction mixture. It was stirred and allowed to warm from 0° C. to room temperature overnight. It was diluted with $CH_2Cl_2$, washed with water and brine, dried over sodium sulfate, filtered, concentrated under reduced pressure and purified by high pressure liquid chromatography (eluting with 0-70% acetonitrile/water and 0.1% trifluoroacetic acid) to provide the title compound (125 mg, 57%). $^1$H NMR (400 MHz, $CDCl_3$) δ ppm 7.39 (d, 1H), 7.23-7.21 (m, 2H), 5.70-5.60 (m, 1H), 5.15-5.00 (m, 1H), 4.20-4.11 (m, 2H), 4.05-3.95 (m, 1H), 3.00-2.80 (m, 2H), 2.75-2.65 (m, 2H), 2.65-2.50 (m, 4H), 2.30-2.15 (m, 3H), 2.10-1.95 (m, 1H), 1.95-1.85 (m, 1H), 1.80-1.70 (m, 1H), 1.27 (t, 3H). MS (DCI) m/z 441 (M+H)$^+$.

Example 18B ethyl(3R)-1-{[trans-5-amino-4-(2,4-dichlorophenyl)cyclohex-1-en-1-yl]methyl}piperidine-3-carboxylate To a solution of Example 18A (100 mg, 0.24 mmol) in a mixture of methanol/acetic acid (1.0 mL/1.0 mL), Zn powder (170 mg, 2.6 mmol) was added at room temperature. The reaction mixture was stirred for 30 minutes, filtered, concentrated under reduced pressure and purified by high pressure liquid chromatography (eluting with 0-70% acetonitrile/water and 0.1% trifluoroacetic acid) to provide the title compound (78 mg, 78%). $^1$H NMR (400 MHz, methanol-$d_4$) δ ppm 7.62 (br s, 1H), 7.51 (br s, 1H), 7.39 (br s, 1H), 6.30-6.20 (m, 1H), 4.21 (q, 2H), 3.95-3.85 (m, 1H), 3.8-3.5 (m, 4H), 3.15-2.80 (m, 4H), 2.75-2.40 (m, 3H), 2.35-2.20 (m, 2H), 2.10-1.90 (m, 2H), 1.65-1.50 (m, 1H), 1.30 (t, 3H). MS (DCI) m/z 411 (M+H)$^+$.

Example 18C (3R)-1-{[trans-5-amino-4-(2,4-dichlorophenyl)cyclohex-1-en-1-yl]methyl}piperidine-3-carboxylic acid To a solution of Example 18B (71 mg, 0.13 mmol) in mixture of tetrahydrofuran/$H_2O$ (1.0 mL/0.5 mL), LiOH (25 mg, 1.03 mmol) was added at room temperature. The reaction mixture was stirred overnight. It was acidified with 2N HCl in ether until pH=3 and purified by high pressure liquid chromotography (eluting with 0-70% acetonitrile/water and 0.1% trifluoroacetic acid) to provide the title compound (35 mg, 53%). $^1$H NMR (400 MHz, methanol-$d_4$) δ ppm 7.78 (s, 1H), 7.55-7.52 (m, 1H), 7.42-7.38 (m, 1H), 6.20 (s, 1H), 4.05-3.85 (m, 1H) 3.82-3.70 (m, 2H), 3.63-3.48 (m, 1H), 3.20-2.8 (m, 3H), 2.75-2.55 (m, 3H), 2.50-2.40 (m, 3H), 2.35-2.20 (m, 2H), 2.07-1.89 (m, 2H). MS (APCI) m/z 383 (M+H)$^+$.

Example 19 trans-3-{[3-(trifluoromethyl)-5,6-dihydro[1,2,4]triazolo[4,3-a]pyrazin-7(8H)-yl]methyl}-6-(2,4,5-trifluorophenyl)cyclohex-3-en-1-amine

Example 19A trans-4-nitro-3-(2,4,5-trifluorophenyl)cyclohexanone 2,4,5-Trifluoro-β-nitrostyrene (7.8 g, 38.4 mmol) and 2-trimethylsiloxy-1,3-butadiene (8.18 g, 57.6 mmol) were mixed in toluene (10 ml). The reaction was heated to 120° C. overnight. The reaction mixture was cooled to room temperature, concentrated and treated with trifluoroacetic acid (10 mL) and $CH_2Cl_2$ (10 mL) at 0° C. It was stirred for 30 minutes, then saturated $NaHCO_3$ was added to adjust pH (~7). The mixture was extracted with ethyl acetate (3×) and the combined organic extracts were washed with water and brine, and then concentrated. A minimum amount of methylene chloride was added to the residue to induce crystallization. The crystals were collected by filtration and the mother liquid was subjected to column chromatography (eluting with 25% ethyl acetate/hexane). The recrystallized and chromatographed material was combined to yield the title compound (7.0, 70%). $^1$H NMR (300 MHz, $CDCl_3$) δ ppm 2.29-2.82 (m, 6H), 3.73-3.89 (m, 1H), 5.06-5.29 (m, 1H), 6.86-7.12 (m, 2H). MS (ESI) m/z 274 (M+H)$^+$.

Example 19B trans-2-bromo-5-nitro-4-(2,4,5-trifluorophenyl)cyclohex-1-ene-1-carbaldehyde $PBr_3$ (4.56 mL, 48 mmol) was added to a cold solution (0° C.) of N,N-dimethylformamide (4.5 ml, 58.2 mmol) in $CH_2Cl_2$ (45 ml). The mixture was stirred at 0° C. for one hour and then Example 19A (5.3 g, 19.4 mmol) was added. The reaction was stirred at room temperature overnight. The mixture was cooled to 0° C. and saturated $NaHCO_3$ was added. It was then extracted by $CH_2Cl_2$ (3×) and washed with brine. The organic layer was combined, concentrated and subjected to column chromatography (eluting with 20% ethyl acetate/hexane) to yield the title compound: 2.9 g (41%). $^1$H NMR (300 MHz, $CDCl_3$) δ ppm 2.93-3.35 (m, 4H), 3.68-4.00 (m, J=6.10 Hz, 1H), 4.85-5.23 (m, 1H), 6.83-7.14 (m, 2H), 10.02 (s, 1H). MS (ESI) m/z 364, 366 (M+H)$^+$.

Example 19C

[trans-2-bromo-5-nitro-4-(2,4,5-trifluorophenyl)cyclohex-1-en-1-yl]methanol

To Example 19B (2 g, 5.5 mmol) in $CH_2Cl_2$ (12 mL), sodium triacetoxyborohydride (3.5 g, 16.5 mmol) was added. After stirring overnight, the reaction mixture was diluted with ethyl acetate (50 mL) and saturated $NaHCO_3$ was added. The mixture was extracted with ethyl acetate (3×). The combined organic extracts were dried over $Na_2SO_4$, concentrated and purified by flash chromatography (eluting with 25% ethyl acetate in hexane) to yield the title compound (1.56 g, 78%). $^1$H NMR (300 MHz, $CDCl_3$) δ ppm 2.68-3.14 (m, 4H), 3.62-3.91 (m, 1H), 4.36 (s, 2H), 4.97-5.21 (m, 1H), 6.84-7.10 (m, 2H). MS (ESI) m/z 366, 368 (M+H)$^+$.

Example 19D

[trans-5-nitro-4-(2,4,5-trifluorophenyl)cyclohex-1-en-1-yl]methanol

Example 19C (2.3 g, 6.4 mmol) was dissolved in N,N-dimethylformamide (5 mL). Tributyl amine (4.6 mL, 19.3 mmol) was added followed by HCOOH (0.6 mL, 12.8 mmol). Bis(triphenylphosphine)palladium(II) dichloride (23 mg, 0.03 mmol) was added and the reaction was heated to 80° C. for overnight. The mixture was cooled to room temperature, filtered, concentrated, and subjected to column chromatography (eluting with 50% ethyl acetate/hexane) to obtain the title compound (1 g, 60%). $^1$H NMR (300 MHz, $CDCl_3$) δ ppm 2.24-2.62 (m, 2H), 2.71-2.84 (m, 3H), 3.41-3.73 (m, 1H), 4.96-5.21 (m, 1H), 5.80 (d, J=2.37 Hz, 1H), 5.81 (s, 1H), 6.82-7.12 (m, 2H). MS (ESI) m/z 288 (M+H)$^+$.

Example 19E

[trans-5-nitro-4-(2,4,5-trifluorophenyl)cyclohex-1-en-1-yl]methyl methanesulfonate Example 19D (270 mg, 0.94 mmol) and triethyl amine (0.33 mL, 2.35 mmol) were mixed in $CH_2Cl_2$ (2 mL). The mixture was cooled to 0° C. and methanesulfonyl chloride (0.087 mL, 1.18 mmol) was added. It was allowed to warm to room temperature and stirred for one hour. The mixture was concentrated and subjected to column chromatography (eluting with 40% ethyl acetate/hexane) to obtain the title compound (280 mg, 82%). $^1$H NMR (300 MHz, $CDCl_3$) δ ppm 2.41-2.65 (m, 2H), 2.75-2.92 (m, 2H), 3.06 (s, 3H), 3.50-3.71 (m, 1H), 4.68 (s, 2H), 4.95-5.13 (m, 1H), 6.01 (s, 1H), 6.83-7.12 (m, 2H). MS (ESI) m/z 366 (M+H)$^+$.

Example 19F trans-3-{[3-(trifluoromethyl)-5,6-dihydro[1,2,4]triazolo[4,3-a]pyrazin-7(8H)-yl]methyl}-6-(2,4,5-trifluorophenyl)cyclohex-3-en-1-amine Step A Example 19E (66 mg, 0.18 mmol), 3-trifluoromethyl-5,6,7,8-tetrahydro-[1,2,4]triazolo[4,3-a]pyrazine (prepared as described in D. Kim et al, J. Med. Chem. 2005, 48, 141-151). 41.6 mg, 0.216 mmol), and triethyl amine (62.6 mL, 0.45

μmol) were mixed in 1 mL of methylene chloride and stirred for two days. The mixture was then purified by flash chromatography (eluting with 60-70% ethyl acetate/hexane) to give the desired nitro amine.

Step B

The intermediate from step A (18.4 mg), zinc dust (60 mg) was mixed in 0.8 mL each of acetic acid and methanol and then heated to 75° C. for two hours. The mixture was cooled to room temperature, and filtered through Celite. The filtrate was concentrated and then purified by reverse-phase high pressure liquid chromatography (eluting with 0-70% acetonitrile/water and 0.1% trifluoroacetic acid) to give the title compound. $^1$H NMR (400 MHz, methanol-$d_4$) δ ppm 2.23-2.36 (m, 1H), 2.46-2.55 (m, J=4.60 Hz, 2H), 2.68 (dd, J=17.34, 4.76 Hz, 1H), 3.03 (t, J=5.52 Hz, 2H), 3.24-3.29 (m, 3H), 3.76-3.86 (m, 1H), 3.89 (s, 2H), 4.24 (t, J=5.37 Hz, 2H), 5.90 (s, 1H), 7.19-7.29 (m, 1H), 7.35-7.46 (m, 1H). MS (ESI) m/z 432 (M+H)$^+$.

Example 20 trans-3-[(4-acetylpiperazin-1-yl)methyl]-6-(2,4,5-trifluorophenyl)cyclohex-3-en-1-amine Example 20A tert-butyl trans-4-bromo-3-(hydroxymethyl)-6-(2,4,5-trifluorophenyl)cyclohex-3-en-1-ylcarbamate Example 19C (2.5 g, 6.87 mmol) was dissolved in methanol (5 mL). Acetic acid (5 mL) and zinc (3.57 g, 8 eq.) were added. The reaction mixture was heated to 80° C. for two hours, cooled to room temperature, and filtered. The filtrate was washed with ammonium hydroxide. The mixture was extracted with ethyl acetate (3×). The combined organic extracts were dried over Na$_2$SO$_4$, and concentrated. The concentrate was dissolved in tetrahydrofuran (10 mL), and di-tert-butyl dicarbonate (1.43 g, 1.1 eq.) was added. After thirty minutes, the reaction mixture was concentrated and subjected to column chromatography (eluting with 20% ethyl acetate/hexane) to give the title compound (2.54 g, 85% for 2 steps). $^1$H NMR (500 MHz, CDCl$_3$) δ ppm 1.23-1.46 (s, 9H), 2.15-2.32 (m, 1H), 2.61-2.91 (m, 3H), 3.30 (d, J=5.80 Hz, 1H), 4.07 (s, 1H), 4.20-4.44 (m, 3H), 6.81-6.97 (m, 1H), 7.11 (s, 1H). MS (ESI) m/z 436, 438 (M+H)$^+$.

Example 20B tert-butyl trans-3-(hydroxymethyl)-6-(2,4,5-trifluorophenyl)cyclohex-3-en-1-ylcarbamate Example 20A (2.8 g, 6.4 mmol) was dissolved in N,N-dimethylformamide (5 mL). Tributyl amine (4.6 mL, 19.3 mmol) was added followed by HCOOH (0.6 mL, 12.8 mmol). Bis(triphenylphosphine)palladium(II) dichloride (23 mg, 0.03 mmol) was added and the reaction was heated to 80° C. for overnight. The mixture was cooled to room temperature, filtered, concentrated and subjected to column chromatography (eluting with 25% ethyl acetate/hexane) to give the title compound (1.6 g, 70%). $^1$H NMR (300 MHz, CDCl$_3$) δ ppm 1.21-1.43 (s, 9H), 1.91-2.21 (m, 2H), 2.24-2.56 (m, 3H), 2.94-3.19 (m, 1H), 3.97-4.04 (m, 2H), 5.74 (s, 1H), 6.76-6.99 (m, 1H), 7.04-7.22 (m, J=1.00 Hz, 1H). MS (ESI) m/z 358 (M+H)$^+$.

Example 20C tert-butyl trans-3-formyl-6-(2,4,5-trifluorophenyl)cyclohex-3-en-1-ylcarbamate Example 20B (2 g, 5.6 mmol) and Dess-Martin periodinane (3.3 g, 8.4 mmol) were mixed in CH$_2$Cl$_2$ (10 mL). It was stirred for two hours. The mixture was filtered, concentrated, and subjected to column chromatography (eluting with 20% ethyl acetate/hexane) to obtain the title compound (1.6 g, 81%). $^1$H NMR (500 MHz, DMSO-$d_6$) δ ppm 1.14-1.28 (m, 9H), 2.05-2.15 (m, 1H), 2.57-2.73 (m, 2H), 3.02-3.12 (m, J=7.02 Hz, 1H), 3.22 (d, J=7.02 Hz, 1H), 3.76-3.93 (m, J=5.49 Hz, 1H), 6.84 (d, J=9.46 Hz, 1H), 6.98 (s, 1H), 7.27-7.64 (m, 2H), 9.48 (s, 1H). MS (ESI) m/z 356 (M+H)$^+$.

Example 20D trans-3-[(4-acetylpiperazin-1-yl)methyl]-6-(2,4,5-trifluorophenyl)cyclohex-3-en-1-amine Step A Example 20C (50 mg, 0.14 mmol) and N-acylpiperizine (0.17 mmol) were mixed in 1 mL each of methanol and methanol buffer (pH=4, sodium acetate:acetic acid, 1:1). The mixture was stirred for 0.5 hours and NaCNBH$_3$ (25 mg, 0.19 mmol) was added. The mixture was stirred for two hours, filtered, and purified by reverse phase high pressure liquid chromatography (eluting with 0% to 70% acetonitrile/0.1% aqueous trifluoroacetic acid).

Step B

The intermediate from step A (50 mg) was treated with trifluoroacetic acid/CH$_2$Cl$_2$ (1 mL:1 mL) and stirred for one hour. The product was purified by reverse phase high pressure liquid chromatography (eluting with 0% to 70% acetonitrile/ 0.1% aqueous trifluoroacetic acid). $^1$H NMR (500 MHz, methanol-$d_4$) δ ppm 2.16 (s, 3H), 2.34-2.52 (m, 1H), 2.51-2.64 (m, 2H), 2.72 (dd, J=16.78, 5.19 Hz, 1H), 3.28-3.43 (m, 6H), 3.72-3.94 (m, 5H), 6.17 (s, 1H), 7.20-7.31 (m, 1H), 7.34-7.46 (m, 1H). MS (ESI) m/z 368 (M+H)$^+$.

Example 21 trans-3-(3,4-dihydroisoquinolin-2(1H)-ylmethyl)-6-(2,4,5-trifluorophenyl)cyclohex-3-en-1-amine The title compound was synthesized using the procedure as described in Example 19F by substituting 1,2,3,4-tetrahydroisoquinoline for 3-trifluoromethyl-5,6,7,8-tetrahydro-[1,2,4]triazolo[4,3-a]pyrazine. $^1$H NMR (400 MHz, methanol-$d_4$) δ ppm 2.44-2.55 (m, 1H), 2.61 (br s, 2H), 2.75 (dd, J=16.88, 4.91 Hz, 1H), 3.24 (br s, 2H), 3.32-3.40 (m, 1H), 3.6 (very br s, 2H), 3.86-3.92 (m, 1H), 3.95 (s, 2H), 4.44 (br s, 2H), 6.22 (s, 1H), 7.20-7.36 (m, 5H), 7.38-7.46 (m, 1H). MS (ESI) m/z 373 (M+H)$^+$.

Example 22

N-{[trans-5-amino-4-(2,4,5-trifluorophenyl)cyclohex-1-en-1-yl]methyl}-N-phenylamine The title compound was synthesized using the procedure as described in Example 20D by substituting aniline for N-acylpiperizine. $^1$H NMR (400 MHz, methanol-$d_4$) δ ppm 2.21-2.35 (m, 1H), 2.39-2.50 (m, 2H), 2.54-2.63 (m, 1H), 3.18-3.28 (m, 1H), 3.68-3.83 (m, 3H), 5.87 (s, 1H), 6.70-6.82 (m, J=8.13, 8.13 Hz, 3H), 7.11-7.27 (m, 3H), 7.30-7.43 (m, 1H). MS (ESI) m/z 333 (M+H)$^+$.

Example 23

4-({[trans-5-amino-4-(2,4,5-trifluorophenyl)cyclohex-1-en-1-yl]methyl}amino)benzamide The title compound was synthesized using the procedure as described in Example 20D by substituting 4-aminobenzamide for N-acylpiperizine. $^1$H NMR (400 MHz, methanol-$d_4$) δ ppm 2.28 (s, 1H), 2.46 (s, 2H), 2.52-2.62 (m, 1H), 3.17-3.28 (m, 1H), 3.72-3.86 (m, 3H), 4.81 (none, 12H), 5.84 (s, 1H), 6.63 (d, J=8.59 Hz, 2H), 7.16-7.27 (m, 1H), 7.32-7.44 (m, 1H), 7.68 (d, J=8.59 Hz, 1H). MS (ESI) m/z 375 (M+H)$^+$.

Example 24

N-{[trans-5-amino-4-(2,4,5-trifluorophenyl)cyclohex-1-en-1-yl]methyl}-N-benzylamine The title compound was synthesized using the procedure as described in Example 20D, by substituting benzylamine for N-acylpiperizine. $^1$H NMR (300 MHz, methanol-$d_4$) δ ppm 2.30-2.72 (m, 4H), 3.19-3.26 (m, 1H), 3.70 (s, 2H), 3.75-3.89 (m, 1H), 4.24 (s, 2H), 6.06 (d, J=1.70 Hz, 1H), 7.17-7.32 (m, 1H), 7.33-7.45 (m, 1H), 7.45-7.57 (m, 5H). MS (ESI) m/z 347 (M+H)$^+$.

Example 25

N-{[trans-5-amino-4-(2,4,5-trifluorophenyl)cyclohex-1-en-1-yl]methyl}pyridin-2-amine The title compound was synthesized using the procedure as described in Example 20D by substituting 2-aminopyridine for N-acylpiperizine. $^1$H NMR (300 MHz, methanol-$d_4$) δ ppm 2.26-2.41 (m, 1H), 2.39-2.52 (m, 2H), 2.52-2.63 (m, 1H), 3.75-3.90 (m, 1H), 4.02 (s, 2H), 5.86 (s, 1H), 6.90-6.99 (m, 1H), 7.10 (d, J=9.15 Hz, 1H), 7.19-7.31 (m, 1H), 7.33-7.44 (m, 1H), 7.85-7.91 (m, J=5.76 Hz, 1H), 7.92-8.02 (m, 1H), 7.93-8.02 (m, 1H). MS (ESI) m/z 334 (M+H)$^+$.

Example 26

N-{[trans-5-amino-4-(2,4,5-trifluorophenyl)cyclohex-1-en-1-yl]methyl}-N-[4-(methylsulfonyl)phenyl]amine The title compound was synthesized using the procedure as described in Example 20D by substituting 4-methylsulfonylaniline for N-acylpiperizine. $^1$H NMR (300 MHz, methanol-$d_4$) δ ppm 2.12-2.31 (m, 1H), 2.46 (s, 3H), 3.02 (s, 3H), 3.17-3.28 (m, 1H), 3.70-3.88 (m, 3H), 5.85 (s, 1H), 6.72 (d, J=9.15 Hz, 2H), 7.13-7.29 (m, 1H), 7.31-7.43 (m, 1H), 7.63 (d, J=8.82 Hz, 2H). MS (ESI) m/z 411 (M+H)$^+$.

Example 27

4-({[trans-5-amino-4-(2,4,5-trifluorophenyl)cyclohex-1-en-1-yl]methyl}amino)-N,N-dimethylbenzamide

Example 27A tert-butyl 3-[(dimethylamino)carbonyl]phenylcarbamate

3-N-BOC-aminobenzoic acid (200 mg, 0.84 mmol), N'N-dimethylamine (2M in tetrahydrofuran, 1.2 mL, 2.52 mmol), O-benzotriazol-1-yl-N,N,N',N'-tetramethyluronium tetrafluoroborate (352 mg, 1.1 mmol), and triethylamine (0.24 mL, 1.68 mmol) were mixed in N,N-dimethylformamide (1 mL). The mixture was stirred for two hours at room temperature. Water (10 mL) was added, and the mixture was extracted with ethyl acetate (3×10 mL). The combined organic layers were dried ($Na_2SO_4$), filtered, and concentrated under reduced pressure. The crude product was purified on silica gel (eluting with 30% ethyl acetate in hexane) to yield the title compound (178 mg, 80%). $^1$H NMR (300 MHz, methanol-$d_4$) δ ppm 1.52 (s, 9H), 3.00 (s, 3H), 3.09 (s, 3H), 7.02 (d, J=7.46 Hz, 1H), 7.33 (t, J=8.14 Hz, 1H), 7.42-7.49 (m, 1H), 7.51 (t, J=1.70 Hz, 1H). MS (DCI) m/z 365 [M+H]$^+$.

Example 27B 3-amino-N,N-dimethylbenzamide

Example 27A (50 mg) was treated with trifluoroacetic acid/$CH_2Cl_2$ (1 mL:1 mL) and stirred for one hour. The mixture was concentrated to dryness under reduced pressure to give the title compound. $^1$H NMR (300 MHz, methanol-$d_4$) δ ppm 3.66 (d, 6H), 7.43 (d, J=1.70 Hz, 1H), 7.49 (dd, J=7.80, 2.37 Hz, 1H), 7.52-7.58 (m, 1H), 7.63 (d, J=7.80 Hz, 1H). MS (DCI) m/z 265 [M+H]$^+$.

Example 27C 4-({[trans-5-amino-4-(2,4,5-trifluorophenyl)cyclohex-1-en-1-yl]methyl}amino)-N,N-dimethylbenzamide The title compound was synthesized using the procedure as described in Example 20D by substituting Example 27B for N-acylpiperizine. $^1$H NMR (400 MHz, methanol-$d_4$) δ ppm 2.13-2.34 (m, J=2.15 Hz, 1H), 2.39-2.50 (m, 2H), 2.50-2.62 (m, 1H), 2.99 (s, 6H), 3.19-3.29 (m, 1H), 3.70-3.85 (m, 3H), 5.84 (s, 1H), 6.64 (d, J=8.90 Hz, 2H), 7.13-7.28 (m, 3H), 7.31-7.60 (m, 1H). MS (ESI) m/z 404 (M+H)$^+$.

Example 28

N-{[trans-5-amino-4-(2,4,5-trifluorophenyl)cyclohex-1-en-1-yl]methyl}-N-[2-(methylsulfonyl)phenyl]amine The title compound was synthesized using the procedure as described in Example 20D by substituting 2-methylsulfonylaniline for N-acylpiperizine. $^1$H NMR (400 MHz, methanol-$d_4$) δ ppm 2.43-2.50 (m, 2H), 2.51-2.62 (m, 1H), 3.08 (s, 3H), 3.20-3.28 (m, 2H), 3.74-3.84 (m, 1H), 3.93 (s, 2H), 5.89 (s, 1H), 6.81 (t, J=7.52 Hz, 1H), 6.87 (d, J=8.29 Hz, 1H), 7.17-7.27 (m, 1H), 7.32-7.41 (m, 1H), 7.44-7.50 (m, 1H), 7.71 (dd, J=7.98, 1.53 Hz, 1H). MS (ESI) m/z 411 (M+H)$^+$.

Example 29

4-({[trans-5-amino-4-(2,4,5-trifluorophenyl)cyclohex-1-en-1-yl]methyl}amino)benzoic acid The title compound was synthesized using the procedure as described in Example 20D by substituting tert-butyl 4-aminobenzoate for N-acylpiperizine. $^1$H NMR (400 MHz, methanol-d$_4$) δ ppm 2.14-2.31 (m, 1H), 2.41-2.50 (m, 2H), 2.49-2.62 (m, 1H), 3.18-3.28 (m, 1H), 3.70-3.87 (m, 3H), 5.84 (s, 1H), 6.62 (d, J=8.90 Hz, 2H), 7.16-7.26 (m, 1H), 7.31-7.42 (m, 1H), 7.78 (d, J=8.90 Hz, 2H). MS (ESI) m/z 376 (M+H)$^+$.

Example 30

6-({[trans-5-amino-4-(2,4,5-trifluorophenyl)cyclohex-1-en-1-yl]methyl}amino)nicotinamide The title compound was synthesized using the procedure as described in Example 20D by substituting 6-aminonicotinamide for N-acylpiperizine. $^1$H NMR (400 MHz, methanol-d$_4$) δ ppm 2.29-2.40 (m, 1H), 2.41-2.51 (m, 2H), 2.52-2.63 (m, 1H), 3.21-3.30 (m, 1H), 3.80-3.87 (m, 1H), 4.07 (s, 2H), 5.86 (s, 1H), 7.07 (d, J=9.51 Hz, 1H), 7.19-7.28 (m, 1H), 7.31-7.45 (m, 1H), 8.28 (dd, J=9.36, 1.99 Hz, 1H), 8.45 (d, J=1.84 Hz, 1H). MS (ESI) m/z 377 (M+H)$^+$.

Example 31

3-({[trans-5-amino-4-(2,4,5-trifluorophenyl)cyclohex-1-en-1-yl]methyl}amino)benzamide The title compound was synthesized using the procedure as described in Example 20D by substituting 3-aminobenzamide for N-acylpiperizine. $^1$H NMR (400 MHz, methanol-d$_4$) δ ppm 2.21-2.34 (m, J=9.51 Hz, 1H), 2.45 (s, 2H), 2.57 (dd, J=17.18, 4.91 Hz, 1H), 3.20-3.29 (m, 1H), 3.71-3.85 (m, 3H), 5.86 (s, 1H), 6.84 (dd, J=8.13, 1.69 Hz, 1H), 7.08-7.17 (m, 2H), 7.17-7.26 (m, 2H), 7.30-7.41 (m, 1H). MS (ESI) m/z 375 (M+H)$^+$.

Example 32 ethyl 4-{[trans-5-amino-4-(2,4,5-trifluorophenyl)cyclohex-1-en-1-yl]methyl}piperazine-1-carboxylate The title compound was synthesized using the procedure as described in Example 20D by substituting 1-ethoxycarbonylpiperazine for N-acylpiperizine. $^1$H NMR (500 MHz, methanol-d$_4$) δ ppm 1.28 (t, J=7.02 Hz, 3H), 2.38-2.48 (m, 1H), 2.52-2.60 (m, 2H), 2.71 (dd, J=16.78, 5.19 Hz, 1H), 3.20-3.29 (m, 8H), 3.77 (s, 2H), 3.81-3.90 (m, 1H), 4.18 (q, J=7.22 Hz, 2H), 6.16 (s, 1H), 7.20-7.31 (m, 1H), 7.34-7.50 (m, 1H). MS (ESI) m/z 398 (M+H)$^+$.

Example 33 trans-3-{[2-(trifluoromethyl)-5,6-dihydroimidazo[1,2-a]pyrazin-7(8H)-yl]methyl}-6-(2,4,5-trifluorophenyl)cyclohex-3-en-1-amine The title compound was synthesized using the procedure as described in Example 19F by substituting 2-trifluoromethyl-5,6,7,8-tetrahydro-imidazo[1,2-a]pyrazine (prepared as described in D. Kim et al, J. Med. Chem. 2005, 48, 141-151.) for 3-trifluoromethyl-5,6,7,8-tetrahydro-[1,2,4]triazolo[4,3-a]pyrazine. $^1$H NMR (500 MHz, methanol-d$_4$) δ ppm 2.31-2.39 (m, 1H), 2.49-2.57 (m, 2H), 2.71 (dd, J=17.09, 4.88 Hz, 1H), 3.22 (t, J=5.49 Hz, 2H), 3.27 (dd, J=7.48, 2.29 Hz, 1H), 3.46 (s, 2H), 3.79-3.87 (m, 1H), 3.92 (s, 2H), 4.19-4.24 (m, 2H), 5.99 (s, 1H), 7.21-7.28 (m, 1H), 7.38-7.45 (m, 1H), 7.60 (s, 1H). MS (ESI) m/z 431 (M+H)$^+$.

Example 34

N-{[trans-5-amino-4-(2,4,5-trifluorophenyl)cyclohex-1-en-1-yl]methyl}-N-1,3-benzodioxol-5-ylamine The title compound was synthesized using the procedure as described in Example 20D by substituting 3,4-(methylenedioxy)aniline for N-acylpiperizine. $^1$H NMR (400 MHz, methanol-d$_4$) δ ppm 2.23-2.39 (m, 1H), 2.44-2.52 (m, 2H), 2.58 (dd, J=17.95, 5.98 Hz, 1H), 3.17-3.27 (m, 1H), 3.68-3.81 (m, 1H), 3.86 (s, 2H), 5.95 (s, 2H), 5.93 (s, 1H), 6.57 (dd, J=8.44, 2.30 Hz, 1H), 6.70 (d, J=2.15 Hz, 1H), 6.81 (d, J=8.29 Hz, 1H), 7.18-7.28 (m, 1H), 7.30-7.40 (m, 1H). MS (ESI) m/z 376 (M+H)$^+$.

Example 35

N-{[trans-5-amino-4-(2,4,5-trifluorophenyl)cyclohex-1-en-1-yl]methyl}-N-2,3-dihydro-1,4-benzodioxin-6-ylamine The title compound was synthesized using the procedure as described in Example 20D by substituting 3,4-ethylenedioxy aniline for N-acylpiperazine. $^1$H NMR (400 MHz, methanol-d$_4$) δ ppm 2.26-2.38 (m, 1H), 2.43-2.52 (m, 2H), 2.59 (dd, J=16.72, 5.68 Hz, 1H), 3.16-3.27 (m, 1H), 3.71-3.83 (m, 1H), 3.89 (s, 2H), 4.20-4.29 (m, 4H), 5.97 (s, 1H), 6.67-6.73 (m, 1H), 6.76 (d, J=2.45 Hz, 1H), 6.88 (d, J=8.59 Hz, 1H), 7.18-7.29 (m, 1H), 7.31-7.41 (m, 1H). MS (ESI) m/z 391 (M+H)$^+$.

Example 36 trans-3-[(4-phenylpiperazin-1-yl)methyl]-6-(2,4,5-trifluorophenyl)cyclohex-3-en-1-amine The title compound was synthesized using the procedure as described in Example 20D by substituting 1-phenylpiperazine for N-acylpiperizine. $^1$H NMR (400 MHz, methanol-d$_4$) δ ppm 2.42-2.54 (m, 1H), 2.53-2.62 (m, 2H), 2.75 (dd, J=16.88, 4.30 Hz, 1H), 3.41-3.58 (m, 9H), 3.84-3.90 (m, 3H), 6.22 (s, 1H), 6.94 (t, J=7.36 Hz, 1H), 7.03 (d, J=7.98 Hz, 2H), 7.22-7.33 (m, 3H), 7.36-7.46 (m, 1H). MS (ESI) m/z 402 (M+H)$^+$.

Example 37

1-{[trans-5-amino-4-(2,4,5-trifluorophenyl)cyclohex-1-en-1-yl]methyl}piperidine-4-carboxamide The title compound was synthesized using the procedure as described in Example 20D, by substituting isonipecotamide for N-acylpiperizine. $^1$H NMR (400 MHz, methanol-d$_4$) δ ppm 1.89-2.16 (m, 4H), 2.36-2.48 (m, 1H), 2.57 (s, 2H), 2.69 (dd, J=16.72, 4.76 Hz, 1H), 2.98 (s, 1H), 3.25-3.35 (m, 4H), 3.62 (s, 1H), 3.77 (s, 2H), 3.81-3.91 (m, 1H), 6.17 (s, 1H), 7.18-7.35 (m, 1H), 7.34-7.48 (m, 1H). MS (ESI) m/z 368 (M+H)$^+$.

Example 38

Trans-1-{[5-amino-4-(2,4,5-trifluorophenyl)cyclohex-1-en-1-yl]methyl}-L-prolinamide The title compound was synthesized using the procedure as described in Example 20D by substituting L-prolinamide for N-acylpiperizine. $^1$H NMR (500 MHz, methanol-d$_4$) δ ppm 2.00-2.16 (m, 2H), 2.23 (d, J=7.32 Hz, 1H), 2.38 (s, 1H), 2.48-2.69 (m, 3H), 3.19-3.29 (m, 4H), 3.55-3.97 (m, 3H), 4.09-4.21 (m, 1H), 6.17 (s, 1H), 7.22-7.31 (m, 1H), 7.33-7.51 (m, 1H). MS (ESI) m/z 354 (M+H)$^+$.

Example 39 trans-5-amino-N-phenyl-4-(2,4,5-trifluorophenyl)cyclohex-1-ene-1-carboxamide

Example 39A trans-5-[(tert-butoxycarbonyl)amino]-4-(2,4,5-trifluorophenyl)cyclohex-1-ene-1-carboxylic acid To Example 20C (1 g, 2.8 mmol) in dimethyl sulfoxide (4 mL) Na$_2$HPO$_4$ buffer (pH=7, 4 mL) was added followed by NaClO$_2$ (633 mg, 7 mmol). The reaction was stirred for two hours and then 1N HCl was added to the mixture until pH ~2. It was extracted with ethyl acetate (3×), washed with water and brine, and concentrated to give the title compound (1 g, 100%). $^1$H NMR (400 MHz, DMSO-d$_6$) δ ppm 1.20 (s, 9H), 2.09-2.30 (m, 1H), 2.48-2.58 (m, 2H), 2.91-3.08 (m, 1H), 3.72-3.93 (m, 1H), 6.73-6.86 (m, 2H), 7.21-7.55 (m, J=10.74 Hz, 2H), 12.26 (s, 1H). MS (ESI) m/z 372 (M+H)$^+$.

Example 39B trans-5-amino-N-phenyl-4-(2,4,5-trifluorophenyl)cyclohex-1-ene-1-carboxamide Step A Example 39A (50 mg, 0.13 mmol), aniline (0.16 mmol), O-benzotriazol-1-yl-N,N,N',N'-tetramethyluronium tetrafluoroborate (57 mg, 0.17 mmol) and triethylamine (26 uL, 0.26 mmol) were mixed in N,N-dimethylformamide (0.5 mL). The mixture was stirred for two hours at room temperature. It was purified by reverse phase high pressure liquid chromatography (eluting with 0% to 70% acetonitrile/water with 0.1% trifluoroacetic acid).

Step B

The intermediate from step A (50 mg) was treated with trifluoroacetic acid/CH$_2$Cl$_2$ (1 mL:1 mL) and stirred for one hour. The product was purified by reverse phase high pressure liquid chromatography (eluting with 0% to 70% acetonitrile/ 0.1% aqueous trifluoroacetic acid). $^1$H NMR (500 MHz, methanol-d$_4$) δ ppm 2.46-2.57 (m, 1H), 2.57-2.78 (m, 2H), 3.03 (dd, J=17.09, 4.58 Hz, 1H), 3.30-3.37 (m, 1H), 3.79-3.87 (m, 1H), 6.76 (s, 1H), 7.12 (t, J=7.48 Hz, 1H), 7.23-7.30 (m, 1H), 7.33 (t, J=7.93 Hz, 2H), 7.40-7.49 (m, 1H), 7.58 (d, J=8.54 Hz, 1H). MS (ESI) m/z 347 (M+H)$^+$.

Example 40 trans-5-amino-N-benzyl-4-(2,4,5-trifluorophenyl)cyclohex-1-ene-1-carboxamide

The title compound was synthesized using the procedure as described in Example 39B by substituting benzylamine for aniline. $^1$H NMR (400 MHz, methanol-d$_4$) δ ppm 2.37-2.50 (m, 1H), 2.55-2.66 (m, 2H), 2.89-3.00 (dd, J=17.09, 4.58 Hz, 1H), 3.23-3.30 (m, 1H), 3.74-3.84 (m, 1H), 4.45 (s, 2H), 6.64 (s, 1H), 7.19-7.32 (m, 6H), 7.35-7.48 (m, 1H). MS (ESI) m/z 361 (M+H)$^+$.

Example 41

4-({[trans-5-amino-4-(2,4,5-trifluorophenyl)cyclohex-1-en-1-yl]carbonyl}amino)benzamide The title compound was synthesized using the procedure as described in Example 39B by substituting 4-aminobenzamide for aniline. $^1$H NMR (400 MHz, methanol-d$_4$) δ ppm 2.45-2.56 (m, 1H), 2.64-2.77 (m, 2H), 3.05 (dd, J=16.42, 4.76 Hz, 1H), 3.31-3.38 (m, 1H), 3.77-3.89 (m, 1H), 6.80 (s, 1H), 7.19-7.33 (m, 1H), 7.40-7.50 (m, 1H), 7.73 (d, J=8.90 Hz, 2H), 7.87 (d, J=8.90 Hz, 2H). MS (ESI) m/z 390 (M+H)$^+$.

Example 42

2-({[trans-5-amino-4-(2,4,5-trifluorophenyl)cyclohex-1-en-1-yl]methyl}amino)benzamide The title compound was synthesized using the procedure as described in Example 20D by substituting 2-aminobenzamide for N-acylpiperizine. $^1$H NMR (400 MHz, methanol-d$_4$) δ ppm 2.21-2.33 (m, 1H), 2.46 (s, 2H), 2.58 (dd, J=16.42, 5.37 Hz, 1H), 3.19-3.29 (m, 1H), 3.72-3.82 (m, J=5.52 Hz, 1H), 3.85 (s, 2H), 5.87 (s, 1H), 6.64 (t, J=7.67 Hz, 1H), 6.76 (d, J=7.98 Hz, 1H), 7.13-7.26 (m, 1H), 7.27-7.41 (m, 2H), 7.58 (dd, J=7.98, 1.53 Hz, 1H). MS (ESI) m/z 375 (M+H)$^+$.

Example 43 trans-3-(7,8-dihydro[1,3]dioxolo[4,5-g]isoquinolin-6 (5H)-ylmethyl)-6-(2,4,5-trifluorophenyl)cyclohex-3-en-1-amine The title compound was synthesized using the procedure as described in Example 20D by substituting 5,6,7,8-tetrahydro-[1,3]dioxolo[4,5-g]isoquinoline for N-acylpiperizine. $^1$H NMR (400 MHz, methanol-d$_4$) δ ppm 2.42-2.53 (m, 1H), 2.60 (s, 2H), 2.73 (dd, J=16.57, 5.22 Hz, 1H), 3.12 (s, 2H), 3.30-3.41 (m, 4H), 3.84-3.94 (m, 3H), 4.31 (s, 1H), 5.96 (s, 2H), 6.21 (s, 1H), 6.70 (s, 1H), 6.74 (s, 1H), 7.14-7.31 (m, 1H), 7.35-7.47 (m, 1H). MS (ESI) m/z 416 (M+H)$^+$.

Example 44

2-{[trans-5-amino-4-(2,4,5-trifluorophenyl)cyclohex-1-en-1-yl]methyl}-1,2,3,4-tetrahydroisoquinoline-7-carboxamide The title compound was synthesized using the procedure as described in Example 20D by substituting 1,2,3,4-tetrahydroisoquinoline-6-carboxylic acid amide for N-acylpiperizine.

$^1$H NMR (400 MHz, methanol-d$_4$) δ ppm 2.42-2.56 (m, 1H), 2.56-2.66 (m, 2H), 2.69-2.81 (m, J=17.80, 4.60 Hz, 1H), 3.33-3.41 (m, 4H), 3.55-3.72 (m, 1H), 3.86-3.94 (m, 1H), 3.97 (s, 2H), 4.51 (s, 2H), 6.23 (s, 1H), 7.19-7.33 (m, 1H), 7.36-7.47 (m, 2H), 7.73-7.99 (m, 2H). MS (ESI) m/z 416 (M+H)$^+$.

Example 45

3-({[trans-5-amino-4-(2,4,5-trifluorophenyl)cyclohex-1-en-1-yl]methyl}amino)-N-isopropylbenzamide The title compound was synthesized using the procedure as described in Example 20D by substituting 4-amino-N-isopropyl-benzamide for N-acylpiperizine. $^1$H NMR (500 MHz, methanol-d$_4$) δ ppm 1.24 (d, J=6.71 Hz, 6H), 2.20-2.31 (m, 1H), 2.45 (s, 2H), 2.56 (dd, J=16.78, 5.49 Hz, 1H), 3.20-3.29 (m, 1H), 3.72-3.82 (m, 3H), 4.13-4.24 (m, 1H), 5.86 (s, 1H), 6.79 (dd, J=7.78, 1.98 Hz, 1H), 6.99-7.08 (m, 2H), 7.13-7.27 (m, 2H), 7.32-7.41 (m, 1H). MS (ESI) m/z 418 (M+H)$^+$.

Example 46

3-({[trans-5-amino-4-(2,4,5-trifluorophenyl)cyclohex-1-en-1-yl]methyl}amino)benzoic acid The title compound was synthesized using the procedure as described in Example 20D by substituting tert-butyl 3-aminobenzoate for N-acylpiperizine. $^1$H NMR (400 MHz, methanol-d$_4$) δ ppm 2.20-2.33 (m, 1H), 2.46 (s, 2H), 2.58 (dd, J=16.26, 5.22 Hz, 1H), 3.20-3.27 (m, J=6.44 Hz, 1H), 3.70-3.83 (m, 3H), 4.81 (s, 2H), 5.87 (s, 1H), 6.82-6.90 (m, J=7.36, 1.84 Hz, 1H), 7.14-7.25 (m, 2H), 7.31-7.41 (m, 1H). MS (ESI) m/z 377 (M+H)$^+$.

Example 47

N-[3-({[trans-5-amino-4-(2,4,5-trifluorophenyl)cyclohex-1-en-1-yl]methyl}amino)phenyl]acetamide The title compound was synthesized using the procedure as described in Example 20D by substituting 4-aminoacetanilide for N-acylpiperizine. $^1$H NMR (500 MHz, methanol-d$_4$) δ ppm 2.11 (s, 3H), 2.21-2.32 (m, 1H), 2.43-2.50 (m, J=5.19 Hz, 2H), 2.50-2.59 (m, 1H), 3.21-3.29 (m, 1H), 3.73-3.81 (m, 3H), 5.87 (s, 1H), 6.47-6.53 (m, 1H), 6.61-6.67 (m, 1H), 7.08 (t, J=8.09 Hz, 1H), 7.16-7.26 (m, 1H), 7.29 (s, 1H), 7.33-7.42 (m, 1H). MS (ESI) m/z 389 (M+H)$^+$.

Example 48

1-acetyl-N-{[trans-5-amino-4-(2,4,5-trifluorophenyl)cyclohex-1-en-1-yl]methyl}indolin-6-amine The title compound was synthesized using the procedure as described in Example 20D by substituting 1-acetyl-6-amino-2,3-dihydro-(1H)-indole for N-acylpiperizine. $^1$H NMR (500 MHz, methanol-d$_4$) δ ppm 2.22 (s, 3H), 2.25-2.36 (m, 1H), 2.40-2.52 (m, 2H), 2.58 (dd, J=17.24, 5.03 Hz, 1H), 3.14-3.27 (m, 3H), 3.73-3.90 (m, 3H), 4.13 (t, J=8.39 Hz, 2H), 5.92 (s, 1H), 6.82 (dd, J=8.54, 1.53 Hz, 1H), 6.92 (s, 1H), 7.18-7.28 (m, 1H), 7.29-7.40 (m, 1H), 8.03 (d, J=8.54 Hz, 1H). MS (ESI) m/z 416 (M+H)$^+$.

Example 49

1-[3-({[trans-5-amino-4-(2,4,5-trifluorophenyl)cyclohex-1-en-1-yl]methyl}amino)phenyl]ethanone The title compound was synthesized using the procedure as described in Example 20D by substituting 3'-aminoacetophenone for N-acylpiperizine. $^1$H NMR (400 MHz, methanol-d$_4$) δ ppm 2.14-2.34 (m, J=9.21 Hz, 1H), 2.40-2.50 (m, 2H), 2.52-2.62 (m, 4H), 3.20-3.27 (m, 1H), 3.72-3.84 (m, 3H), 5.87 (s, 1H), 6.80-6.93 (m, 1H), 7.16-7.29 (m, 4H), 7.30-7.40 (m, 1H). MS (ESI) m/z 374 (M+H)$^+$.

Example 50

3-({[trans-5-amino-4-(2,4,5-trifluorophenyl)cyclohex-1-en-1-yl]methyl}amino)-N-methylbenzamide The title compound was synthesized using the procedure as described in Example 20D by substituting 3-aminobenzoylmethylamide for N-acylpiperizine. $^1$H NMR (500 MHz, methanol-d$_4$) δ ppm 2.28 (s, 1H), 2.38-2.49 (m, 2H), 2.56 (dd, J=16.78, 5.49 Hz, 1H), 2.90 (s, 3H), 3.21-3.28 (m, 1H), 3.71-3.81 (m, 3H), 5.86 (s, 1H), 6.79 (dd, J=8.09, 2.29 Hz, 1H), 7.00 (d, J=7.63 Hz, 1H), 7.07 (d, J=1.83 Hz, 1H), 7.13-7.26 (m, 2H), 7.29-7.45 (m, 1H). MS (ESI) m/z 390 (M+H)$^+$.

Example 51

2-{[trans-5-amino-4-(2,4,5-trifluorophenyl)cyclohex-1-en-1-yl]methyl}-1,2,3,4-tetrahydroisoquinoline-7-carbonitrile The title compound was synthesized using the procedure as described in Example 20D by substituting 7-cyano-1,2,3,4-tetrahydroisoquinoline for N-acylpiperizine. $^1$H NMR (500 MHz, methanol-d$_4$) δ ppm 2.42-2.68 (m, 3H), 2.75 (dd, J=16.94, 5.03 Hz, 1H), 3.34-3.40 (m, 6H), 3.62 (dd, J=14.49, 7.48 Hz, 2H), 3.84-3.94 (m, 1H), 3.96 (s, 2H), 4.40-4.58 (m, 1H), 6.23 (s, 1H), 7.22-7.32 (m, 1H), 7.38-7.45 (m, 1H), 7.48 (d, J=7.93 Hz, 1H), 7.61-7.74 (m, 2H). MS (ESI) m/z 398 (M+H)$^+$.

Example 52

[3-({[trans-5-amino-4-(2,4,5-trifluorophenyl)cyclohex-1-en-1-yl]methyl}amino)phenyl]acetic acid The title compound was synthesized using the procedure as described in Example 20D by substituting (3-aminophenyl)acetic acid for N-acylpiperizine. $^1$H NMR (500 MHz, methanol-d$_4$) δ ppm 2.14-2.32 (m, 1H), 2.36-2.50 (m, 2H), 2.56 (dd, J=16.48, 5.49 Hz, 1H), 3.20-3.27 (m, 1H), 3.50 (s, 2H), 3.71-3.80 (m, 3H), 5.86 (s, 1H), 6.54-6.68 (m, 3H), 7.09 (t, J=7.78 Hz, 1H), 7.17-7.26 (m, 1H), 7.32-7.42 (m, 1H). MS (ESI) m/z 391 (M+H)$^+$.

Example 53

N-{[trans-5-amino-4-(2,4,5-trifluorophenyl)cyclohex-1-en-1-yl]methyl}-N-[3-methoxy-5-(trifluoromethyl)phenyl]amine The title compound was synthesized using the procedure as described in Example 20D by substituting 3-methoxy-5-(trifluoromethyl)aniline for N-acylpiperizine. $^1$H NMR (500 MHz, methanol-d$_4$) δ ppm 2.26 (d, J=10.07 Hz, 1H), 2.35-2.52 (m, 2H), 2.58 (dd, J=17.24, 5.34 Hz, 1H), 3.17-3.26 (m, 1H), 3.72-3.82 (m, 6H), 5.86 (s, 1H), 6.35 (s, 1H), 6.39 (s, 1H), 6.47 (s, 1H), 7.16-7.27 (m, 1H), 7.33-7.42 (m, 1H). MS (ESI) m/z 431 (M+H)$^+$.

Example 54

3-({[trans-5-amino-4-(2,45-trifluorophenyl)cyclohex-1-en-1-yl]methyl}amino)benzonitrile The title compound was synthesized using the procedure as described in Example 20D by substituting 3-aminobezonitrile for N-acylpiperizine. $^1$H NMR (500 MHz, methanol-d$_4$) δ ppm 2.11-2.31 (m, J=16.78, 9.46 Hz, 1H), 2.46 (s, 2H), 2.56 (dd, J=16.78, 4.88 Hz, 1H), 3.18-3.28 (m, 1H), 3.68-3.84 (m, 3H), 5.84 (s, 1H), 6.82-6.94 (m, 3H), 7.17-7.27 (m, 2H), 7.32-7.42 (m, 1H). MS (ESI) m/z 358 (M+H)$^+$.

Example 55

N-{[trans-5-amino-4-(2,4,5-trifluorophenyl)cyclohex-1-en-1-yl]methyl}-N-(3-methylphenyl)amine The title compound was synthesized using the procedure as described in Example 20D by substituting m-toluidine for N-acylpiperizine. $^1$H NMR (300 MHz, methanol-d$_4$) δ ppm 2.25 (s, 3H), 2.40-2.49 (m, 3H), 2.51-2.65 (m, 1H), 3.15-3.26 (m, 1H), 3.68-3.82 (m, 3H), 5.86 (s, 1H), 6.50-6.62 (m, J=6.10 Hz, 3H), 7.05 (t, J=8.14 Hz, 1H), 7.15-7.29 (m, 1H), 7.30-7.44 (m, 1H). MS (ESI) m/z 347 (M+H)$^+$.

Example 56

N-{[trans-5-amino-4-(2,4,5-trifluorophenyl)cyclohex-1-en-1-yl]methyl}-N-(3-chlorophenyl)amine The title compound was synthesized using the procedure as described in Example 20D by substituting 3-chloroaniline for N-acylpiperizine. $^1$H NMR (400 MHz, methanol-d$_4$) δ ppm 2.27 (s, 1H), 2.39-2.48 (m, 2H), 2.56 (dd, J=17.18, 6.14 Hz, 1H), 3.16-3.28 (m, 1H), 3.70-3.82 (m, 3H), 5.84 (s, 1H), 6.47-6.64 (m, 3H), 7.04 (t, J=7.98 Hz, 1H), 7.17-7.26 (m, 1H), 7.29-7.44 (m, 1H). MS (ESI) m/z 367, 369 (M+H)$^+$.

Example 57

N-{[trans-5-amino-4-(2,4,5-trifluorophenyl)cyclohex-1-en-1-yl]methyl}-N-(3-fluorophenyl)amine The title compound was synthesized using the procedure as described in Example 20D by substituting 3-fluoro-aniline for N-acylpiperizine. $^1$H NMR (400 MHz, methanol-d$_4$) δ ppm 2.17-2.32 (m, 1H), 2.40-2.51 (m, 2H), 2.52-2.62 (m, J=7.98 Hz, 1H), 3.17-3.27 (m, 1H), 3.71-3.81 (m, 3H), 5.84 (s, 1H), 6.20-6.35 (m, 2H), 6.37-6.45 (m, 1H), 6.96-7.12 (m, 1H), 7.17-7.27 (m, 1H), 7.29-7.55 (m, 1H). MS (ESI) m/z 351 (M+H)$^+$.

Example 58

2-{[trans-5-amino-4-(2,4,5-trifluorophenyl)cyclohex-1-en-1-yl]methyl}-1H-isoindole-1,3(2H)-dione

Example 58A tert-butyl trans-3-[(1,3-dioxo-1,3-dihydro-2H-isoindol-2-yl)methyl]-6-(2,4,5-trifluorophenyl)cyclohex-3-en-1-ylcarbamate Example 20B (404 mg, 1.13 mmol), triphenylphosphine (455 mg, 1.6 eq.) and phthalamide (222 mg, 1.4 eq.) were mixed in 3.5 mL of toluene. Then, di-tert-butylazodicarboxylate (DBAD, 398 mg, 1.6 eq.) was added. The reaction flask was flushed with argon and then heated to 90° C. After stirring overnight at 90° C., the mixture was cooled to room temperature, concentrated and the resulting oil was purified by column chromatography (eluting with 20% to 40% ethyl acetate in hexane) to give the title compound (684 mg).

Example 58B

2-{[trans-5-amino-4-(2,4,5-trifluorophenyl)cyclohex-1-en-1-yl]methyl}-1H-isoindole-1,3(2H)-dione Example 58A (35.5 mg) in 0.75 mL of CH$_2$Cl$_2$ was treated with 0.75 mL of trifluoroacetic acid. After stirring for two hours, the mixture was purified by reverse-phase high pressure liquid chromatography (eluting with 0-70% acetonitrile/water and 0.1% trifluoroacetic acid) to give the title compound. $^1$H NMR (500 MHz, methanol-d$_4$) δ ppm 2.22-2.32 (m, 1H), 2.40-2.49 (m, 2H), 2.56 (dd, J=17.24, 5.03 Hz, 1H), 3.19-3.27 (m, 1H), 3.72-3.82 (m, 1H), 4.28 (s, 2H), 5.83 (s, 1H), 7.17-7.25 (m, 1H), 7.31-7.40 (m, 1H), 7.81-7.86 (m, 2H), 7.86-7.92 (m, 2H). MS (ESI) m/z 387 (M+H)$^+$.

Example 59 trans-3-(phenoxymethyl)-6-(2,4,5-trifluorophenyl)cyclohex-3-en-1-amine

Step A

Example 20B (50 mg, 0.14 mmol), triphenylphosphine (58 mg, 0.220 mmol) and phenol (0.17 mmol) were mixed in 1 mL of dry toluene. Then, di-tert-butylazodicarboxylate (21 mg, 0.22 mmol) was added. The reaction mixture was heated at 90° C. for two hours, cooled to room temperature, and purified by reverse-phase high pressure liquid chromotography (eluting with 0% to 70% acetonitrile/water with 0.1% trifluoroacetic acid).

Step B

The intermediate from step A (50 mg) was treated with trifluoroacetic acid/CH$_2$Cl$_2$ (1 mL:1 mL) and stirred for one hour. The product was purified by reverse phase high pressure liquid chromatography (eluting with 0% to 70% acetonitrile/water with 0.1% trifluoroacetic acid). $^1$H NMR (400 MHz, methanol-d$_4$) δ ppm 2.25-2.41 (m, 1H), 2.47-2.53 (m, 2H), 2.69 (dd, J=17.95, 5.68 Hz, 1H), 3.22-3.30 (m, 1H), 3.70-3.86 (m, 1H), 4.53 (s, 2H), 5.99 (s, 1H), 6.89-6.98 (m, 3H), 7.15-7.31 (m, 3H), 7.35-7.45 (m, 1H). MS (ESI) m/z 334 (M+H)$^+$.

Example 60 trans-3-{[4-(methylsulfonyl)phenoxy]methyl}-6-(2,4,5-trifluorophenyl)cyclohex-3-en-1-amine The title compound was synthesized using the procedure as described in Example 59 by substituting 4-methylsulfonylphenol for phenol. $^1$H NMR (400 MHz, methanol-$d_4$) δ ppm 2.29-2.44 (m, 1H), 2.46-2.56 (m, 2H), 2.61-2.75 (m, 1H), 3.08 (s, 3H), 3.22-3.30 (m, 1H), 3.75-3.88 (m, 1H), 4.66 (s, 2H), 6.05 (s, 1H), 7.11-7.19 (m, 2H), 7.20-7.30 (m, 1H), 7.33-7.45 (m, 1H), 7.77-7.96 (m, 2H). MS (ESI) m/z 411 (M+H)$^+$.

Example 61

3-{[trans-5-amino-4-(2,4,5-trifluorophenyl)cyclohex-1-en-1-yl]methoxy}benzamide

The title compound was synthesized using the procedure as described in Example 59 by substituting 3-hydroxybenzamide for phenol. $^1$H NMR (400 MHz, methanol-$d_4$) δ ppm 2.27-2.43 (m, 1H), 2.51 (s, 2H), 2.66-2.75 (m, J=7.06 Hz, 1H), 3.73-3.91 (m, 1H), 4.60 (s, 2H), 6.02 (s, 1H), 7.08-7.17 (m, 1H), 7.19-7.29 (m, 1H), 7.34-7.42 (m, 2H), 7.42-7.48 (m, 2H). MS (ESI) m/z 377 (M+H)$^+$.

Example 62

2-{[trans-5-amino-4-(2,4,5-trifluorophenyl)cyclohex-1-en-1-yl]carbonyl}-1,2,3,4-tetrahydroisoquinoline-7-carboxamide The title compound was synthesized as described in Example 39B by substituting 1,2,3,4-tetrahydro-isoquinoline-7-carboxylic acid amide for aniline. $^1$H NMR (500 MHz, methanol-$d_4$) δ ppm 2.49 (s, 1H), 2.64 (s, 2H), 2.73-2.85 (m, 1H), 2.99 (t, J=5.65 Hz, 2H), 3.31-3.40 (m, 3H), 3.89 (t, J=5.95 Hz, 3H), 6.11 (s, 1H), 7.21-7.34 (m, 2H), 7.40-7.50 (m, 1H), 7.65-7.76 (m, 2H). MS (ESI) m/z 430 (M+H)$^+$.

Example 63

1-{[trans-5-amino-4-(2,4,5-trifluorophenyl)cyclohex-1-en-1-yl]carbonyl}piperidine-4-carboxamide The title compound was synthesized as described in Example 39B by substituting isonipecotamide for aniline. $^1$H NMR (500 MHz, methanol-$d_4$) δ ppm 1.53-1.72 (m, 2H), 1.83-1.92 (m, 2H), 2.39-2.64 (m, 3H), 2.75 (dd, J=17.09, 4.88 Hz, 1H), 3.27-3.37 (m, 6H), 3.80-3.89 (m, 1H), 5.99 (s, 1H), 7.14-7.31 (m, 1H), 7.35-7.52 (m, 1H). MS (ESI) m/z 382 (M+H)$^+$.

Example 64

N-{[trans-5-amino-4-(2,4,5-trifluorophenyl)cyclohex-1-en-1-yl]methyl}-6-thien-3-ylpyrimidin-4-amine

Example 64A tert-butyl trans-3-(aminomethyl)-6-(2,4,5-trifluorophenyl)cyclohex-3-en-1-ylcarbamate A solution of Example 58A (650 mg, 1.07 mmol) in 3 mL each of CH$_2$Cl$_2$ and methanol was treated with hydrazine hydrate (336 µL). Ethyl acetate and 1N NaOH were added. The organic phase was dried (Na$_2$SO$_4$) and concentrated in vacuo to give the title compound.

Example 64B 4-chloro-6-thien-3-ylpyrimidine

Thiophene-3-boronic acid (2.6 g, 20 mmol) was combined with 4,6-dichloropyrimidine (3.6 g, 24 mmol, 1.2 eq), bis(triphenylphosphine)palladium(II)dichloride (200 mg), and 3.0 g sodium carbonate in a resealable pressure flask. Sixty mL of a mixed solvent (N,N-dimethyl formamide/dimethyl ether/methanol/water 1:1:0.3:0.4 mL) was added, and the solution was purged with nitrogen prior to sealing. The reaction mixture was heated at 130° C. for three hours. The crude reaction mixture was cooled, partitioned between water and ethyl acetate. The organic material was washed with brine and dried over sodium sulfate. After concentrating to half-volume in vacuo, the resultant slurry was allowed to stand overnight, and then filtered to collect a white solid, which was washed with a small volume of ethyl acetate. The combined organic filtrates were chromatographed on silica gel (eluting with a gradient of 0%->5%->20% ethyl acetate in hexanes) to produce a second crop of solid material. The combined yield for the two batches was 1.83 g (46% yield).

Example 64C tert-butyl trans-3-{[(6-thien-2-ylpyrimidin-4-yl)amino]methyl}-6-(2,4,5-trifluorophenyl)cyclohex-3-en-1-ylcarbamate Example 64A (67 mg, <0.188 mmol), Example 64B (50 mg, 0.253 mmol), and diisopropylethyl amine (94 µL, 0.54 mmol) were mixed in 1.5 mL of isopropanol. The reaction tube was heated to 100° C. and stirred for ten minutes in a microwave reactor. The mixture was cooled to room temperature, and then purified by reverse-phase high pressure liquid chromatography (eluting with 0-70% acetonitrile/water and 0.1% trifluoroacetic acid) to give the title compound (37 mg).

Example 64D

N-{[trans-5-amino-4-(2,4,5-trifluorophenyl)cyclohex-1-en-1-yl]methyl}-6-thien-3-ylpyrimidin-4-amine Example 64C (35 mg) in 0.75 mL of CH$_2$Cl$_2$ was treated with 0.75 mL of trifluoroacetic acid. After stirring for two hours, the mixture was purified by reverse-phase high pressure liquid chromatography (eluting with 0-70% acetonitrile/water and 0.1% trifluoroacetic acid) to give the title compound. $^1$H NMR (500 MHz, methanol-$d_4$) δ ppm 2.29-2.39 (m, 1H), 2.41-2.53 (m, 2H), 2.58 (dd, J=16.78, 4.88 Hz, 1H), 3.23-3.31 (m, 1H), 3.74-3.88 (m, 1H), 4.26 (s, 2H), 5.86 (s, 1H), 7.05 (s, 1H), 7.17-7.28 (m, 1H), 7.32-7.43 (m, 1H), 7.62 (d, J=5.19 Hz, 1H), 7.75 (dd, J=5.03, 2.90 Hz, 1H), 8.29 (s, 1H), 8.67 (s, 1H). MS (ESI) m/z 417 (M+H)$^+$.

Example 65

4-{[trans-5-amino-4-(2,4,5-trifluorophenyl)cyclohex-1-en-1-yl]methoxy}benzamide

The title compound was synthesized using the procedure as described in Example 59 by substituting 4-hydroxybenzamide for phenol. ¹H NMR (500 MHz, methanol-d₄) δ ppm 2.28-2.40 (m, J=16.78 Hz, 1H), 2.42-2.59 (m, 2H), 2.64-2.74 (m, 1H), 3.23-3.31 (m, 2H), 3.71-3.89 (m, 1H), 4.61 (s, 2H), 6.03 (s, 1H), 7.01 (d, J=8.85 Hz, 1H), 7.17-7.30 (m, 1H), 7.32-7.45 (m, 1H), 7.85 (d, J=8.85 Hz, 2H). MS (ESI) m/z 377 (M+H)⁺.

Example 66

N-(3-{[trans-5-amino-4-(2,4,5-trifluorophenyl)cyclohex-1-en-1-yl]methoxy}phenyl)-N,N-dimethylamine The title compound was synthesized using the procedure as described in Example 59 by substituting 4-N,N'-dimethylaminophenol for phenol. ¹H NMR (500 MHz, methanol-d₄) δ ppm 2.29-2.43 (m, 1H), 2.45-2.56 (m, 2H), 2.70 (dd, J=16.94, 5.03 Hz, 1H), 3.22 (s, 6H), 3.26-3.31 (m, 1H), 3.74-3.88 (m, 1H), 4.59 (s, 2H), 6.03 (s, 1H), 6.93-7.01 (m, 1H), 7.03-7.07 (m, 2H), 7.21-7.26 (m, 1H), 7.35-7.48 (m, 2H). MS (ESI) m/z 376 (M+H)⁺.

Example 67 trans-3-[(1,3-benzodioxol-5-yloxy)methyl]-6-(2,4,5-trifluorophenyl)cyclohex-3-en-1-amine The title compound was synthesized using the procedure as described in Example 59 by substituting sesamol for phenol. ¹H NMR (400 MHz, methanol-d₄) δ ppm 2.23-2.40 (m, 1H), 2.44-2.52 (m, 2H), 2.68 (dd, J=17.18, 5.52 Hz, 1H), 3.20-3.29 (m, 1H), 3.73-3.86 (m, 1H), 4.45 (s, 2H), 5.88 (s, 1H), 5.94-5.99 (s, 2H), 6.39 (dd, J=8.29, 2.45 Hz, 1H), 6.53 (d, J=2.46 Hz, 1H), 6.70 (d, J=8.29 Hz, 1H), 7.08-7.30 (m, 1H), 7.32-7.45 (m, 1H). MS (ESI) m/z 377 (M+H)⁺.

Example 68 trans-3-{[2-(methylsulfonyl)phenoxy]methyl}-6-(2,4,5-trifluorophenyl)cyclohex-3-en-1-amine The title compound was synthesized using the procedure as described in Example 59 by substituting 2-methylsulfonylphenol for phenol. ¹H NMR (400 MHz, methanol-d₄) δ ppm 2.34-2.47 (m, 1H), 2.48-2.60 (m, 2H), 2.78 (dd, J=17.03, 5.06 Hz, 1H), 3.25 (s, 3H), 3.26-3.30 (m, 1H), 3.74-3.89 (m, 1H), 4.77 (s, 2H), 6.11 (s, 1H), 7.11-7.33 (m, 3H), 7.33-7.45 (m, 1H), 7.63-7.72 (m, 1H), 7.92 (dd, J=7.83, 1.69 Hz, 1H). MS (ESI) m/z 412 (M+H)⁺.

Example 69

N-(3-{[trans-5-amino-4-(2,4,5-trifluorophenyl)cyclohex-1-en-1-yl]methoxy}phenyl)acetamide The title compound was synthesized using the procedure as described in Example 59 by substituting 3-acetamidophenol for phenol. ¹H NMR (400 MHz, methanol-d₄) δ ppm 2.12 (s, 3H), 2.24-2.41 (m, J=9.82 Hz, 1H), 2.47-2.55 (m, 2H), 2.67 (dd, J=16.72, 5.06 Hz, 1H), 3.26-3.29 (m, 1H), 3.73-3.87 (m, 1H), 4.53 (s, 2H), 6.00 (s, 1H), 6.69 (dd, J=8.13, 1.99 Hz, 1H), 6.84-6.95 (m, 1H), 7.11-7.27 (m, 2H), 7.34-7.45 (m, 1H), 7.48 (t, J=2.15 Hz, 1H). MS (ESI) m/z 391 (M+H)⁺.

Example 70

3-{[trans-5-amino-4-(2,4,5-trifluorophenyl)cyclohex-1-en-1-yl]methoxy}-4-fluorobenzoic acid

Example 70A tert-butyl 4-fluoro-3-hydroxybenzoate

4-Fluoro-3-hydroxybenzoic acid (500 mg, 3.2 mmol) was stirred in toluene (4 mL) and heated to 80° C. N,N-dimethylformamide di-t-butyl acetal (1.9 ml, 7.97 mmol) was added in portions. The mixture was stirred for 2 hours at , and then concentrated. It was purified by column chromatography (eluting with 0-70% acetonitrile/water and 0.1% trifluoroacetic acid) to give the title compound (300 mg, 44%). MS (DCI) m/z 213 (M+H)⁺.

Example 70B

3-{[trans-5-amino-4-(2,4,5-trifluorophenyl)cyclohex-1-en-1-yl]methoxy}-4-fluorobenzoic acid The title compound was synthesized using the procedure as described in Example 59 by substituting Example 70A for phenol. ¹H NMR (500 MHz, methanol-d₄) δ ppm 2.36-2.46 (m, J=17.09 Hz, 1H), 2.44-2.56 (m, 2H), 2.74 (dd, J=16.63, 5.03 Hz, 1H), 3.25-3.28 (m, 1H), 3.73-3.90 (m, 1H), 4.66 (s, 2H), 6.05 (s, 1H), 7.12-7.29 (m, 2H), 7.34-7.44 (m, 1H), 7.61-7.71 (m, 1H), 7.76 (dd, J=8.24, 1.83 Hz, 1H). MS (ESI) m/z 420 (M+H)⁺.

Example 71 trans-3-{[2-chloro-5-(trifluoromethyl)phenoxy]methyl}-6-(2,4,5-trifluorophenyl)cyclohex-3-en-1-amine The title compound was synthesized using the procedure as described in Example 59 by substituting 2-chloro-5-(trifluoromethyl)phenol for phenol. ¹H NMR (500 MHz, methanol-d₄) δ ppm 2.32-2.48 (m, 1H), 2.48-2.60 (m, 2H), 2.78 (dd, J=17.09, 5.19 Hz, 1H), 3.26-3.29 (m, 1H), 3.75-3.90 (m, 1H), 4.69 (s, 2H), 6.09 (s, 1H), 7.19-7.31 (m, 2H), 7.34-7.45 (m, 2H), 7.59 (d, J=8.24 Hz, 1H). MS (ESI) m/z 436, 438 (M+H)⁺.

Example 72 trans-3-[(1-naphthyloxy)methyl]-6-(2,4,5-trifluorophenyl)cyclohex-3-en-1-amine

The title compound was synthesized using the procedure as described in Example 59 by substituting 1-naphthol for phenol. ¹H NMR (400 MHz, methanol-d₄) δ ppm 2.40-2.50 (m, 1H), 2.51-2.58 (m, 2H), 2.73 (dd, J=17.09, 5.19 Hz, 1H), 3.30-3.38 (m, 1H), 3.65-3.99 (m, 1H), 4.75 (s, 2H), 6.11 (s, 1H), 6.95 (d, J=7.67 Hz, 1H), 7.14-7.31 (m, 1H), 7.32-7.53 (m, 5H), 7.81 (d, J=7.36 Hz, 1H), 8.24 (d, J=7.98 Hz, 1H). MS (ESI) m/z 384 (M+H)⁺.

Example 73

3-({[trans-5-amino-4-(2,4,5-trifluorophenyl)cyclohex-1-en-1-yl]carbonyl}amino)benzamide The title compound was synthesized using the procedure as described in Example 39B by substituting 3-aminobenzamide for aniline. ¹H NMR (500 MHz, methanol-d₄) δ ppm 2.47-2.60 (m, 1H), 2.60-2.78 (m, 2H), 3.05 (dd, J=16.94, 5.34 Hz, 1H), 3.31-3.39 (m, 1H), 3.78-3.88 (m, 1H), 6.80 (s, 1H), 7.20-7.32 (m, 1H), 7.39-7.49 (m, 2H), 7.61 (d, J=7.93 Hz, 1H), 7.79 (dd, J=8.09, 1.37 Hz, 1H), 8.08 (s, 1H). MS (ESI) m/z 390 (M+H)⁺.

Example 74 trans-N-[3-(acetylamino)phenyl]-5-amino-4-(2,4,5-trifluorophenyl)cyclohex-1-ene-1-carboxamide The title compound was synthesized using the procedure as described in Example 39B by substituting N-(3-aminophenyl)acetamide for aniline. ¹H NMR (500 MHz, methanol-d₄) δ ppm 2.11 (s, 3H), 2.38-2.54 (m, 1H), 2.60-2.79 (m, 2H), 3.03 (dd, J=18.46, 6.26 Hz, 1H), 3.31-3.39 (m, 1H), 3.78-3.88 (m, 1H), 6.75 (s, 1H), 7.28 (s, 1H), 7.41-7.48 (m, 1H), 7.49-7.56 (m, J=2.14 Hz, 5H). MS (ESI) m/z 403 (M+H)⁺.

Example 75 trans-5-amino-N-1,3-benzodioxol-5-yl-4-(2,4,5-trifluorophenyl)cyclohex-1-ene-1-carboxamide The title compound was synthesized using the procedure as described in Example 39B by substituting 3,4-(methylenedioxy)aniline for aniline. ¹H NMR (500 MHz, methanol-d₄) δ ppm 2.41-2.52 (m, 1H), 2.58-2.74 (m, 2H), 3.01 (dd, J=17.55, 5.34 Hz, 1H), 3.31-3.36 (m, 1H), 3.78-3.86 (m, 1H), 5.94 (s, 2H), 6.68-6.74 (m, 1H), 6.78 (d, J=8.54 Hz, 1H), 6.95 (dd, J=8.39, 1.98 Hz, 1H), 7.20 (d, J=2.14 Hz, 1H), 7.22-7.33 (m, 1H), 7.40-7.48 (m, 1H). MS (ESI) m/z 391 (M+H)⁺.

Example 76

6-({[trans-5-amino-4-(2,4,5-trifluorophenyl)cyclohex-1-en-1-yl]carbonyl}amino)nicotinamide The title compound was synthesized using the procedure as described in Example 39B by substituting 6-aminonicotinamide for aniline. ¹H NMR (400 MHz, methanol-d₄) δ ppm 2.46-2.60 (m, J=3.07 Hz, 1H), 2.60-2.81 (m, 2H), 3.07 (dd, J=17.18, 4.91 Hz, 1H), 3.30-3.44 (m, 1H), 3.78-3.90 (m, 1H), 6.90 (s, 1H), 7.20-7.35 (m, 1H), 7.38-7.52 (m, 1H), 8.14-8.31 (m, 2H), 8.83 (s, 1H). MS (ESI) m/z 391 (M+H)⁺.

Example 77

3-({[trans-5-amino-4-(2,4,5-trifluorophenyl)cyclohex-1-en-1-yl]carbonyl}amino)-N-methylbenzamide The title compound was synthesized using the procedure as described in Example 39B by substituting 3-aminobenzoylmethylamide for aniline. ¹H NMR (500 MHz, methanol-d₄) δ ppm 2.41-2.55 (m, 1H), 2.58-2.79 (m, 2H), 2.92 (s, 3H), 3.05 (dd, J=17.09, 4.88 Hz, 1H), 3.32-3.39 (m, 1H), 3.77-3.89 (m, 1H), 6.80 (s, 1H), 7.18-7.33 (m, 1H), 7.39-7.49 (m, 2H), 7.53 (d, J=7.93 Hz, 1H), 7.77 (dd, J=7.48, 1.68 Hz, 1H), 8.04 (s, 1H). MS (ESI) m/z 404 (M+H)⁺.

Example 78 trans-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine The title compound was synthesized using the procedure as described in Example 39B by substituting 2-trifluoromethyl-5,6,7,8-tetrahydroimidazo[1,2-a]pyrazine (prepared as described in D. Kim et al, J. Med. Chem. 2005, 48, 141-151) for aniline. ¹H NMR (300 MHz, methanol-d₄) δ ppm 2.37-2.56 (m, 1H), 2.59-2.68 (m, 2H), 2.84 (dd, J=16.95, 4.75 Hz, 1H), 3.33-3.41 (m, 1H), 3.74-3.94 (m, 1H), 4.03-4.28 (m, 4H), 4.87 (s, 2H), 6.19 (s, 1H), 7.18-7.36 (m, 1H), 7.37-7.51 (m, 1H), 7.61 (s, 1H). MS (ESI) m/z 445 (M+H)⁺.

Example 79 trans-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine The title compound was synthesized using the procedure as described in Example 39B by substituting 3-trifluoromethyl-5,6,7,8-tetrahydro-[1,2,4]triazolo[4,3-a]pyrazine (prepared as described in D. Kim et al, J. Med. Chem. 2005, 48, 141-151) for aniline. ¹H NMR (400 MHz, methanol-d₄) δ ppm 2.43-2.58 (m, 1H), 2.59-2.70 (m, 2H), 2.87 (dd, J=17.49, 4.91 Hz, 1H), 3.32-3.40 (m, 1H), 3.81-3.94 (m, 1H), 4.07-4.18 (m, 2H), 4.31 (t, J=5.37 Hz, 2H), 5.07 (s, 2H), 6.24 (s, 1H), 7.19-7.32 (m, 1H), 7.36-7.49 (m, 1H). MS (ESI) m/z 446 (M+H)⁺.

Example 80

3-({[trans-5-amino-4-(2,4,5-trifluorophenyl)cyclohex-1-en-1-yl]carbonyl}amino)-N N-dimethylbenzamide The title compound was synthesized using the procedure as described in Example 39B by substituting Example 27B for aniline. ¹H NMR (500 MHz, methanol-d₄) δ ppm 2.44-2.54 (m, 1H), 2.60-2.74 (m, 2H), 3.02 (s, 3H), 3.11 (s, 3H), 3.33-3.35 (m, 1H), 3.76-3.88 (m, 1H), 3.96-3.99 (m, 1H), 6.79 (s, 1H), 7.17 (d, J=7.63 Hz, 1H), 7.23-7.33 (m, 1H), 7.39-7.50 (m, 2H), 7.65-7.70 (m, J=7.02 Hz, 1H), 7.72-7.75 (m, 1H). MS (ESI) m/z 418 (M+H)⁺.

Example 81 trans-3-(piperidin-1-ylcarbonyl)-6-(2,4,5-trifluorophenyl)cyclohex-3-en-1-amine

The title compound was synthesized using the procedure as described in Example 39B by substituting piperidine for aniline. ¹H NMR (500 MHz, methanol-d₄) δ ppm 1.54-1.64 (m, 4H), 1.68-1.76 (m, 2H), 2.36-2.50 (m, 1H), 2.50-2.62 (m, 2H), 2.73 (dd, J=17.09, 4.58 Hz, 1H), 3.27-3.34 (m, 1H), 3.53-3.62 (m, 4H), 3.73-3.93 (m, 1H), 5.96 (s, 1H), 7.21-7.31 (m, 1H), 7.37-7.52 (m, 1H). MS (ESI) m/z 338 (M+H)⁺.

Example 82 trans-3-(morpholin-4-ylcarbonyl)-6-(2,4,5-trifluorophenyl)cyclohex-3-en-1-amine

The title compound was synthesized using the procedure as described in Example 39B by substituting morpholine for aniline. ¹H NMR (400 MHz, methanol-d₄) δ ppm 2.33-2.67 (m, 3H), 2.77 (dd, J=16.72, 4.76 Hz, 1H), 3.18-3.40 (m, 1H), 3.60-3.72 (m, 8H), 3.78-3.92 (m, 1H), 6.02 (s, 1H), 7.18-7.30 (m, 1H), 7.34-7.50 (m, 1H). MS (ESI) m/z 341 (M+H)⁺.

Example 83

(1R,6S)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine

Example 83A-1 methyl(4S,5R)-5-[(tert-butoxycarbonyl)amino]-4-(2,4,5-trifluorophenyl)cyclohex-1-ene-1-carboxylate A solution of Example 39A (510 mg) was dissolved in methanol (1 mL) and $CH_2Cl_2$ (1 mL). Then, (trimethylsilyl)diazomethane solution (0.4 mL, 2M in ether) was added. After ten minutes, acetic acid (0.2 mL) was added. The mixture was concentrated, filtered through a silica gel plug, and purified by chromatography (Column: Chiralcel AD, Mobile Phase: hexane/ethanol/methanol=95/2.5/2.5) to give the title compound. $^1$H NMR (500 MHz, $CDCl_3$) δ ppm 1.31 (s, 9H), 2.18-2.28 (m, 1H), 2.41-2.50 (m, 1H), 2.57-2.67 (m, 1H), 2.86 (d, J=16.48 Hz, 1H), 3.10-3.18 (m, 1H), 3.76 (s, 3H), 4.02 (s, 1H), 4.37 (d, J=7.63 Hz, 1H), 6.86-6.94 (m, 1H), 6.99 (s, 1H), 7.11 (s, 1H). MS (DCI) m/z 403 $(M+NH_4)^+$.

Example 83A-2 methyl(4R,5S)-5-[(tert-butoxycarbonyl)amino]-4-(2,4,5-trifluorophenyl)cyclohex-1-ene-1-carboxylate A solution of Example 39A (510 mg) was dissolved in methanol (1 mL) and $CH_2Cl_2$ (1 mL), and then (trimethylsilyl)diazomethane solution (0.4 mL, 2M in ether) was added. After ten minutes, acetic acid (0.2 mL) was added. The mixture was concentrated, filtered through a silica gel plug, and purified by chromatography (Column: Chiralcel AD, Mobile Phase: hexane/ethanol/methanol=95/2.5/2.5) to give the title compound. $^1$H NMR (500 MHz, $CDCl_3$) δ ppm 1.31 (s, 9H), 2.18-2.28 (m, 1H), 2.41-2.50 (m, 1H), 2.57-2.67 (m, 1H), 2.86 (d, J=16.48 Hz, 1H), 3.10-3.18 (m, 1H), 3.76 (s, 3H), 4.02 (s, 1H), 4.37 (d, J=7.63 Hz, 1H), 6.86-6.94 (m, 1H), 6.99 (s, 1H), 7.11 (s, 1H). MS (DCI) m/z 403 $(M+NH_4)^+$.

Example 83A-3 methyl(4R,5S)-5-[(tert-butoxycarbonyl)amino]-4-(2,4,5-trifluorophenyl)cyclohex-1-ene-1-carboxylate Alternative resolution procedure: A solution of Example 39A (510 mg) was dissolved in methanol (1 mL) and $CH_2Cl_2$ (1 mL), and then (trimethylsilyl)diazomethane solution (0.4 mL, 2M in ether) was added. After ten minutes, acetic acid (0.2 mL) was added. The resultant solution was concentrated in vacuo and partitioned between ethyl acetate and bicarb. The organic extract was washed with brine and dried over sodium sulfate. The crude material was deprotected using the procedure of Step B in Example 20D; and the product was partitioned between sodium bicarbonate and ethyl acetate. The organic phase was washed with brine and dried over sodium sulfate. The crude product (410 mg) was dissolved in 30 ml of ethanol. 420 mg (0.8 eq) of dibenzoyl (D)-tartaric acid was added, and the mixture was stirred until homogeneous. The resultant solution was allowed to stand overnight and the crystalline product was collected by filtration (yield 39%, ee>98%). The crystalline solid was dissolved in tetrahydrofuran (10 mL). Then, di-tert-butyl dicarbonate (1.1 eq.) and saturated sodium bicarbonate solution (5 mL) were added. After thirty minutes, the reaction mixture was concentrated and subjected to column chromatography (eluting with 20% ethyl acetate/hexane) to give the title compound.

Example 83B-1

(4S,5R)-5-[(tert-butoxycarbonyl)amino]-4-(2,4,5-trifluorophenyl)cyclohex-1-ene-1-carboxylic acid Example 83A-1 (872 mg, 2.26 mmol) in methanol (4 mL) and tetrahydrofuran (4 mL) was treated with 2N NaOH solution (5.6 mL) and stirred at room temperature for five hours. The volume of the mixture was reduced in vacuo and the resulting mixture was acidified with 2N HCl. The mixture was extracted with ethyl acetate (3×). The combined organic extract was dried ($Na_2SO_4$) and concentrated to give the title compound.

Example 83B-2

(4R,5S)-5-[(tert-butoxycarbonyl)amino]-4-(2,4,5-trifluorophenyl)cyclohex-1-ene-1-carboxylic acid Example 83A-2 (872 mg, 2.26 mmol) in methanol (4 mL) and tetrahydrofuran (4 mL) was treated with 2N NaOH solution (5.6 mL) and stirred at room temperature for five hours. The volume of the mixture was reduced in vacuo and the resulting mixture was acidified with 2N HCl. The mixture was extracted with ethyl acetate (3×). The combined organic extract was dried ($Na_2SO_4$) and concentrated to give the title compound.

Example 83C (1R,6S)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine The title compound was synthesized as using the procedure as described in Example 39B by substituting Example 83B-1 for Example 39A, and substituting 2-trifluoromethyl-5,6,7,8-tetrahydro-imidazo[1,2-a]pyrazine (prepared as described in D. Kim et al, J. Med. Chem. 2005, 48, 141-151) for aniline. $^1$H NMR (300 MHz, methanol-$d_4$) δ ppm 2.37-2.56 (m, 1H), 2.59-2.68 (m, 2H), 2.84 (dd, J=16.95, 4.75 Hz, 1H), 3.33-3.41 (m, 1H), 3.74-3.94 (m, 1H), 4.03-4.28 (m, 4H), 4.87 (s, 2H), 6.19 (s, 1H), 7.18-7.36 (m, 1H), 7.37-7.51 (m, 1H), 7.61 (s, 1H). MS (ESI) m/z 445 $(M+H)^+$.

Example 84

(1S,6R)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine The title compound was synthesized using procedure as described in Example 39B by substituting Example 83B-2 for Example 39A, and substituting 2-trifluoromethyl-5,6,7,8-tetrahydro-imidazo[1,2-a]pyrazine (prepared as described in D. Kim et al, J. Med. Chem. 2005, 48, 141-151.) for aniline. $^1$H NMR (300 MHz, methanol-$d_4$) δ ppm 2.37-2.56 (m, 1H), 2.59-2.68 (m, 2H), 2.84 (dd, J=16.95, 4.75 Hz, 1H), 3.33-3.41 (m, 1H), 3.74-3.94 (m, 1H), 4.03-4.28 (m, 4H), 4.87 (s, 2H), 6.19 (s, 1H), 7.18-7.36 (m, 1H), 7.37-7.51 (m, 1H), 7.61 (s, 1H). MS (ESI) m/z 445 $(M+H)^+$.

Example 85 trans-3-{[4-(1,3-benzodioxol-5-ylmethyl)piperazin-1-yl]carbonyl}-6-(2,4,5-trifluorophenyl)cyclohex-3-en-1-amine The title compound was synthesized using the procedure as described in Example 39B by substituting 1-piperonylpiperazine for aniline. $^1$H NMR (400 MHz, methanol-$d_4$) δ ppm 2.40-2.69 (m, 3H), 2.83 (dd, J=17.64, 5.37 Hz, 1H), 3.31-3.40 (m, J=4.30 Hz, 8H), 3.79-3.90 (m, 1H), 4.30 (s, 2H), 6.03 (s, 2H), 6.12 (s, 1H), 6.86-6.95 (m, 1H), 6.96-7.03 (m, 2H), 7.19-7.31 (m, 1H), 7.34-7.46 (m, 1H). MS (ESI) m/z 474 (M+H)$^+$.

Example 86 trans-3-(piperazin-1-ylcarbonyl)-6-(2,4,5-trifluorophenyl)cyclohex-3-en-1-amine

The title compound was synthesized using the procedure as described in Example 39B by substituting piperazine for aniline. $^1$H NMR (500 MHz, methanol-$d_4$) δ ppm 2.42-2.69 (m, 3H), 2.82 (dd, J=17.24, 4.73 Hz, 1H), 3.25-3.38 (m, 5H), 3.77-3.99 (m, 5H), 6.12 (s, 1H), 7.17-7.32 (m, 1H), 7.32-7.49 (m, 1H). MS (ESI) m/z 340 (M+H)$^+$.

Example 87

(1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine The title compound was prepared using the procedure as described in Example 39B by substituting Example 83B-2 for Example 39A, and substituting 3-trifluoromethyl-5,6,7,8-tetrahydro-[1,2,4]triazolo[4,3-a]pyrazine (D. Kim et al, J. Med. Chem. 2005, 48, 141-151) for aniline. $^1$H NMR (400 MHz, methanol-$d_4$) δ ppm 2.43-2.58 (m, 1H), 2.59-2.70 (m, 2H), 2.87 (dd, J=17.49, 4.91 Hz, 1H), 3.32-3.40 (m, 1H), 3.81-3.94 (m, 1H), 4.07-4.18 (m, 2H), 4.31 (t, J=5.37 Hz, 2H), 5.07 (s, 2H), 6.24 (s, 1H), 7.19-7.32 (m, 1H), 7.36-7.49 (m, 1H).

Example 88

(1S,6R)-3-(1,3-thiazolidin-3-ylcarbonyl)-6-(2,4,5-trifluorophenyl)cyclohex-3-en-1-amine The title compound was made using the procedure as described in Example 39B by substituting thiazolidine for aniline, and substituting Example 83B-2 for Example 39A. $^1$H NMR (500 MHz, methanol-$d_4$) δ ppm 2.44-2.53 (m, 1H), 2.53-2.70 (m, 2H), 2.84 (dd, J=16.94, 5.03 Hz, 1H), 3.09 (t, J=6.41 Hz, 2H), 3.31-3.37 (m, 1H), 3.78-3.94 (m, 3H), 4.66 (s, 2H), 6.23 (s, 1H), 7.20-7.32 (m, 1H), 7.38-7.49 (m, 1H). MS (ESI) m/z 343 (M+H)$^+$.

Example 89

(1S,6R)-3-(3,4-dihydroisoquinolin-2(1H)-ylcarbonyl)-6-(2,4,5-trifluorophenyl)cyclohex-3-en-1-amine The title compound was made using the procedure as described in Example 39B by substituting 1,2,3,4-tetrahydroisoquinoline for aniline, and substituting Example 83B-2 for Example 39A. $^1$H NMR (500 MHz, methanol-$d_4$) δ ppm 2.43-2.54 (m, 1H), 2.54-2.69 (m, 2H), 2.78 (d, J=14.34 Hz, 1H), 2.93 (t, J=5.49 Hz, 2H), 3.32-3.40 (m, 1H), 3.82-3.95 (m, 3H), 4.77 (s, 2H), 6.09 (s, 1H), 7.11-7.23 (m, 4H), 7.23-7.32 (m, 1H), 7.40-7.51 (m, 1H). MS (ESI) m/z 387 (M+H)$^+$.

Example 90 trans-6-(2,4-dichlorophenyl)cyclohexane-1-amine

To a solution of Example 2B (100 mg, 0.041 mmol) in 1:1 in methanol (2 mL), two drops of concentrated HCl and 10% palladium on carbon (10 mg) were added. The solution was purged with nitrogen and subjected to an atmosphere of $H_2$ over a twelve hour period. The solution was filtered through Celite and concentrated to give the title compound. $^1$H NMR (300 MHz, $C_5D_5N$) δ ppm 7.26 (s, 1H), 7.17-7.19 (m, 2H), 3.96-3.99 (m, 1H), 3.65-3.69 (m, 1H), 2.94-2.96 (m, 1H), 2.06-2.08 (m, 1H), 1.80-1.83 (m, 1H), 1.58-1.67 (m, 2H), 1.25-1.39 (m, 3H). MS (ESI+) m/z 245 (M+H)$^+$.

Example 91

(1S,2R)-5-{[2-(trifluoromethyl)-5,6-dihydroimidazo[1,2-a]pyrazin-7(8H)-yl]carbonyl}-2-(2,4,5-trifluorophenyl)cyclohexanamine Example 84 (20 mg), 10% Pd/C (30 mg) were mixed in 2 mL of ethanol and hydrogenated at 55° C. under 50 psi of $H_2$ overnight. The mixture was cooled to room temperature and filtered. The filtrate was concentrated and purified by reverse-phase high pressure liquid chromatography (eluting with 0-70% acetonitrile/water and 0.1% trifluoroacetic acid) to give the title compound. $^1$H NMR (500 MHz, methanol-$d_4$) δ ppm 1.59-1.71 (m, 1H), 1.79-1.99 (m, 4H), 2.19 and 2.37 (m, 1H), 2.97 (m, 1H), 3.12 (m, 0.6H), 3.47 and 3.62 (m, 1H), 4.0-4.3 (m, 4.4H), 4.7-4.9 (overlapped with water peak in methanol-$d_4$), 7.18-7.26 (m, 1H), 7.41 and 7.33 (m, 1H), 7.61 and 7.60 (s, 1H). MS (ESI) m/z 447 (M+H)$^+$.

Example 92

(1S,6R)-3-[5-(ethylsulfonyl)-1,3-benzoxazol-2-yl]-6-(2,4,5-trifluorophenyl)cyclohex-3-en-1-amine Example 83B-2 (20 mg, 0.054 mmol) was combined with (25 mg, 0.12 mmol) of 2-amino-4-ethylsulfonyl-phenol and ground together in a reaction tube. Polyphosphoric acid (~0.2 ml) was added and the ingredients were mixed thoroughly. The mixture was heated at 140° C. for fifty minutes, wherein gas evolved, and the mixture turned black. After cooling to ambient temperature, 1 ml of water was added, and the resultant solution was purified by reversed-phase HPLC (eluting with 0-70% acetonitrile/water with 0.1% trifluoroacetic acid) to provide the title compound as a trifluoroacetic acid salt. MS (ESI+) m/z 437 (m+H)$^+$. $^1$H NMR ($CD_3OD$) δ 1.24 (t, 3H, J=8 Hz), 2.7-2.85 (m, 3H), 3.28 (q, 2H, J=8 Hz), 3.45 (m, 2H), 3.98 (dt, 1H, J=6.12 Hz), 7.30 (m, 2H), 7.45 (dt, 1H, J=6, 7 Hz), 7.86 (d, 1H, J=10 Hz), 7.98 (dd, 1H, J=2.10 Hz), 8.23 (d, 1H, J=2 Hz).

Example 93

2-[(4R,5S)-5-amino-4-(2,4,5-trifluorophenyl)cyclohex-1-en-1-yl][1,3]thiazolo[5,4-b]pyridin-5-ol The trifluoroacetic acid salt of the title compound was prepared using the procedure as described in Example 92 by substituting 3-amino-6-methoxypyridine-2-thiol for 2-amino-4-ethylsulfonyl-phenol. MS (ESI+) m/z 378

(m+H)+. 1H NMR (CD3OD) δ 2.7-2.8 (m, 3H), 3.45 (m, 2H), 3.95 (dt, 1H, J=6.12 Hz), 6.72 (d, 1H, J=10 Hz), 6.78 (br s, 1H), 7.27 (dt, 1H, J=6.8 Hz), 7.47 (dt, 1H, J=6.7 Hz), 8.05 (d, 1H, J=10 Hz).

Example 94

(1S,6R)-3-(5-methoxy[1,3]thiazolo[5,4-b]pyridin-2-yl)-6-(2,4,5-trifluorophenyl)cyclohex-3-en-1-amine The trifluoroacetic acid salt of the title compound was prepared using the procedure as described in Example 92 by substituting 3-amino-6-methoxypyridine-2-thiol for 2-amino-4-ethylsulfonyl-phenol. MS (ESI+) m/z 392 (m+H)+. 1H NMR (CD3OD) δ 2.7-2.8 (m, 3H), 3.44 (m, 2H), 3.97 (dt, 1H, J=6.12 Hz), 3.99 (s, 3H), 6.84 (br s, 1H), 6.91 (d, 1H, J=10 Hz), 7.29 (dt, 1H, J=6.8 Hz), 7.47 (dt, 1H, J=6.7 Hz), 8.10 (d, 1H, J=10 Hz).

Example 95

2-[(4R,5S)-5-amino-4-(2,4,5-trifluorophenyl)cyclohex-1-en-1-yl]-N-methyl[1,3]thiazolo[5,4-d]pyrimidin-7-amine The trifluoroacetic acid salt of the title compound was prepared using the procedure as described in Example 92 by substituting 5 amino-6-methylamino-pyrimidine-4-thiol (Brown, J. Appl. Chem. 1957, 110) for 2-amino-4-ethylsulfonyl-phenol. MS (ESI+) m/z 392 (m+H)+. 1H NMR (CD3OD) δ 2.7-2.8 (m, 3H), 3.15 (s, 3H), 3.44 (m, 2H), 3.96 (dt, 1H, J=6.12 Hz), 6.93 (br s, 1H), 7.29 (dt, 1H, J=6.8 Hz), 7.46 (dt, 1H, J=6.7 Hz), 8.41 (s, 1H).

Example 96

1,2,4-Trifluoro-5-(1-nitropent-4-en-2-yl)benzene

To a cooled (−40° C.) solution of (E)-1,2,4-trifluoro-5-(2-nitrovinyl)benzene (250 g, 1.23 mol) in THF (490 mL), allyl-magnesium chloride (800 mL, 1.6 mol, 2 M in THF) was added at such a rate as to maintain the internal temperature below −20° C. The solution was stirred at −20° C. for thirty minutes and then carefully quenched by the addition of 2M HCl (1 L), while maintaining the temperature below −5° C. Methyl t-butyl ether (500 mL) was added, and the biphasic solution was allowed to warm to >10° C. The layers were separated, and the organic was washed with $H_2O$ (1×500 mL), saturated aqueous $NaHCO_3$ (1×500 mL), and brine (1×500 mL). The organic layer was concentrated to dryness, and the crude product was filtered through a 450 g plug of silica gel (eluting with 5% ethyl acetate in hexane at a flow rate of 90 mL/min). The first 100 mL of eluent was discarded, and the subsequent 2 L were collected and concentrated to dryness to give the title compound as an oil (268 g, 89%). 1H NMR (300 MHz, CDCl3) δ ppm 7.05-6.90 (m, 2H), 5.65 (dddd, J=7.5, 7.5, 9.5, and 16.6, Hz, 1H), 5.12-5.06 (m, 2H), 4.63 (d, J=7.5 Hz, 2H), 3.75 (p, J=7.5 Hz, 1H), and 2.48 (t, J=7.5 Hz, 2H).

Example 97

Methyl 2-methylene-4-nitro-5-(2,4,5-trifluorophenyl)oct-7-enoate

To a cooled (5° C.) and mechanically-stirred solution of 1,2,4-trifluoro-5-(1-nitropent-4-en-2-yl)benzene (266.3 g, 1.09 mol) and bromocrotonate (151 mL, 1.13 mol) in THF (270 mL), NaOH (322 mL, 1.61 mol, 5 M) was added. The resulting biphasic mixture was stirred vigorously for thirty minutes. The mixture was allowed to warm to room temperature, and was then diluted with methyl t-butyl ether (950 mL). The layers were separated, and the organic was washed with $H_2O$ (2×500 mL) and brine (1×500 mL). The organic layer was dried with anhydrous $Na_2SO_4$ and concentrated under reduced pressure to give the title compound as a 1:1 mixture of erythro and threo isomers (365 g, 98%). Threo isomer: 1H NMR (300 MHz, CDCl3) δ ppm 7.00-6.86 (m, 2H), 6.25 (s, 1H), 5.66 (br s, 1H), 5.57 (dddd, J=6.8, 6.8, 10.5, and 17.3 Hz, 1H), 5.12-4.97 (m, 2H), 3.80 (s, 3H), 3.50 (ddd, J=5.4, 9.5 and 9.5 Hz, 1H), 3.12 (ddd, J=1.0, 2.7, and 14.0 Hz, 1H), 2.72 (dd, J=11.2 and 14.0 Hz, 1H), 2.63-2.59 (m, 1H), and 2.52-2.38 (m, 1H). Erythro isomer: 1H NMR (300 MHz, CDCl3) δ ppm 7.09-6.91 (m, 2H), 6.20 (br s, 1H), 5.60 (br s, 1H), 5.56-5.42 (m, 1H), 5.09-4.91 (m, 2H), 3.75 (s, 3H), 3.55 (ddd, J=6.1, 10.5, and 10.5 Hz, 1H), 2.62-2.59 (m, 2H), and 2.44-2.38 (m, 2H).

Example 98

Methyl trans-5-nitro-4-(2,4,5-trifluorophenyl)cyclohex-1-enecarboxylate

A stream of dinitrogen gas was bubbled through a mechanically-stirred solution of methyl 2-methylene-4-nitro-5-(2,4,5-trifluorophenyl)oct-7-enoate (98 g, 285.7 mmol, 1:1 mixture of erythro and threo isomers) in DCE (1.43 L) at 70° C. A solution of Grubbs' $2^{nd}$ generation catalyst (9.7 g, 11.4 mmol) in DCE (61 mL) was added via syringe pump over about twelve hours. The reaction was then cooled to 55° C., and triethylamine (3.98 mL, 28.6 mmol) was added. After eight hours, the heating bath was removed, and DMSO (64 mL, 912 mmol) was added to the reaction. After stirring for twelve hours, the reaction was concentrated under reduced pressure, and the crude residue was purified by MPLC on $SiO_2$ gel (15% EtOAc in Hx) to give the title compound as a dark waxy solid (63 g, 72%). 1H NMR (300 MHz, CDCl3) δ ppm 7.06-6.90 (m, 3H), 5.03 (ddd, J=5.8, 10.5 and 10.5 Hz, 1H), 3.79 (s, 3H), 3.64 (ddd, J=6.1, 10.5, and 10.5 Hz, 1H), 3.20-3.12 (m, 1H), 3.01-2.89 (m, 1H), 2.80-2.70 (m, 1H), 2.63-2.51 (m, 1H).

Example 99

Methyl trans-5-amino-4-(2,4,5-trifluorophenyl)cyclohex-1-enecarboxylate

A mixture of trans-ethyl 5-nitro-4-(2,4,5-trifluorophenyl)cyclohex-1-enecarboxylate (500 g, 1.59 mol) and Fe powder (90 g, 1.6 mol) in ethanol (3.2 L) and 2 M HCl (3.2 L) was heated to 45° C., whereupon the internal temperature of the reaction increased to 65° C. over the course of 0.5 hours. After the internal temperature had fallen to 45° C., a second portion of Fe powder (135 g, 2.4 mol) was added, resulting in an increase in internal temperature to 73° C. After thirty minutes, a third aliquot of Fe powder (90 g, 1.6 mol) was added, and the reaction was allowed to stir for one hour, after which the heating bath was removed. Ammonium hydroxide (~100 mL) was then added to the ambient mixture until the pH was 8. The mixture was filtered though celite, eluting with boiling EtOH. The ethanol was removed under reduced pressure, and the aqueous was acidified with concentrated HCl to pH ~3. The aqueous layer was then washed with diethyl ether (3×1 L), and the combined dark organic layers were discarded. The aqueous layer was basified with ammonium hydroxide, and the resulting emulsion was filtered through celite (eluting with hot EtOH). The filtrate was concentrated under reduced pressure, and the residue was partitioned between ethyl acetate and saturated aqueous NaHCO$_3$. The layers were separated, and the organic was washed with saturated aqueous NaHCO$_3$, dried over Na$_2$SO$_4$, filtered, and concentrated under reduced pressure to give the title compound as an oil (344 g, 75%).

Example 100

Methyl(4R,5S)-5-amino-4-(2,4,5-trifluorophenyl) cyclohex-1-enecarboxylate

Methyl trans-5-amino-4-(2,4,5-trifluorophenyl)cyclohex-1-enecarboxylate (108 g, 0.378 mol) dissolved in 1.67 L of EtOH was added into dibenzoyl-D-tartaric acid (DBTA, 108 g, 0.8 equivalent) in 4.16 L of EtOH with stirring at room temperature. The stirring was continued for two hours. The precipitate was collected by filtration, washed with 0.4 L of 30% EtOH/Hexanes, and then dried in vacuum to give crude methyl(4R,5S)-5-amino-4-(2,4,5-trifluorophenyl)cyclohex-1-ene-1-carboxylate DBTA salt (106.07 g, 45%). The salt was mixed with 2.4 L of EtOH, and the mixture was heated to 80° C. with stirring by a mechanical stirrer. After stirring for fifty minutes, the mixture was cooled to room temperature. The solid was filtered, washed with 0.4 L of 40% EtOH/Hexanes and then dried in vacuum to give 87.12 g of methyl(4R,5S)-5-amino-4-(2,4,5-trifluorophenyl)cyclohex-1-ene-1-carboxylate DBTA salt (82%).

A small aliquot (25 mg, 0.04 mmol) of the above salt was combined with Boc$_2$O (26 mg, 3 equiv.) in 2 mL of 1:1 THF:CH$_2$Cl$_2$, then Et$_3$N (34.4 ml, 6 equivalent) was added. After three hours, the reaction mixture was partitioned between EtOAc and aqueous NaHCO$_3$. The EtOAc layer was dried over sodium sulfate, filtered, and concentrated under reduced pressure to give methyl(4R,5S)-5-[(tert-butoxycarbonyl)amino]-4-(2,4,5-trifluorophenyl)-cyclohex-1-ene-1-carboxylate. The optical purity was ≧95% as determined by chiral analytical HPLC using a (R, R) Whelk-01 column (Regis Technology, Inc., 25 cm×4.6 mm)(eluting with 5% to 8% isopropanol/hexanes at 0.8 to 1 mL/minute). The desired (4R,5S)-isomer is slower eluting and the undesired (4S,5R)-isomer is faster eluting.

Example 101

(4R,5S)-5-tert-Butoxycarbonylamino-4-(2,4,5-trifluoro-phenyl)-cyclohex-1-enecarboxylic acid Amine DBTA salt (167.8 g, 0.27 mol) was dissolved in THF (960 mL). The mixture was cooled to 0° C. and Et$_3$N (70 mL, 0.5 mol) was added followed by (Boc)$_2$O (70.3 g, 0.32 mol). After two hours, the reaction mixture was concentrated and saturated NaHCO$_3$ solution (800 mL) was added. The mixture was extracted with ethyl acetate and the combined organic extract was washed with water, brine, dried over sodium sulfate, filtered, and concentrated under reduced pressure to give the ester as a solid (118 g).

The above ester (118 g) was dissolved in EtOH (520 mL) and the mixture was cooled to 0° C. Then, NaOH (2N, 668 mL) was added. The mixture was stirred for one hour and then concentrated. 6 N HCl (230 mL) was added to bring pH ~2. The mixture was extracted with ethyl acetate, and the combined organic extract was washed with water, brine, dried over sodium sulfate, filtered, and concentrated under reduced pressure to give the acid as a solid (101.6 g).

Example 102

(1S,6R)-[3-(2-Trifluoromethyl-5,6-dihydro-8H-imidazo[1,2-a]pyrazine-7-carbonyl)-6-(2,4,5-trifluoro-phenyl)-cyclohex-3-enyl]-carbamic acid tert-butyl ester (4R,5S)-5-tert-Butoxycarbonylamino-4-(2,4,5-trifluorophenyl)-cyclohex-1-enecarboxylic acid (98.4 g) and EDCI (60.8 g 0.32 mol), HOBT (43 g, 0.32 mol) were mixed in THF/DMF (120 mL/120 mL). The mixture was cooled to 0° C. and diisopropylethyl amine (151.5 mL, 0.86 mol) was added slowly. The mixture was stirred for approximate twenty minutes, and then 2-trifluoromethyl-5,6,7,8-tetrahydro-imidazo[1,2-a]pyrazine HCl salt (83.9 g, 0.32 mol) was added. The mixture was stirred overnight, and concentrated in vacuo. Ethyl acetate (1000 mL) was added followed by 1N HCl (750 mL). The mixture was extracted with ethyl acetate, and the combined organic extract was washed with saturated NaHCO$_3$ (750 mL), water, and brine, dried over sodium sulfate, filtered, and concentrated under reduced pressure to give an oil (153.6 g). The crude amide (228 g) was dissolved in 470 mL of EtOH, and 1350 mL of hexanes was added with stirring. After stirring overnight, the solid was collected by filtration, washed with 450 mL of 50% Et$_2$O/hexanes and then dried in vacuum at 45° C. to give 165.8 g (73%) of product as a white solid.

Example 103

(4R,5S)-[5-Amino-4-(2,4,5-trifluoro-phenyl)-cyclohex-1-enyl]-(2-trifluoromethyl-5,6-dihydro-8H-imidazo[1,2-a]pyrazin-7-yl)-methanone, tosylate salt 233.95 g of (1S,6R)-[3-(2-Trifluoromethyl-5,6-dihydro-8H-imidazo[1,2-a]pyrazine-7-carbonyl)-6-(2,4,5-trifluoro-phenyl)-cyclohex-3-enyl]-carbamic acid tert-butyl ester (0.429 mol) was dissolved in 185 mL of MeOH, cooled to 0° C., and then 554 mL of 4N HCl in dioxane was added. An additional 100 mL of 4N HCl in dioxane was added after thirty minutes. After 1.5 hours, the mixture was concentrated in vacuo. The resulting solid was dissolved in a minimum amount of MeOH (approximately 4 L), and this solution was slowly poured into Et$_2$O (20 L) with stirring. The precipitate was collected by filtration, washed with 0.7 L of EtOAc, 0.5 L of Et$_2$O and then dried in vacuo at 45° C. to give 220 g of the HCl salt. This material was dissolved in 2.2 L of water, and stirred efficiently as 100 g of NaHCO$_3$ was added cautiously (gas evolves). The mixture was extracted with 1 L of EtOAc; 50 g of NaCl was added, and the solution was extracted twice with 200 mL of EtOAc. The combined organics were washed with brine, dried over Na$_2$SO$_4$, and concentrated in vacuo to give a slightly-yellow foam. This material was dissolved in 500 mL of EtOH. This solution was stirred while a solution of 86 g of p-toluenesulfonic acid in 200 mL of EtOH was added. The resultant mixture was seeded and stirred at room temperature for four hours. The resultant solid was collected by filtration and washed with EtOH. The combined filtrates were concentrated to one-half volume, stirred for two hours, and filtered to collect a second crop of solid, which was washed with EtOH. The process was repeated to give a third crop of solid. The solids were combined and dried overnight in a vacuum oven at a temperature of 40° C. The overall yield of solid is 250.7 g (82%).

It is understood that the foregoing detailed description and accompanying examples are merely illustrative and are not to be taken as limitations upon the scope of the invention. Various changes and modifications including, but not limited to, those relating to the chemical structures, substituents, derivatives, intermediates, syntheses, formulations and/or methods of use of the invention, can be made without departing from the spirit of the present invention and scope thereof.

What we claim is:

1. A compound of formula (I)

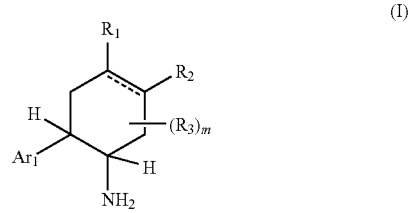

or a pharmaceutically acceptable salt, prodrug, salt of a prodrug, or a combination thereof, wherein $R_1$ is selected from the group consisting of hydrogen, alkyl, haloalkyl, aryl, heteroaryl, heterocycle, cycloalkyl and cycloalkenyl; and $R_2$ is —C(O)G;

G is $R_4$;

$R_4$ at each occurrence is independently selected from the group consisting of aryl, heteroaryl, cycloalkyl, cycloalkenyl, and heterocycle; wherein the aryl, heteroaryl, heterocycle, cycloalkyl, cycloalkenyl, and the heterocycle moiety of heterocyclealkyl, represented by $R_1$, and $R_4$, are each independently unsubstituted or substituted with 1, 2, 3, 4 or 5 substituents independently selected from the group consisting of $R_7$, alkyl, alkenyl, —CN, —NO$_2$, halo, ethylenedioxy, methylenedioxy, oxo, —OR$_{7A}$, —OC(O)R$_{7A}$, —OC(O)OR$_{7A}$, —OS(O)$_2$R$_{7A}$, —S(alkyl), —S(O)alkyl, —S(O)$_2$R$_{7A}$, —S(O)$_2$OR$_{7A}$, —S(O)$_2$NR$_{7A}$R$_b$, —C(O)R$_{7A}$, —C(O)OR$_{7A}$, —C(O)NR$_{7A}$R$_b$, —NR$_{7A}$R$_b$, —NOR$_{7A}$, —N(R$_b$)C(O)R$_{7A}$, —N(R$_b$)C(O)OR$_{7A}$, —N(R$_b$)S(O)$_2$R$_{7A}$, —N(R$_b$)C(O)NR$_{7A}$R$_b$, —N(R$_b$)S(O)$_2$NR$_{7A}$R$_b$, haloalkyl, cyanoalkyl, nitroalkyl, -alkylenyl-OR$_{7A}$, -alkylenyl-OC(O)R$_{7A}$, -alkylenyl-OC(O)OR$_{7A}$, -alkylenyl-OS(O)$_2$R$_{7A}$, -alkylenyl-S(alkyl), -alkylenyl-S(O)alkyl, -alkylenyl-S(O)$_2$R$_{7A}$, -alkylenyl-S(O)$_2$OR$_{7A}$, -alkylenyl-S(O)$_2$NR$_{7A}$R$_b$, -alkylenyl-C(O)R$_{7A}$, -alkylenyl-C(O)OR$_{7A}$, -alkylenyl-C(O)NR$_{7A}$R$_b$, -alkylenyl-NR$_{7A}$R$_b$, -alkylenyl-NOR$_{7A}$, -alkylenyl-N(R$_b$)C(O)R$_{7A}$, -alkylenyl-N(R$_b$)C(O)OR$_{7A}$, -alkylenyl-N(R$_b$)S(O)$_2$R$_{7A}$, -alkylenyl-N(R$_b$)C(O)NR$_{7A}$R$_b$, -alkylenyl-N(R$_b$)S(O)$_2$NR$_{7A}$R$_b$ and -alkylenyl-R$_7$;

$R_{7A}$ at each occurrence is independently selected from the group consisting of hydrogen, alkyl, alkenyl, haloalkyl, —R$_7$ and -alkylenyl-R$_7$; and $R_7$ at each occurrence is independently selected from the group consisting of aryl, heteroaryl, cycloalkyl, cycloalkenyl and heterocycle;

each $R_3$ is independently selected from the group consisting of hydrogen, alkyl, and haloalkyl;

----- is double bond;

m is 4;

$Ar_1$ is a phenyl group;

the phenyl, aryl, heteroaryl, cycloalkyl, cycloalkenyl, and heterocycle represented by $Ar_1$ and $R_7$, are independently unsubstituted or substituted with 1, 2, 3, 4 and 5 substituents independently selected from the group consisting of alkyl, alkenyl, —CN, —NO$_2$, halo, ethylenedioxy, methylenedioxy, oxo, —OR$_a$, —OC(O)alkyl, —OC(O)Oalkyl, —OS(O)$_2$alkyl, —S(alkyl), —S(O) alkyl, —S(O)$_2$alkyl, —S(O)$_2$OR$_a$, —S(O)$_2$NR$_a$R$_b$, —C(O)R$_a$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)alkyl, -alkylenyl-OC(O)Oalkyl, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)OR$_a$, -alkylenyl-C(O)NR$_a$R$_b$, -alkylenyl-NR$_a$R$_b$, -alkylenyl-NOR$_a$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$;

$R_a$ at each occurrence is independently selected from the group consisting of hydrogen, alkyl, alkenyl and haloalkyl, and $R_b$ at each occurrence is independently selected from the group consisting of hydrogen and alkyl.

2. The compound of claim 1 wherein $R_1$ is selected from the group consisting of hydrogen, unsubstituted and substituted aryl and unsubstituted and substituted heteroaryl.

3. The compound of claim 1 wherein and $R_1$ is selected from the group consisting of hydrogen and unsubstituted and substituted aryl.

4. The compound of claim 1 wherein $R_1$ is selected from the group consisting of hydrogen, and unsubstituted and substituted phenyl.

5. The compound of claim 1 wherein $R_1$ is selected from the group consisting of hydrogen, unsubstituted and substituted phenyl and unsubstituted and substituted pyridinyl.

6. The compound of claim 1 wherein $R_1$ is hydrogen.

7. The compound of claim 1 wherein $R_1$ is hydrogen, and $R_4$ is unsubstituted and substituted heterocycle.

8. The compound of claim 1 wherein $R_1$ is hydrogen, and $R_4$ is a heterocycle ring selected from the group consisting of piperidinyl, pyrrolidinyl, 1,2,3,4-tetrahydroisoquinolin-2-yl, 5,6-dihydroimidazo[1,2-a]pyrazin-7(8H)-yl, 5,6-dihydro[1,2,4]triazolo[4,3-a]pyrazin-7(8H)-yl, piperazinyl, morpholinyl, and 1,3-thiazolidin-3-yl, each of which is independently unsubstituted or substituted.

9. The compound of claim 7 selected from the group consisting of

2-{[trans-5-amino-4-(2,4,5-trifluorophenyl)cyclohex-1-en-1-yl]carbonyl}-1,2,3,4-tetrahydroisoquinoline-7-carboxamide;

1-{[trans-5-amino-4-(2,4,5-trifluorophenyl)cyclohex-1-en-1-yl]carbonyl}piperidine-4-carboxamide;

trans-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;

trans-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine;

trans-3-(piperidin-1-ylcarbonyl)-6-(2,4,5-trifluorophenyl)cyclohex-3-en-1-amine;

trans-3-(morpholin-4-ylcarbonyl)-6-(2,4,5-trifluorophenyl)cyclohex-3-en-1-amine;

(1R,6S)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;

(1S,6R)-3-{[2-(trifluoromethyl)-5,6-dihydroimidazo[1,2-a]pyrazin-7(8H)-yl]carbonyl}-6-(2,4,5-trifluorophenyl)cyclohex-3-en-1-amine;

trans-3-{[4-(1,3-benzodioxol-5-ylmethyl)piperazin-1-yl]carbonyl}-6-(2,4,5-trifluorophenyl)cyclohex-3-en-1-amine;

trans-3-(piperazin-1-ylcarbonyl)-6-(2,4,5-trifluorophenyl)cyclohex-3-en-1-amine;

(1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine;

(1S,6R)-3-(1,3-thiazolidin-3-ylcarbonyl)-6-(2,4,5-trifluorophenyl)cyclohex-3-en-1-amine; and (1S,6R)-3-(3,4-dihydroisoquinolin-2(1H)-ylcarbonyl)-6-(2,4,5-trifluorophenyl)cyclohex-3-en-1-amine;

or a pharmaceutically acceptable salt, prodrug, salt of a prodrug or a combination thereof.

10. A pharmaceutical composition comprising a therapeutically effective amount of a compound of formula (I) of claim 1 in combination with a pharmaceutically suitable carrier.

* * * * *